US012685445B2

(12) United States Patent
Chan et al.

(10) Patent No.: US 12,685,445 B2
(45) Date of Patent: Jul. 21, 2026

(54) SYSTEMS, DEVICES AND METHODS FOR ANTEGRADE DISSECTION AND REENTRY

(71) Applicants: Simpson Interventions, Inc., Campbell, CA (US); Kin F. Chan, Campbell, CA (US); John B. Simpson, Campbell, CA (US)

(72) Inventors: Kin F. Chan, Campbell, CA (US); John B. Simpson, Campbell, CA (US); Marcelo Siero, Campbell, CA (US); Rafael Espericueta, Campbell, CA (US); Ashwin Balaji, Campbell, CA (US); Willis Lam, Campbell, CA (US); Douglas Rowe, Campbell, CA (US); August Pombo, Campbell, CA (US); Wendy Lam, Campbell, CA (US)

(73) Assignee: Elumn8 Medical, Inc., Campbell, CA (US)

( * ) Notice: Subject to any disclaimer, the term of this patent is extended or adjusted under 35 U.S.C. 154(b) by 0 days.

(21) Appl. No.: 18/839,409

(22) PCT Filed: Feb. 21, 2023

(86) PCT No.: PCT/US2023/062968
§ 371 (c)(1),
(2) Date: Aug. 16, 2024

(87) PCT Pub. No.: WO2023/159255
PCT Pub. Date: Aug. 24, 2023

(65) Prior Publication Data
US 2025/0152013 A1 May 15, 2025

Related U.S. Application Data

(60) Provisional application No. 63/479,850, filed on Jan. 13, 2023, provisional application No. 63/311,871,
(Continued)

(51) Int. Cl.
*A61B 5/00* (2006.01)

(52) U.S. Cl.
CPC .................................. *A61B 5/0084* (2013.01)

(58) Field of Classification Search
CPC .................................................... A61B 5/0084
See application file for complete search history.

(56) References Cited

U.S. PATENT DOCUMENTS 6,398,755 B1 * 6/2002 Belef ................. A61M 25/0113
604/95.01
6,482,162 B1 11/2002 Moore
(Continued)

FOREIGN PATENT DOCUMENTS

WO 2006049787 A2 5/2006
WO 2021062322 A1 4/2021
(Continued)

OTHER PUBLICATIONS

International Preliminary Report on Patentability issued in International Application No. PCT/US2023/062968, mailed on Aug. 29, 2024, 13 pages.
(Continued)

*Primary Examiner* — Joseph M Santos Rodriguez
(74) *Attorney, Agent, or Firm* — Dorsey & Whitney LLP

(57) ABSTRACT

An exemplary catheter includes a housing having the distal catheter region configured to be at least partially disposed in a body and the proximal catheter region configured to remain at least partially outside of the body. The catheter may define an imaging lumen configured to receive an imaging device, a guidewire lumen, an off-ramp, and an indicator lumen configured to receive an indicator that is detectable by the imaging device. The guidewire lumen is configured to receive a guidewire and includes a distal region and a proximal region. The off-ramp extends from the
(Continued)

guidewire lumen at or near an intersection of the distal and proximal regions of the guidewire lumen. The catheter may also include one or more guidewire feeders configured to cause the guidewire to move from the proximal section to the off-ramp.

20 Claims, 53 Drawing Sheets

Related U.S. Application Data filed on Feb. 18, 2022, provisional application No. 63/311,852, filed on Feb. 18, 2022.

(56) References Cited

U.S. PATENT DOCUMENTS

| | | |
|---|---|---|
| 7,632,241 B2 | 12/2009 | Raijman et al. |
| 11,064,869 B2 | 7/2021 | Mcweeney et al. |
| 11,179,138 B2 | 11/2021 | Chiang et al. |
| 2007/0038114 A1 | 2/2007 | Couvillon |
| 2010/0042084 A1 | 2/2010 | Nariyuki et al. |
| 2011/0288374 A1 | 11/2011 | Hadani et al. |
| 2014/0243742 A1 | 8/2014 | Pacheco et al. |
| 2020/0405892 A1 | 12/2020 | Zaborsky |

FOREIGN PATENT DOCUMENTS

| | | |
|---|---|---|
| WO | 2021216933 | 10/2021 |
| WO | 2023159255 A2 | 8/2023 |

OTHER PUBLICATIONS

International Search Report and Written Opinion issued in International Application No. PCT/US2023/062968, issued on Aug. 28, 2023, 18 pages.
Supplementary European Search Report issued in European Patent Application No. 23757179.9, mailed on Oct. 2, 2025, 11 pages.

* cited by examiner

1

SYSTEMS, DEVICES AND METHODS FOR ANTEGRADE DISSECTION AND REENTRY

CROSS-REFERENCE TO RELATED APPLICATIONS

This application is a 371 National Stage entry of PCT application No. PCT/US2023/062968, filed on Feb. 21, 2023, which in turn claims priority to U.S. Provisional Patent Application No. 63/311,852, filed Feb. 18, 2022, entitled "METHODS AND SYSTEMS CONFIGURED TO DETERMINE AN ORIENTATION OF A CATHETER"; U.S. Provisional Patent Application No. 63/311,871, filed Feb. 18, 2022, entitled "ROTATIONAL IMAGING DISTORTION CORRECTION"; and U.S. Provisional Patent Application No. 63/479,850, filed Jan. 13, 2023, entitled "SYSTEMS, DEVICES AND METHODS FOR ANTEGRADE DISSECTION AND REENTRY" each of which is incorporated by reference herein, in the entirety and for all purposes.

SUMMARY

Anatomically complex chronic total occlusions (CTO) often require leveraging the extraplaque or formerly "sub-intimal" space for successful CTO recanalization. Antegrade dissection and reentry (ADR) technique is an important part of the hybrid approach to contemporary CTO percutaneous coronary intervention (PCI). However, despite the availability of dedicated re-entry devices, the success rate for ADR is around 50-60% in large registries. This is often due to large extraplaque hematoma formation leading to loss of distal vessel visualization and loss of guidewire support and maneuverability making re-entry challenging. Both existing ADR and antegrade wire escalation are blinded strategies given the lack of realtime visual guidance by angiography and their inability to provide a high degree of precision in steering and advancing a re-entry device.

Embodiments are directed to methods and systems configured to perform intravascular imaging and/or antegrade dissection and reentry for the treatment of chronic total occlusion of a blood vessel, including coronary and peripheral vasculature. The catheter may be configured to support and aim steerable guidewires with guidance from concurrent optical coherence tomography ("OCT") imaging, for example. In some examples, the catheter may comprise a tip with a radio-opaque marker, a torque shaft, a catheter rotator assembly, a guidewire introducer port, an imaging driveshaft with an optical fiber, imager with longitudinal translation and a housing. The tip of the catheter further comprises two ports, one to load the guidewire axially and the other for the guidewire to exit radially. The tip of the catheter may be optically transparent in the visible to infrared light spectra. The catheter is configured to be attached to an imaging console and a sled assembly to perform OCT.

The method includes obtaining one or more images using an OCT imaging device at one or more locations along a length of the catheter. The method additionally includes detecting a location of a fixed and constantly present landmark or feature, such as an indicator lumen or an eccentric edge of the catheter body, relative to a center of the OCT imaging device. The method also includes applying a template including an off-ramp indicator over the one or more images. The off-ramp indicator is a two-dimension graphics or a three-dimensional augmented graphics. The off-ramp indicator appears as opaque or translucent on the one or more images.

Some embodiments also relate generally to image processing, and more specifically to methods and apparatus for correction of non-uniform rotational distortion in catheter-based imaging systems.

There is a need to provide a solution to visualize the cross-sectional view of an anatomical lumen or cavity while traversing it with clear interpretation of the surrounding anatomical structures and tissues. Accurate imaging and positioning of the imaging system can help to accurately orient an interventional tool that the operator can steer to stay within the desired pathway to a target location and/or to avoid critical structures that may be damaged during a diagnostic or therapeutic procedure.

In one example, a computer-based method of correcting for image distortion in eccentric rotational imaging catheter systems is provided, which utilizes sinusoidal variations in the catheter wall to delete distortion in the final image.

In one example, a system for imaging a lumen is provided, comprising an imaging catheter, the imaging catheter comprising a tubular body, the tubular body comprising a proximal end region, a distal end region, and a middle region, an imaging lumen located along the proximal, middle and distal regions, a common guidewire lumen located along the proximal, middle and distal regions, a side ramp lumen located in the distal end region and connected to the common guidewire lumen, and comprising a distal opening in a sidewall of the tubular body, a distal guidewire lumen, located in the distal end region and connected to the common guidewire lumen, and comprising a distal opening at an endwall of the tubular body, at least one guidewire bias structure, the at least one guidewire bias structure selected from a group consisting of a reduced diameter region at a junction of the distal guidewire lumen and the common guidewire lumen, an offset distance between a longitudinal axis of the common guidewire lumen and a longitudinal axis of the distal guidewire lumen, an angled flap at or proximal to a junction of the distal guidewire lumen and the common guidewire lumen, a guidewire lumen bump at or proximal to the junction of the distal guidewire lumen and the common guidewire lumen, a proximal catheter assembly, comprising a catheter housing coupled to the proximal end region of the tubular body and a proximal optical connection interface, a first guidewire port in fluid communication with the common guidewire lumen, an imager port in fluid communication with the imaging lumen, and an imaging optical fiber connected to the proximal optical connection interface and extending along the imaging lumen. The system may further comprise a second guidewire port in fluid communication with the common guidewire lumen, wherein the second guidewire port has a different interface than an interface of the first guidewire port. The first and second guidewire ports are located in a hub distal to the catheter assembly. The catheter housing may further comprise an imager actuator engaged to the imaging optical fiber and configured to longitudinally translate the imaging optical fiber relative to the imaging lumen. The system may further comprise a catheter rotation actuator, coupled to the tubular body and configured to rotate the tubular body relative to the proximal catheter housing assembly. The catheter rotation actuator may be rotatably coupled to a distal end of the catheter housing. The proximal catheter assembly may further comprise an optical cable between the catheter housing and the proximal optical connection interface. The proximal optical connection interface may be direct coupled to the catheter housing. The system may further comprise an imaging console, the imaging console comprising a console housing, a power supply, a laser source comprising an output port, a sled interconnection interface, a touchscreen interconnection interface, and a large display interconnection interface. The laser source output port may comprise an imaging port and an aiming beam port. The system may further comprise a sled assembly, the sled assembly comprising a sled housing, a catheter interconnect, a sled power actuator, and a catheter detachment actuator. The catheter interconnect may be a spring-biased catheter interconnect, and the catheter detachment actuator is a catheter ejection actuator. The sled power actuator comprises a light. The system may further comprise a touchscreen with a mounting attachment. The system may further comprise a large non-touchscreen display. The sled housing may comprise a distal cavity configured to receive the catheter housing.

In another example, a method of preparing an imaging catheter is provided, comprising attaching a first sterile drape to a sled assembly, coupling a catheter assembly and a sled assembly, activating the sled assembly, activating an aiming beam of the catheter assembly, deactivating the sled assembly, detaching the catheter assembly from the sled assembly, and enclosing a proximal end of the catheter assembly with a second sterile drape. Attaching the first sterile drape to the sled assembly comprises using an attachment cap to attach the sterile drape to the sled assembly. The method may further comprise cutting a folded corner of the first sterile drape to form a drape opening to be positioned between the sled assembly and the attachment cap.

In another example, a method of using an imaging catheter is provided, comprising advancing an imaging catheter through a guide catheter over a guidewire to a target site, attaching the imaging catheter to a sled assembly, activating the imaging catheter and imaging the target site, using a longitudinal adjustment interface on a proximal housing of the imaging catheter to longitudinally image a ramp lumen of the imaging catheter, advance the imaging catheter toward and around a lesion of the target site, using the imaging catheter to identify a true lumen of the target site, rotating the imaging of the target site using the rotation actuator of the imaging catheter to orient the ramp lumen toward the true lumen of the target site, withdrawing the guidewire from a distal guidewire lumen of the imaging catheter, advancing the guidewire through the ramp lumen of the imaging catheter and into the true lumen of the target site, optionally confirming re-entry of the true lumen, and retracting the imaging catheter while maintaining the position of the guidewire in the true lumen. The method may further comprise using the guidewire to deliver a stent to the target site. The method further comprise activating a ruler overlay of the target site imaging, the ruler overlay depicting distance markings, and measuring a vessel size using the ruler overlay. The method may further comprise turning on a ramp overlay of the target site imaging, the ramp overlay depicting guidewire directional markings on the target site imaging. The method may further comprise flushing the imaging catheter using a guidewire flush port of the imaging catheter. Confirming re-entry of the true lumen may be confirmed using fluoroscopy and contrast dye. The method may further comprise pre-coupling the catheter assembly and the sled assembly, activating the sled assembly. The method may further comprise attaching a first sterile drape to the sled assembly. The method may further comprise activating an aiming beam of the catheter assembly, and deactivating the sled assembly. The method may further comprise detaching the catheter assembly from the sled assembly, and enclosing a proximal end of the catheter assembly with a second sterile drape. Attaching the first sterile drape to the sled assembly may comprise using an attachment cap to attach the sterile drape to the sled assembly. The method may further comprise cutting a folded corner of the first sterile drape to form a drape opening to be positioned between the sled assembly and the attachment cap.

An image-guided interventional catheter, comprising a housing including a distal catheter region, the distal catheter region including a imaging body and a catheter body, the distal catheter region defining an imaging lumen configured to receive an imaging device, a guidewire lumen configured to receive a guidewire, the guidewire lumen including a distal section, a proximal section, and one or more guidewire feeders, the one or more guidewire feeders including at least one of a bump in the proximal section near an intersection of the distal section and the proximal section, the distal section including a tapered region, a maximum lateral dimension of the tapered region increasing with increasing distance from the intersection, a center of the distal section offset relative to a center of the proximal section, or the intersection of the distal section and the proximal section includes a thin, pierceable wall, an off-ramp extending from the guidewire lumen at or near the intersection of the distal section and the proximal section of the guidewire lumen, one or more guidewire feeders configured to cause the guidewire to extend from the guidewire lumen into the off-ramp, and an indicator lumen configured to receive an indicator that is detectable by the optical coherence tomography imaging device. The imaging device may include an optical coherence tomography imaging device. One or more guidewire feeders may include the bump. The one or more guidewire feeders may include the distal section including the tapered region. The tapered region may extend from the intersection of the distal section and the proximal section. One or more guidewire feeders may include the center of the distal section offset relative to the center of the proximal section. The one or more guidewire feeders may include the intersection of the distal section and the proximal section including a thin, pierceable wall. The one or more guidewire feeders further may include a ramp at the intersection of the distal section and the proximal section. The distal catheter region may include one or more detectable structures indicating distance from a distal tip of the distal catheter region, the one or more detectable structures detectable by the imaging device. The one or more detectable structures may include an annular or semi-annular base and one or more elongated arms extending from the annular or semi-annular base, wherein at least the one or more longitudinal arms are detectable by the imaging device. The one or more longitudinal arms may include a plurality of longitudinal elements, the length of at least some of the plurality of longitudinal elements are different. The one or more detectable structures may include one or more holes formed in the housing of the distal catheter region. In some variations, a system comprising the described catheter above is provided, wherein the housing includes the proximal catheter region, a housing attached to the catheter, the housing including one or more actuators configured to at least one of rotate at least a portion of the catheter relative to the housing, or move the imaging device in the imaging lumen. The system may further comprise a display and a graphical user interface, the graphical user interface configured to show an image detected by the imaging device on the display, the graphical user interface including at least one icon that applies a template on image shown on the display. The template may include an off-ramp indicator indicating a direction that the off-ramp extends from the guidewire lumen.

In another example, a method to determine an orientation of a catheter is provided, the method comprising obtaining one or more images using an optical coherence tomography imaging device at one or more locations along a length of the catheter, excluding data from the one or more images, detecting an orbital of the catheter, detecting a location of a fixed and constantly present landmark or feature of the catheter relative to a center of the optical coherence tomography imaging device, applying a template including an off-ramp indicator over the one or more images, wherein the off-ramp indicator includes a two-dimension graphic or a three-dimensional augmented graphic, the off-ramp appearing as opaque or translucent on the one or more images. Detecting an orbital of the catheter may include detecting the orbital within a catheter edge detection range from an edge of the one or more images. The fixed and constantly present landmark feature of the catheter may include an indicator lumen. Detecting a location of a fixed and constantly present landmark or feature of the catheter relative to a center of the optical coherence tomography imaging device may include at least one of detecting the indicator lumen within a lumen detection range from an edge of the one or more images, or detecting the indicator lumen within indicator lumen angle range, wherein the indicator lumen angle range is spaced from the detected orbital by an angle offset. The template may include an indicator circle disposed over an indicator lumen.

In another example, a non-transitory computer-readable medium storing an image correction program causing a computer device comprising a storage medium to execute functions is provided, comprising receiving a frame of sequential images generated by an eccentric imaging catheter, identifying an imaged wall location in a sequential image from the period of sequential images, and modifying the period of sequential images by conforming the imaged wall location of the sequential image to a reference wall location of the period of sequential images. Modifying the period of sequential images may comprise deleting intervening sequential images between the sequential image and the reference wall location. The reference wall location may be from a sequence of reference wall locations corresponding to a reference sinusoidal pattern of wall locations. The reference sinusoidal pattern of wall locations may be derived from a geometric model of the eccentric imaging catheter. The reference sinusoidal pattern of wall locations may be determined by a calibration procedure of the eccentric imaging catheter. The frame may be selected from a series of sequential images generated by the eccentric imaging catheter. The frame of sequential images may correspond to a 360 degree rotation of the eccentric imaging catheter, or a fixed number of sequential images. The non-transitory computer-readable medium may further comprise downsampling the series or period of sequential images. Downsampling may comprise deletion of sequential images from the series or period of sequential images. A ratio of deleted sequential images to non-deleted sequential images may be greater than or equal to 20:1. Downsampling may comprise cropping each of the sequential images from the series or period of sequential images a fixed number of pixels or distance from an imager origin end of each of the sequential images. The non-transitory computer-readable medium may further comprise extrapolating at least one replacement sequential image from at least some of the deleted sequential images, wherein the at least one replacement sequential image is fewer in number than the number of deleted sequential images.

In another example, a non-transitory computer-readable medium storing an image correction program causing a computer device comprising a storage medium to execute functions is provided, comprising receiving a frame of sequential images generated by a variable wall distance imaging catheter, identifying an imaged wall location in a sequential image from the period of sequential images, and modifying the period of sequential images by conforming the imaged wall location of the sequential image to a reference wall location of the period of sequential images. The variable wall distance imaging catheter may be an eccentric imaging catheter. The variable wall distance imaging catheter may be a concentric non-circular imaging catheter.

In another example, an imaging processing system for executing an image processing function is provided, comprising a receiving unit configured to receive a frame of sequential images generated by an eccentric imaging catheter, an identification unit configured to identify an imaged wall location in a sequential image from the period of sequential images, and a modification unit configured to modify the period of sequential images by conforming the imaged wall location of the sequential image to a reference wall location of the period of sequential images.

In still another example, an image processing method is provided, comprising receiving a frame of sequential images generated by an eccentric imaging catheter, identifying an imaged wall location in a sequential image from the period of sequential images, and modifying the period of sequential images by conforming the imaged wall location of the sequential image to a reference wall location of the period of sequential images.

In another example, a re-entry catheter system is provided, comprising an elongate catheter body, the catheter body comprising a proximal end, a distal end, a common lumen extending from the proximal location at the proximal end to a distal location proximal to the distal end, comprising a first longitudinal central axis, a distal lumen extending from the distal location of the common lumen to the distal end of the catheter body, wherein the distal lumen has comprise a second longitudinal central axis that is parallel and offset from the first longitudinal central axis, and a side lumen extending distally from the distal location of the common lumen to a side wall location of the catheter body wherein the side wall location is proximal to the distal end of the catheter body, an imaging lumen extending from the proximal end of the catheter body, a proximal catheter handle coupled to the proximal end of the catheter body, the handle comprising a catheter body rotator knob configured to rotate the catheter body relative to the proximal catheter handle, and an imaging catheter displacement knob configured to longitudinally displace an imaging catheter inserted into the catheter body relative to the catheter body. The side wall location of the side lumen may be located proximal to a closed distal end of the imaging lumen. The distal end of the catheter body may be an asymmetrically tapered cone shape. The catheter body may further comprises an indicator lumen. The average diameter of the indicator lumen may be smaller than the average diameter of the distal lumen, which is smaller than the average diameter of the common lumen, which is smaller than the average diameter of the imaging lumen.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIGS. 2-6B are cross-sectional views of catheters having different guidewire feeders, according to different environments.

DETAILED DESCRIPTION

Figure 1A:
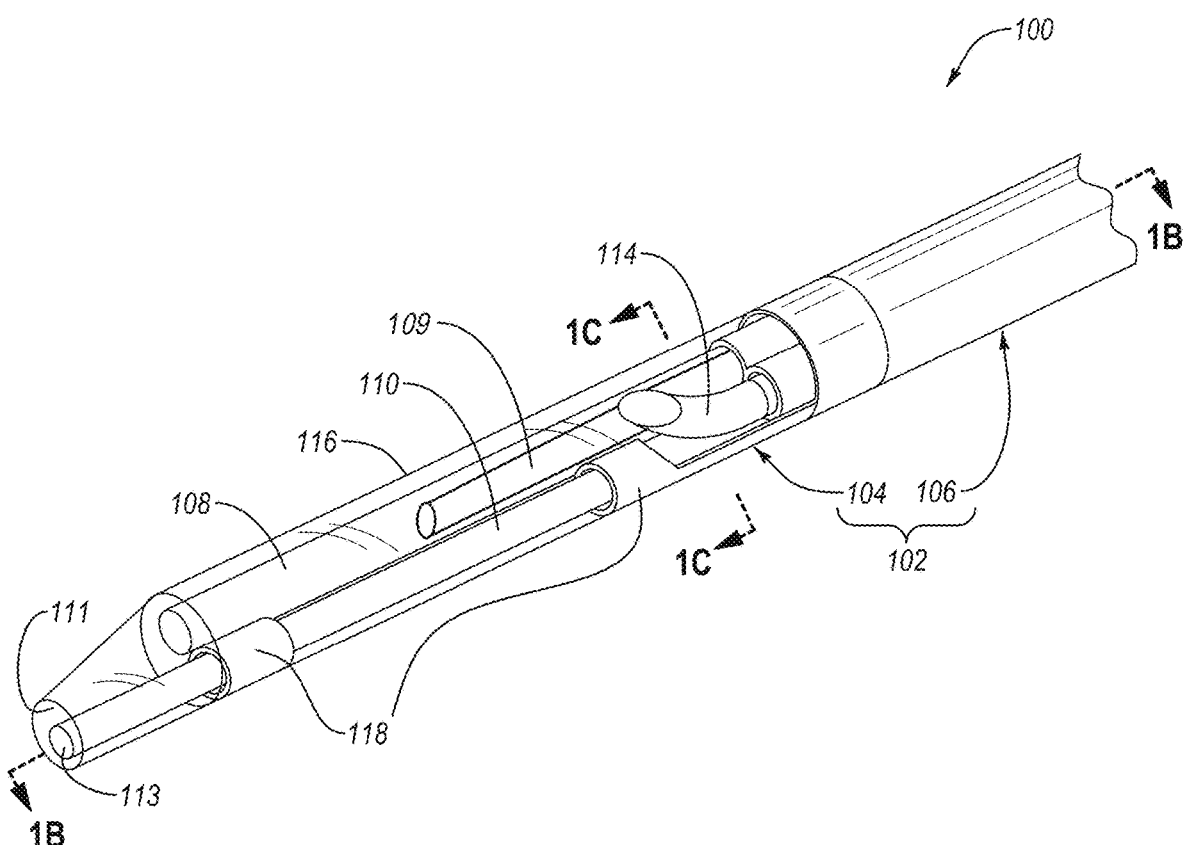
FIG. 1A is an isometric view of a portion of a catheter, according to an embodiment.

Embodiments are directed to systems, devices, and method for antegrade dissection and reentry. Such systems, devices, and methods may include an image guided interventional catheters ("catheter"), systems including the same, and method of using the same. An example catheter includes a housing having the distal catheter region configured to be at least partially disposed in a body and the proximal catheter region configured to remain at least partially outside of the body. The distal catheter region includes an imaging body and a catheter body. The distal catheter region defines a plurality of lumens. The plurality of lumens may include an imaging lumen, a guidewire lumen, an off-ramp, and an indicator lumen. The imaging lumen is configured to receive an imaging device (e.g., an optical coherence tomography imaging device). The guidewire lumen is configured to receive a guidewire and includes a distal region and a proximal region. The off-ramp extends from the guidewire lumen at or near an intersection of the distal and proximal regions of the guidewire lumen. The indicator lumen is configured to receive an indicator that is detectable by the imaging device and software algorithm. The catheter may also include one or more guidewire feeders. The guidewire feeders are configured to cause the guidewire to move from the proximal section to the off-ramp. Examples of the guidewire feeders may include a bump, the distal section including a tapered region, the centers of a distal section and a proximal section of the guidewire lumen are offset, or the intersection of the distal section and the proximal section includes a thin, pierceable wall.

The catheter may be used to guide the guidewire in a body. For example, the distal end of the guidewire may be inserted into the body. The lumen in which the guidewire is disposed may be blocked (e.g., due to chronic total occlusion) and/or may branch into one or more additional lumens (e.g., a true lumen). In such situations, a proximal end of the guidewire may be disposed through an opening formed on the distal catheter region of the catheter and into the guidewire lumen. The catheter may be moved along the guidewire and into the body until the catheter is at a desired location (e.g., at the blocked portion of the lumen or at the location from which the additional lumens branch). At this point, the guidewire is disposed in both the distal and proximal regions of the guidewire lumen. Once the catheter is at the desired location, the guidewire may be retracted into the catheter until the guidewire is no longer in the distal region of the catheter. The guidewire may then be advanced in the catheter which causes the the distal guidewire tip to interact with the guidewire feeder. The interaction between the guidewire and the guidewire feeder causes the guidewire to move into the off-ramp instead of back into the distal section of the guidewire lumen. The guidewire may exit the catheter via the off-ramp at an angle relative to the catheter that is different than if the guidewire exited the catheter via distal section of the guidewire lumen.

During use, it may be difficult to determine the orientation of the off-ramp relative to the body. The orientation of the off-ramp may need to be known to prevent the guidewire exiting the off-ramp from puncturing a lumen of the body or blood vessel, or moving in the wrong direction. The imaging device in conjunction with other elements of the catheter may be used to determine the orientation of the off-ramp at any given time. For example, a system including the catheter may be able to detect one or more elements (e.g., the indicator disposed in the indicator lumen) of the catheter. The orientation of the off-ramp may then be determined based on the known positional relationship between the imaging device, the one or more detected elements, and the known positional relationship between the imaging device, the detected elements, and the off-ramp.

Figure 1B:
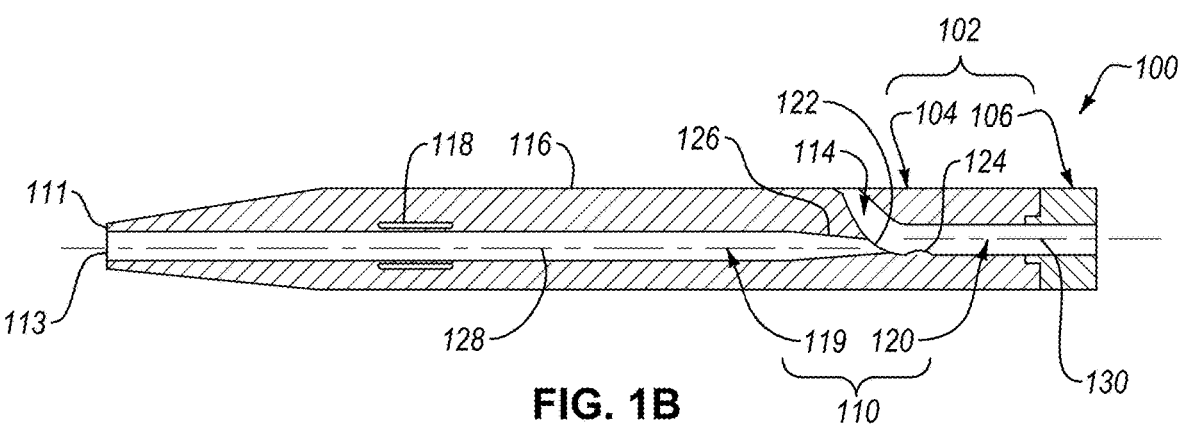
FIGS. 1B and 1C are cross-sectional views of the catheter taken along planes 1B-1B and 1C-1C, respectively, as shown in FIG. 1A.
Figure 1C:
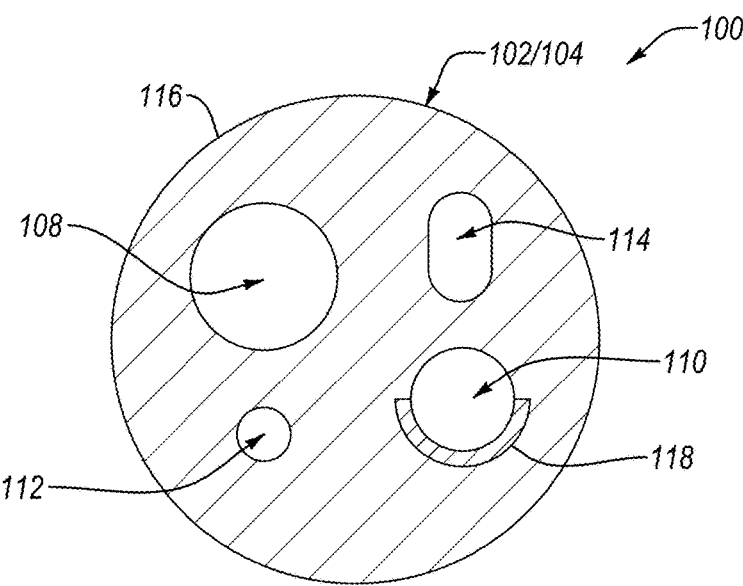

FIG. 1A is an isometric view of a portion of a catheter 100, according to an embodiment. FIGS. 1B and 1C are cross-sectional views of the catheter 100 taken along planes 1B-1B and 1C-1C, respectively, as shown in FIG. 1A. The catheter 100 includes a housing 102. The housing 102 includes a distal catheter region (a portion of which shown in FIG. 1A) and the proximal catheter region (shown in FIG. 16A). The distal catheter region includes at least a portion of the housing 102 that is disposed in the body while the proximal catheter region includes at least a portion of the housing 102 that is not disposed in the body. For illustrative purposes, the distal catheter region of the housing 102 includes an imaging body 104 which facilitates imaging of structures and/or tissues surrounding the catheter 100 and a catheter body 106. The imaging body 104 may comprise a material that is at least partially transparent (e.g., at least partially optically transparent) to the stimulus emitted and/or detected by the imaging device 109 (e.g. optical coherence tomography imaging device ("OCT") or ultrasound), to reduce imaging opacity with respect to the imaging device 109. The catheter body 106 may be opaque with respect to the imaging device 109. However, it is noted that imaging body 104 may be opaque and/or the catheter body 106 may be at least partially transparent to the imaging device 109. The imaging body 104 may be integrally formed with or distinct from the catheter body 106.

In some examples, the catheter 100 is an over-the-wire support catheter or extender catheter to aid in the placement and positioning of a guidewire in the blood vessel. In another example, the catheter 100 is an over-the-wire OCT guided support catheter or extender catheter to facilitate the placement and positioning of a guidewire with realtime visualization in the blood vessel. In some examples, catheter 100 is an over-the-wire OCT guided re-entry catheter, which may be used with a guidewire. The catheter 100 may be 2.5 F, 3F, 4 F, 5F, 6 F, 7 F 8 F, 9 F or 10 F, a length in the range of 50 to 130 cm, 90 to 130 cm, 90 to 110 cm, 50 to 135 cm, or 90 to 135 cm, may optionally comprise a hydrophilic coating, with or without a radiopaque tip, with or without an inflatable or collapsible balloon at the distal end of the catheter 104 on the opposing side of the off ramp exit 114, and may be straight or angled. The balloon may be at least partially transparent to the imaging device 109.

The housing 102 of the catheter 100 may define a plurality of lumens. For example, the housing 102 may define an imaging lumen 108, a guidewire lumen 110, an indicator lumen 112 (FIGS. 1C and 8A), and an off-ramp 114. One or more of the imaging lumen 108, the guidewire lumen 110, or the indicator lumen 112 may extend generally parallel to a longitudinal axis of the catheter 100. Meanwhile, the off-ramp 114 is a lumen extending from the guidewire lumen 110 to a lateral edge 116 of the housing 102. In other words, at least a portion of the off-ramp 114 extends at a non-parallel angle relative to a longitudinal axis of the catheter 100.

The imaging lumen 108 may be configured to receive the imaging device 109 (shown in FIG. 1A). The imaging device 109 may include any suitable device that may image the catheter 100 and/or the environment thereabout (e.g., an artery). In an example, the imaging device 109 may include at least one of an OCT, an ultrasound transceiver, or another imaging device. The imaging lumen 108 may extend into the imaging body 104 of the housing 102 thereby allowing the imaging device 109 to image the environment about the catheter 100.

The guidewire lumen 110 may be configured to receive a guidewire (not shown). The guidewire lumen 110 may extend to a distal end 111 of the housing 102 and form an opening 113 in the housing 102 thereby allowing the guidewire to extend out of the catheter 100. The guidewire lumen 100 includes a distal section 119 and a proximal section 120 (FIG. 1B). The distal section 119 extends from the distal end 111 of the housing 102 to the proximal section 120. The proximal section 120 extends from the distal section 119 towards (e.g., to) the proximal catheter region. In an embodiment, all of or most of (e.g., 80% or more or 90% or more of a length of) the distal section 119 is within the imaging body 104 of the housing 102 and all of or most of (e.g., 90% or more or 95% or more of a length of) the proximal section 120 is within the catheter body 106. In such an embodiment, an intersection 122 of the distal section 119 and the proximal section 120 is at or near the intersection of the image body 104 and the catheter body 106. Disposing all of or most of the distal section 119 in the imaging body 104 allows the off-ramp 114 and the environment into which the off-ramp positions the guidewire to be imaged by the imaging device 109.

In some examples, the catheter 100 may be an over-the-wire OCT guided re-entry catheter, which may be used with a guiding catheter and guidewire. In such example, the guidewire lumen 110 may be configured to receive a guidewire. The guidewire may be a 0.014" guidewire, but in some other variations may be a 0.009" or 0.010" with or without a tapered tip. The guidewire may comprise a hydrophobic or a hydrophilic coating at more or more regions, and may have a length in the range of 150 to 300 cm, 150 to 200 cm.

The indicator lumen 112 may be configured to receive a material that may be detectable by the imaging device 109. In a particular example, the material received by the indicator lumen 112 may be more easily detectable by the imaging device 109 than the guidewire and/or the imaging body 104. For instance, the material received by the indicator lumen 112 may be more opaque or more reflective of the stimulus emitted and/or detected by the imaging device 109 than the guidewire and/or the imaging body 104. Additionally or alternatively, the indicator lumen 112 may provide material discontinuity or interfaces between the medium inside the lumen and its surrounding, resulting in difference in optical refractive indices and partial reflection, of which its interference signal is detectable by the imaging device 109 and used as a fixed landmark. In an embodiment, the indicator lumen 112 may also be used for other functions, including but not limited to the flushing blood to improve imaging clarity or injecting diagnostic or therapeutic agents into the surrounding tissue. In such an embodiment, the indicator lumen 112 may also form an opening (not shown) in the housing 102 through which the flushing fluid and/or diagnostic or therapeutic agents may be dispensed from the housing 102.

As previously discussed, the off-ramp 114 extends from the guidewire lumen 110 to a lateral edge 116 of the housing 102 (e.g., a lateral edge of the imaging body 104). As such, diverting the guidewire into the off-ramp 114 from the guidewire lumen 110 causes the guidewire to extend an angle relative to the longitudinal axis the catheter 100. The off-ramp 114 may extend from the guidewire lumen 110 at a location at or near the intersection 122 between the distal section 119 and the proximal section 120. Such a location of the off-ramp 114 allows the guidewire to be diverted into off-ramp 114 when the guidewire is retracted from the distal section 119. The off-ramp 114 may extend at an angle that is about 10° to about 45° relative to a central axis of the guidewire lumen 100, such as in ranges of about 10° to about 20°, about 15° to about 25°, about 20° to about 30°, about 25° to about 35°, about 30° to about 40°, or about 35° to about 45°.

The guidewire lumen 110 and the off-ramp 114 are configured to receive a guidewire. As such, the guidewire lumen 10 and the off-ramp 114 exhibit a cross-sectional size (e.g., a diameter or other maximum lateral dimension) that is sufficiently large to receive the guidewire. In an embodiment, at least a portion of the guidewire lumen 110 extending from the distal end 111 and the portion of the off-ramp 114 extending from the intersection 122 exhibit a cross-sectional size that is significantly larger (e.g., up to 5%, 10%, 20%, 25%, 50%, 75%, 100%, 150%, or 200% larger) than the cross-sectional size of the guidewire. The significantly larger cross-sectional size of the guidewire lumen 110 and the off-ramp 114 facilitates insertion of the guidewire into the guidewire lumen 110 and the off-ramp 114. Further, cross-sectional size of the guidewire lumen 110 and/or the off-ramp 114 may decrease along at least a portion of the length thereof. For example, the cross-sectional size of the guidewire lumen 110 may decrease at a location spaced from the distal end 111 and/or proximate to the intersection 122, and/or at the off-ramp 114 exit. As will be discussed in more detail below, the decrease cross-sectional size of the guidewire lumen 110 may facilitate redirecting guidewire from the guidewire lumen 110 (e.g., the proximal section 120) into the off-ramp 114. The decreased cross-sectional size of guidewire lumen 110 and or the off-ramp 114 also decreases movement of the guidewire therein and minimizes backflow of a fluid from the body into a guidewire lumen 110.

During use, the guidewire may be inserted into a lumen of a body, such as an artery in human body. In some instances, the lumen of the body may be obstructed, for example, by plaque or atherosclerotic plaque. Generally, the guidewire may be used to move, break-up, or otherwise remove the obstruction. In an embodiment, the guidewire may be unable to move, break-up, or otherwise remove the obstruction, such as when the obstruction is caused by chronic total occlusion. When the guidewire meets the obstruction that cannot be moved, broken-up, or otherwise removed, the guidewire may be disposed in the guidewire lumen 110 (if not already positioned in the guidewire lumen 110) thereby allowing the guidewire to guide the catheter 100 through the body. When the catheter 100 is at or near the obstruction that cannot be moved, broken-up, or otherwise removed, the guidewire may be retracted into the guidewire lumen 110 until a distal tip of the guidewire is spaced further from the distal end 111 of the catheter 100 than an inlet of the off-ramp 114 (i.e., the opening of the off-ramp 114 adjacent to the guidewire lumen 110). For example, the distal tip of the guidewire may be retracted until the distal tip of the guidewire is positioned proximal to a bifurcating junction between the guidewire lumen 110 and the off-ramp 114. The guidewire may then be advanced into the off-ramp 114. Advancing the guidewire into the off-ramp 114 changes the direction that the guidewire extends thereby allowing the guidewire to go around or through the obstruction in the direction of the true lumen which, in turn, allows the catheter 100 to go around the obstruction. For example, after the guidewire extends out of the off-ramp 114, the catheter 100 may be remove and, with the guidewire back-loaded into the catheter 100 at the distal tip 111, the catheter 100 is re-inserted into the lumen and follows the guidewire to go around the obstruction.

As previously discussed, the catheter 100 may include one or more guidewire feeders. The guidewire feeders are configured to redirect the guidewire in the proximal section 120 towards the off-ramp 114 instead of the distal section 119 when the guidewire is advanced from the proximal section 120 towards the distal section 119. The catheter 100 may include any number of guidewire feeders, such as in one guidewire feeder, two guidewire feeders, three guidewire feeders, four guidewire feeders, or five or more guidewire feeders. In the embodiment illustrated in FIG. 1B, the catheter 100 includes three guidewire feeders. However, it is noted that the catheter 100 may include guidewire feeders other than or in addition to the guidewire feeders illustrated in FIG. 1B.

In an embodiment, the guidewire feeders may include a bump 124. The bump 124 is a protrusion that extends from the housing 102 into the guidewire lumen 110. The bump 124 may exhibit any suitable shape, such as a portion of a generally spherical shape, a generally cylindrical shape, or a wedge-like shape. The bump 124 may be located at the intersection 122 or in the proximal section 120 location that is slightly spaced from the intersection 122 (e.g., about 5 mm or less, about 3 mm or less, or about 1 mm or less). The bump 124 may be opposite the inlet to the off-ramp 114. The bump 124 may form an obstacle that causes the guidewire to be diverted into the off-ramp 114 instead of the distal section 119. For example, as previously discussed, the guidewire may be retracted into the catheter 100 until the guidewire is no longer disposed in the distal section 119 or, in other words, until a distal tip of the guidewire is disposed in proximal section 120. Advancing the guidewire towards the distal tip 111 causes the distal tip of the guidewire to contact the bump 124. Contacting the guidewire against the bump 124 diverts the guidewire towards the off-ramp 114 instead of the distal section 119. The bump 124 may be improvement over the conventional means for diverting the guidewire between two passageways. For example, the bump 124 does not need to move to divert the guidewire thus avoiding issues associated with at least some conventional means for diverting the guidewire, such as the conventional means breaking or becoming stuck.

In an embodiment, the guidewire feeders may include a tapered region 126 formed in the distal section 119. The tapered section 126 includes region of the distal section 120 wherein a lateral dimension (e.g., a diameter) of the distal section 119 decreases. The lateral dimension of the tapered section 126 may decrease with increasing proximity to the intersection 122. The tapered section 126 may decrease the lateral dimension of the distal section 119 until the lateral dimension of the distal section 119 is only slightly larger than the lateral dimension of the guidewire. The tapered section 126 may be spaced from the distal tip 111 such that the decreased lateral dimension of the tapered section 127 does not inhibit inserting the guidewire into the guidewire lumen 110. For example, as shown, the tapered region 126 may extend from or near the intersection 122. The tapered region 126 decreases the lateral dimension of the distal section 119 at the intersection 120 such that the lateral dimension of the distal section 119 is less than a lateral dimension of the inlet of the off-ramp 114. The decreased lateral dimension of the distal section 119 at the intersection 122 relative to the lateral dimension of the inlet the off-ramp 114 decreases the likelihood advancing the guidewire causes the guidewire to enter the distal section 119 and increases the likelihood advancing the guidewire causes the guidewire to enter the off-ramp 114. Again, the tapered region 126 may be improvement over the conventional means for diverting the guidewire between two passageways since the tapered region 126 does not need to move to divert the guidewire. Also, as previously discussed, the decreased lateral dimension of the guidewire lumen 110 caused by the tapered region 126 inhibits fluids flowing up the guidewire lumen 110.

In an embodiment, the guidewire feeders includes offsetting the distal and proximal sections 119, 120 relative to each other. For example, the distal section 119 may exhibit a distal central axis 128 and the proximal section 120 may exhibit proximal central axis 130. The distal central axis 128 may be offset relative to the proximal central axis 130. In other words, the distal central axis 128 and the proximal central axis 130 are not aligned. The distal and proximal central axes 128, 130 may be positioned such that the proximal central axis 130 is closer to the off-ramp 114 than the distal central axis 128. The offset between the distal and proximal axes 128, 130 increases the likelihood that advancing the guidewire from the proximal section towards the distal tip 111 causes the guidewire to enter the off-ramp 114 instead of the distal section 119.

The catheter 100 may include one or more additional features, such as a reinforcement structure 118 that strengthens the guidewire lumen 110 or another portion of the catheter 100. The catheter 100 may also include a helical reinforcement or side slotted tube.

The catheters disclosed herein may include guidewire feeders other than the guidewire feeders shown in FIG. 1B. FIGS. 2-6B are cross-sectional views of catheters having different guidewire feeders, according to different environments. Except as otherwise disclosed here, the catheter shown in FIGS. 2-6B may be the same as or substantially similar to any of the catheters disclosed herein. For example, the catheters may include a housing that defines a plurality of lumens. The plurality of the lumens may include a guidewire lumen and an off-ramp. The guidewire lumen may include a distal section and proximal section. It is noted that the guidewire feeders illustrated in FIGS. 2-6B may be used in any of the catheter embodiments disclosed herein. Further, it is noted that any of the guidewire feeders illustrated in FIGS. 2-6B may be used in conjunction with one or more of any other guidewire feeders disclosed herein.

Figure 2:
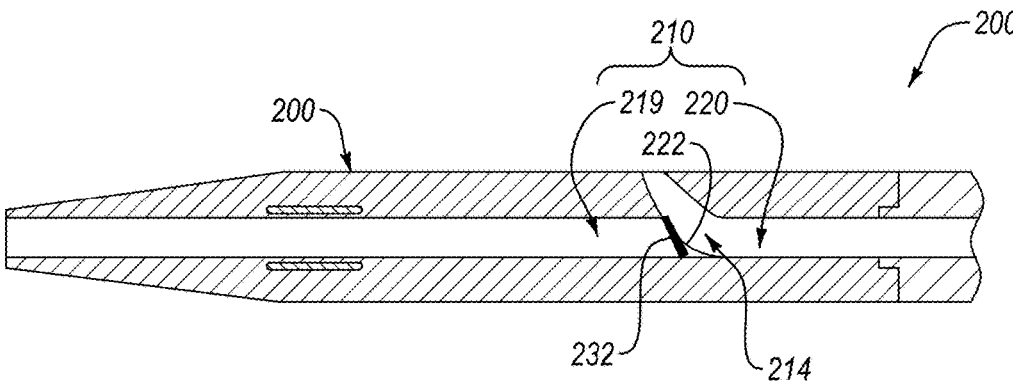

Referring to FIG. 2, the guidewire feeder of the catheter 200 may include a thin, pierceable wall ("thin wall") 232. The thin wall 232 may be positioned at or near the intersection 222 of the distal section 219 and the proximal section 220 of the guidewire lumen 210. The thin wall 232 is configured to be pierceable by the guidewire to form a hole therein. The hole formed in the thin wall 232 may exhibit a size that corresponds to the size of the guidewire. In other words, piercing the thin wall 232 with the guidewire cause the thin wall 232 to exhibit as hole that may be as small as possible to fit the guidewire therethrough. The small size of the hole decreases the likelihood that advancing the guidewire towards the distal tip 211 from the proximal section 220 causes the guidewire move back through the thin wall 232.

The thin wall 232 may be formed from any suitable material. In an example, the thin wall 232 may be formed from the same material as the portion of the housing 202 that defines the intersection 222 which may facilitate manufacturing of the thin wall 232 than if the thin wall 232 was formed from a material that is different than the portion of the housing 222 that defines the intersection 222. In an example, the thin wall 232 be formed from a material that is different than the portion of the housing 202 that forms the intersection 222 may allow the thin wall 232 to be formed from a material that is at least one of more easily pierceable, stronger, more easily manufactured as a thin film, or otherwise more beneficial than the material that forms a housing 202.

In an embodiment, the thin wall 232 exhibits a minimum thickness measured parallel to one or more central axes of the guidewire lumen 210 that is about 1 μm or greater, about 5 μm or greater, about 10 μm or greater, about 25 μm or greater, about 50 μm or greater, about 100 μm greater, about 150 μm or greater, about 200 μm or greater, about 300 μm or greater, about 400 μm or greater, about 500 μm or greater, about 600 µm or greater, about 700 µm or greater, about 800 µm or greater, about 1 mm or greater, about 1.25 mm or greater, about 1.5 mm or greater, about 2 mm or greater, or in ranges of about 1 µm to about 10 µm, about 5 µm to about 25 µm, about 10 µm to about 50 µm, about 25 µm to about 100 µm, about 50 µm to about 150 µm, about 100 µm to about 200 µm, about 150 µm to about 300 µm, about 200 µm to about 400 µm, about 300 µm to about 500 µm, about 400 µm to about 600 µm, about 500 µm to about 700 µm, about 600 µm to about 800 µm, about 700 µm to about 900 µm, about 800 µm to about 1 mm, about 900 µm to about 1.25 mm, about 1 mm to about 1.5 mm, or about 1.25 mm to about 2.

The thin wall 232 is configured to be easily pierceable. Whether the thin wall 232 is easily pierceable depends on the material forming the thin wall 232 and the minimum thickness of the thin wall 232. In an embodiment, the thin wall 232 does not include a hole therein. In such an embodiment, a device (e.g., a needle or probe) may be inserted into the guidewire lumen 210 via the proximal or distal guidewire lumen. The device inserted into the guidewire lumen 210 may puncture or otherwise pierce the thin wall 232 to form a small hole therein. The small hole may exhibit a lateral dimension (e.g., a diameter) that is substantially equal to or, more preferably, smaller than the lateral dimension of the guidewire. The device may then be removed from the guidewire lumen 210 and the guidewire may then be inserted into the guidewire lumen 210. The guidewire may extend through the small hole formed in the thin wall 232. After extending the guidewire through the small hole, the small hole exhibits a lateral dimension that is substantially similar to the lateral dimension of the guidewire. In an embodiment, the thin wall 232 includes a small hole formed therein prior to use. In such an embodiment, the thin wall 232 does not need to be pierced by the device. However, forming the small hole in the thin wall 232 before use may prevent the catheter 200 from being used with a guidewire exhibiting a lateral dimension that is smaller than the lateral dimension of the small hole. In an embodiment, the thin wall 232 does not include a hole formed therein. In such an embodiment, the guidewire itself may be used to form a small hole in the thin wall 232 instead of using the device to form the hole prior to insertion of the guidewire.

Figures 3A, 3B, 4, 5A, 5B:
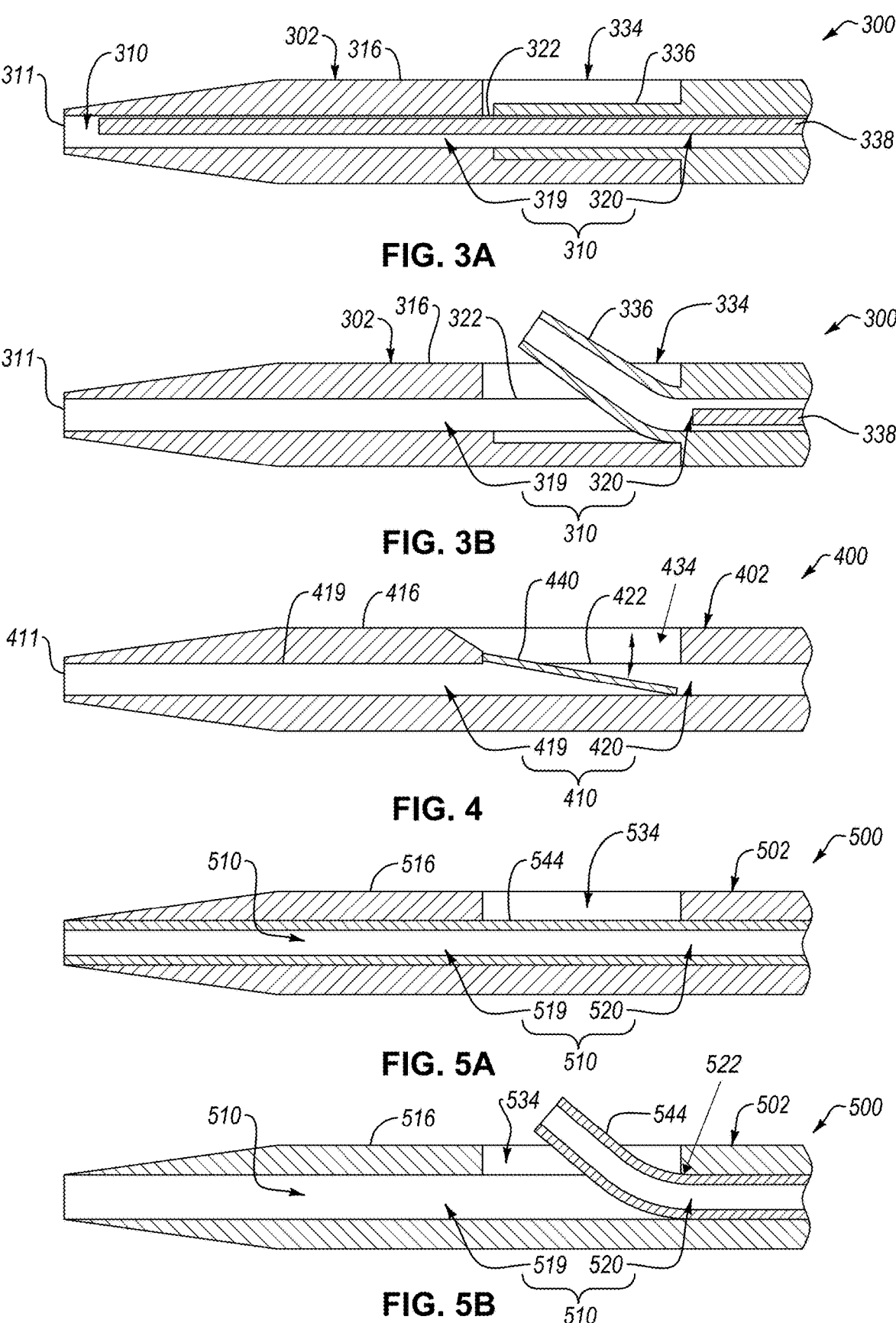

Referring to FIGS. 3A and 3B, the catheter 300 includes a housing 302. The housing 302 defines a guidewire lumen 310 including the distal section 319 and the proximal section 320. The housing 302 defines a lateral opening 334 extending from a lateral edge 316 to the guidewire lumen 310 at the intersection 322 of the distal and proximal sections 319, 320. The housing 302 also includes a biased section 336 exhibiting a tubular shape extending partially across the lateral opening 334. In other words, the biased section 336 forms the intersection 322. When unrestricted, the biased section 336 exhibits curved shape that allows the biased section 336 to extend through the lateral opening 334. As shown in FIG. 3A, the portion of the guidewire lumen 310 defined by the biased section 336 may be forced to be aligned with the distal and proximal sections 319, 320 of the guidewire lumen 310 when a guidewire 338 is disposed in the proximal and distal sections 319, 320 of the guidewire lumen 310. As shown in FIG. 3B, retracting the guidewire 338 from the proximal section 319 allows the biased section 336 exhibit a curved shape thereof which, in turn, allows the biased section 336 to form the off-ramp of the catheter 300. Advancing the guidewire 338 towards the distal tip 311 causes the guidewire 338 to follow the curved shape of the distal section 336. The curved shape of 336 may extend at an angle that is about 10° to about 45° relative to a central axis of the guidewire lumen 310, such as in ranges of about 10° to about 20°, about 15° to about 25°, about 20° to about 30°, about 25° to about 35°, about 30° to about 40°, or about 35° to about 45°.

Referring to FIG. 4, the catheter 400 includes a housing 402. The housing 402 defines the guidewire lumen 410 including the distal section 419 and the proximal section 420. The housing defines a lateral opening 434 extending from a lateral edge 416 to the guidewire lumen 410 at the intersection of the distal and proximal sections 419, 420. The catheter 400 also includes a ramp 440 extending at least partially across the lateral opening 434. The ramp 440 may be distinct from the housing 402 (e.g., the housing 402 may be formed from a polymer and/or the ramp 440 may be formed from nitinol) or maybe integrally formed with the housing 402 (e.g., the housing 402 and ramp 440 may be formed from the same material and exhibit single piece construction). The ramp 440 may be configured to rotate or bend at or near a location where the ramp 440 meets the housing 402. The ramp 440 may switch between a first state and a second state. The ramp 440 may extend generally parallel to a central axis of the guidewire lumen 410 when the ramp 440 is in the first state. The ramp 440 may exhibit the first state when a guidewire (not shown) is positioned in the distal and proximal sections 419, 420. Removing the guidewire from the distal section 419 allows the ramp 440 to move towards a surface of the guidewire lumen 410 that is opposite the lateral opening 434. The ramp 440 may move towards the opposing surface of the guidewire lumen 410 because the ramp 440 is biased or because of gravity. The ramp 440 is in the second state when the ramp 440 is allowed to move towards the surface of the guidewire lumen 410 that is opposite the lateral opening 434. When the ramp 440 exhibits the second state, advancing the guidewire towards the distal tip 411 causes the guidewire to exit the guidewire lumen 410 at the lateral opening 436. In other words, the ramp 440 forms at least a portion of the off-ramp of the catheter 400. It is noted that the housing 402 may include a tapered surface 442 extending from or near the ramp 440 when the ramp the ramp 440 does not extend to the lateral edge 416 of the housing 402.

Referring to FIGS. 5A and 5B, the catheter 500 includes a housing 502. The housing 502 defines a guidewire lumen 510 including the distal section 519 and the proximal section 520. The housing 502 defines a lateral opening 534 extending from a lateral edge 516 to the guidewire lumen 510 at the intersection 522 of the distal and proximal sections 519, 520. The housing 502 also includes a hypotube 544 disposed in the guidewire lumen 510. The hypotube 544 is movable (e.g., slideable) relative to the guidewire lumen 510. The hypotube 544 is biased such that at least a portion of the hypotube 544 exhibits a curved shape when the hypotube 544 is unrestricted. The hypotube 544 may be switchable between a first state and a second state. When the first state, the hypotube 544 may be positioned in the distal and proximal sections 519, 520 and extend across the lateral opening 536 (as shown in FIG. 5A). The hypotube 544 may exhibit a shape that corresponds to the shape of the proximal and distal sections 519, 520 of the guidewire lumen 510 when the hypotube 544 is in the first state. The hypotube 544 may be switched from the first state to the second state by retracting the hypotube 544 and the guidewire (not shown) such that the hypotube 544 and the guidewire are no longer in the distal section 519 of the guidewire lumen 510. When the hypotube 544 is in the second state, the portions of the hypotube 544 adjacent to the lateral opening 534 are able to bend to exhibit the curved shape thereof thereby allowing the hypotube 544 to extend through at least a portion of the lateral opening 534. The curved shape of the hypotube 544 allows the hypotube 544 to form an off-ramp of the catheter 500. As such, advancing the guidewire when the hypotube 544 is in the second state towards the distal end 511 causes the guidewire to exit the catheter 500 out of the lateral opening 534. In another embodiment, the hypotube 544 may be retracted further proximal to the lateral opening 534 such that it straightens out in the guidewire lumen 510; hypotube 544 is then rotated 180-degrees and re-advanced toward the distal end of the guidewire lumen 510. Doing so keeps the hypotube straight in the guidewire lumen 510 while the hypotube 544 is biased against the opposing inner wall of the lateral opening 534. The hypotube 544 can then be re-positioned to the original state as in FIG. 5A enabling a guidewire to be advanced to the distal end of guidewire lumen 510.

Figure 6A:
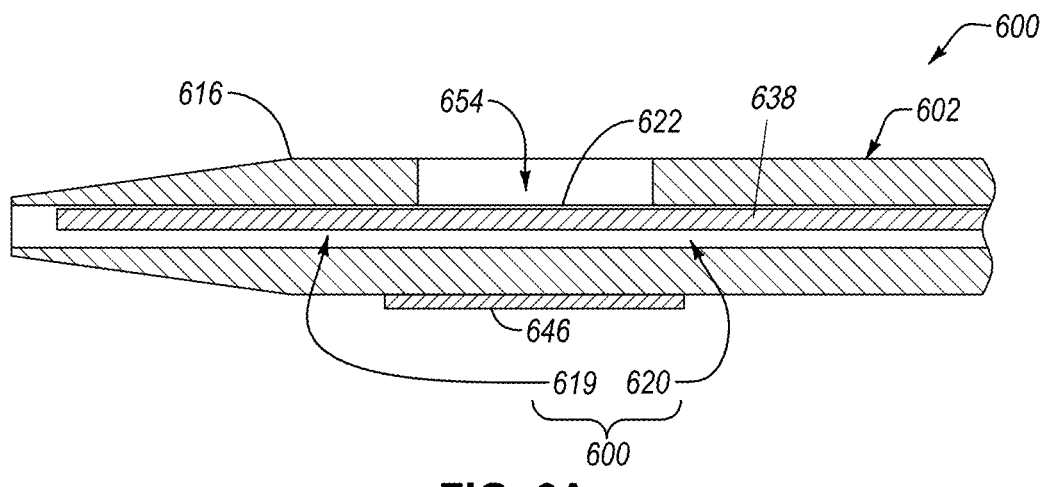
Figure 6B:
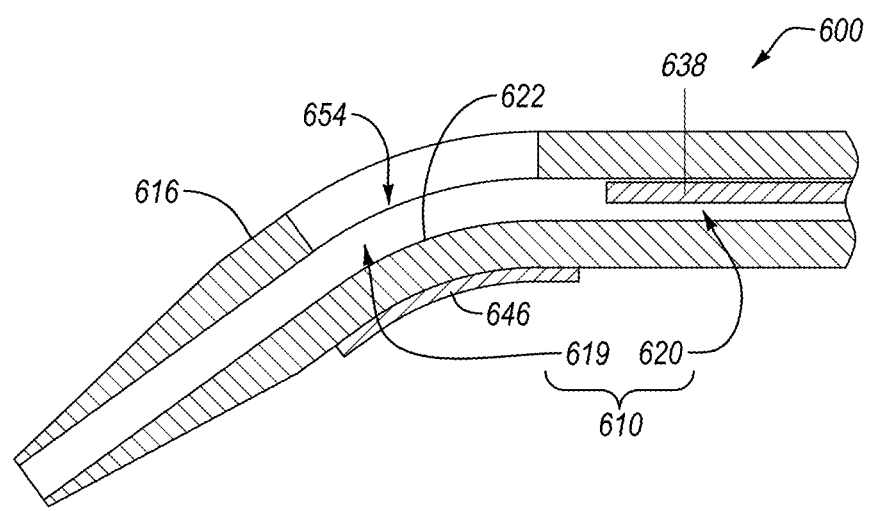

Referring to FIGS. 6A and 6B, the catheter 600 includes a housing 602. The housing 602 defines a guidewire lumen 610 including the distal section 619 and the proximal section 620. The housing 602 defines a lateral opening 654 extending from a lateral edge 616 to the guidewire lumen 610 at the intersection 622 of the distal and proximal sections 619, 620. The catheter 600 also includes a biasing member 646 attached to at least a portion of the lateral edge 616 opposite the portion of the housing 602 defining the intersection 622. When the guidewire is disposed in distal and proximal sections 610, 620 of the guidewire lumen 610, the distal catheter region of the catheter 600 may be substantial straight (as shown in FIG. 6A). Retracting the guidewire 638 from the distal section 619 of the guidewire lumen 610 allows the biasing member 646 bend a portion of the distal catheter region of the housing 602 (as shown in FIG. 6B). Advancing the catheter towards the distal tip 611 after the biasing member 646 bends the housing 602 allows the distal section 619 to bend the guidewire 638 thereby changing the direction that the guidewire 638 extends. In other words, the biasing member 646 causes the distal section 619 to form the off-ramp of the catheter 600.

FIGS. 1A-6B illustrate a variety of guidewire feeders. It is noted that any of the catheters disclosed herein can include one or more of the guidewire feeders disclosed above or any other conventional guidewire feeder, including combinations of any of the foregoing guidewire feeders.

Figure 7:
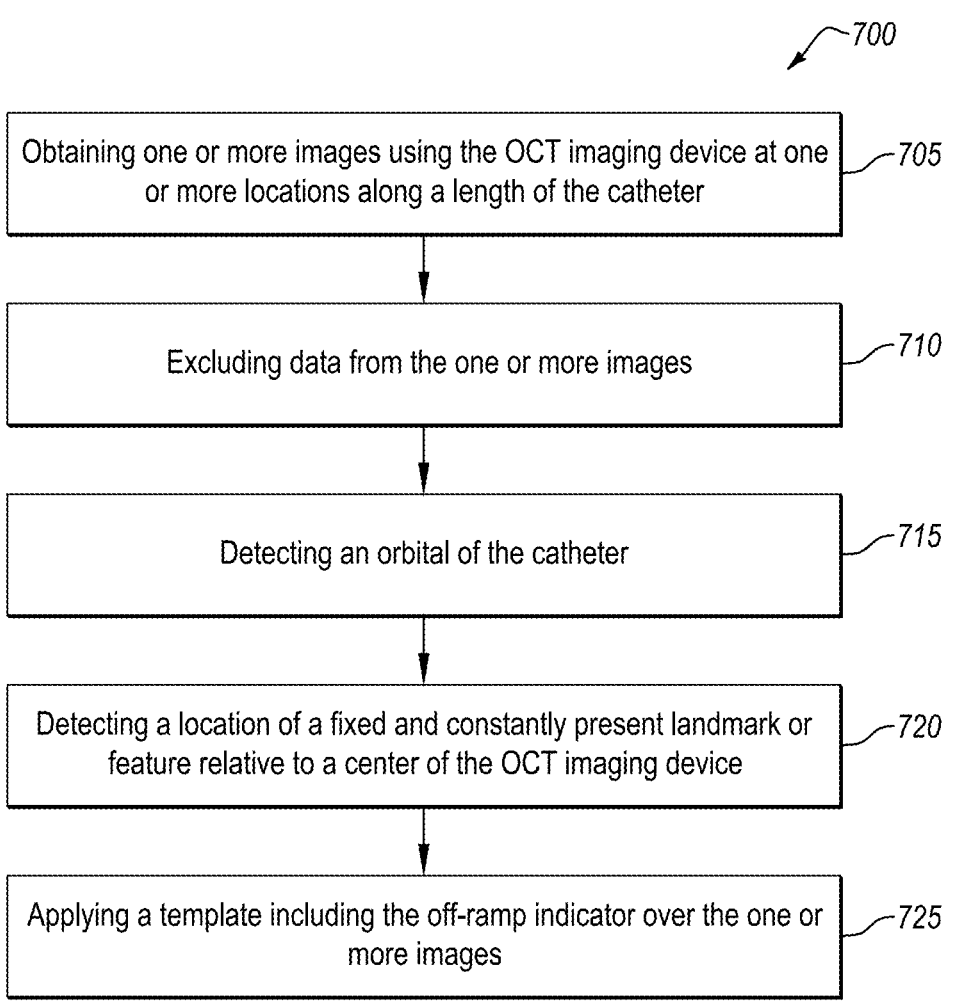
FIG. 7 is a flow chart of an example method to provide the off-ramp indicator, according to an embodiment.
Figure 8B:
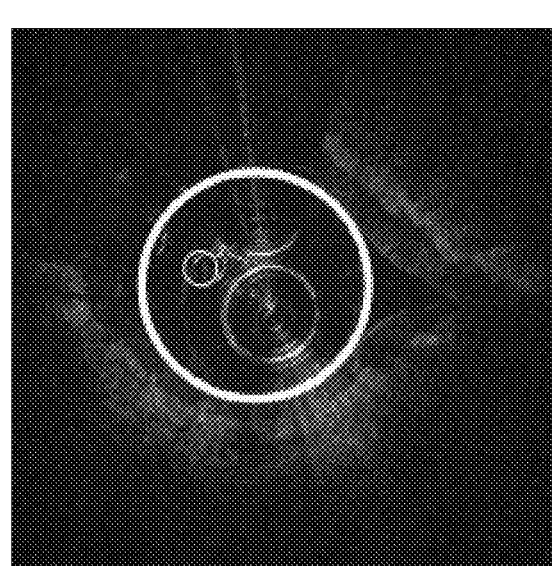
FIGS. 8A-8HH are schematics illustrating locations on the catheter at which images may be taken and examples of raw and ramp overlay images taken at each location, according to an embodiment.
Figure 8B:
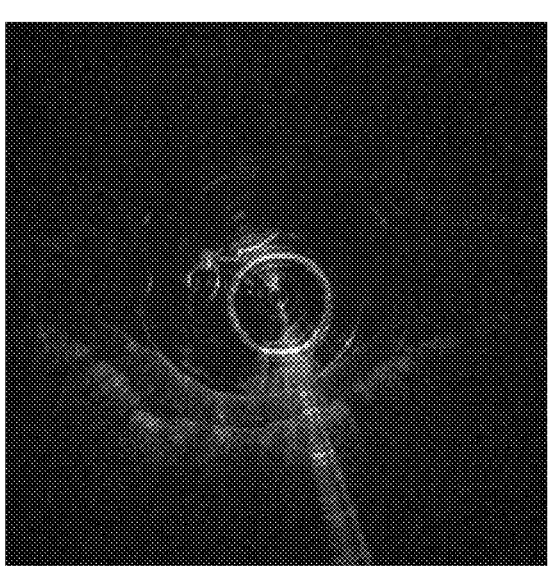
Figure 8A:
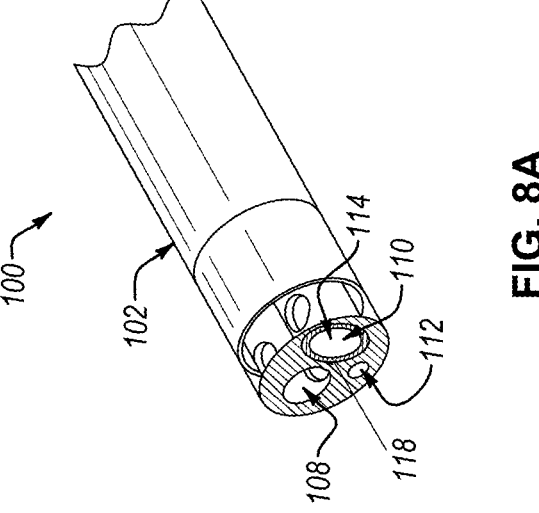
Figure 8D:
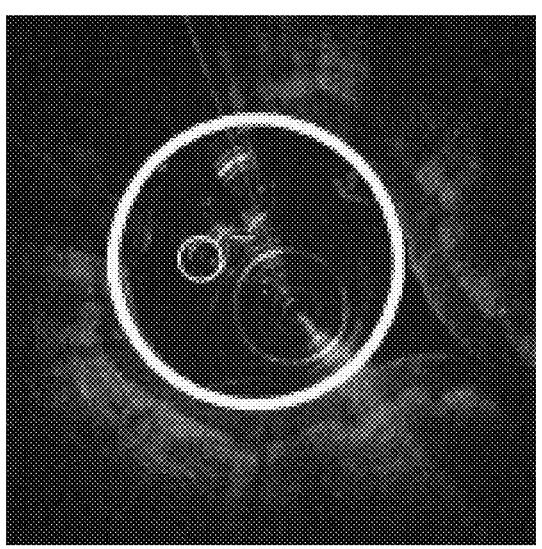
Figure 8D:
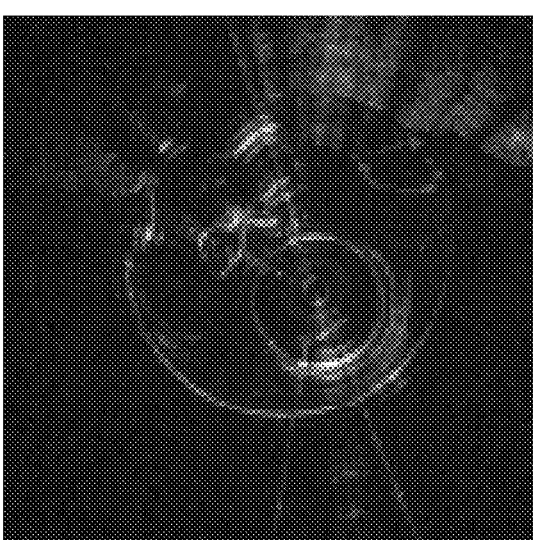
Figure 8C:
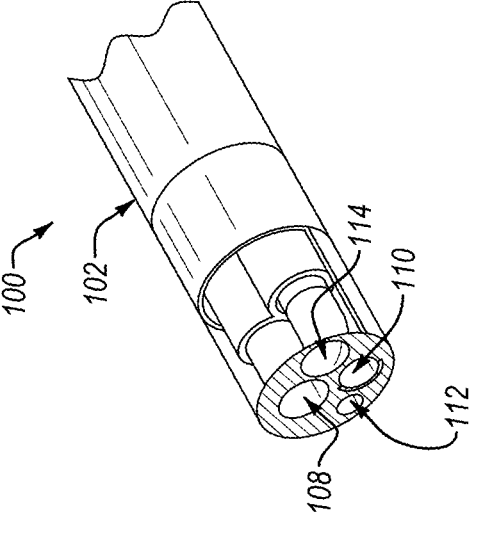
Figure 8F:
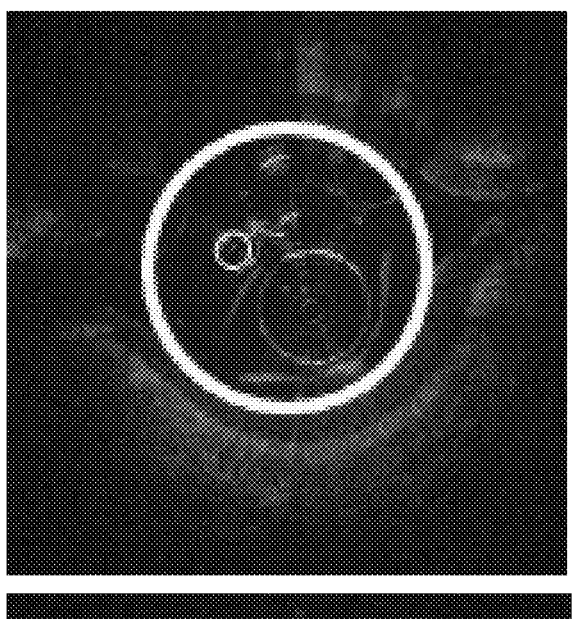
Figure 8F:
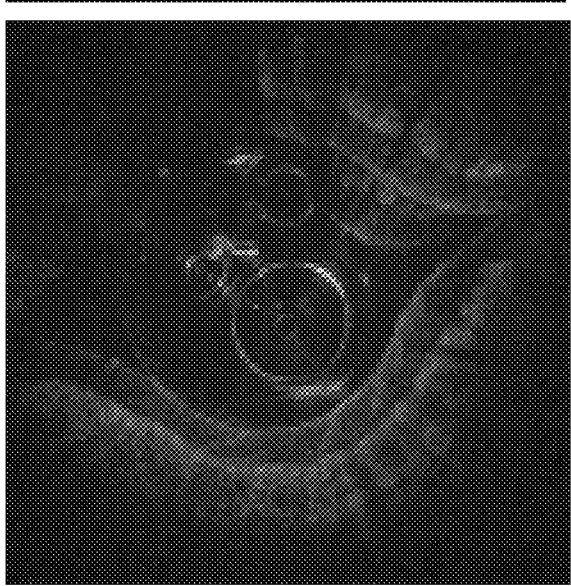
Figure 8E:
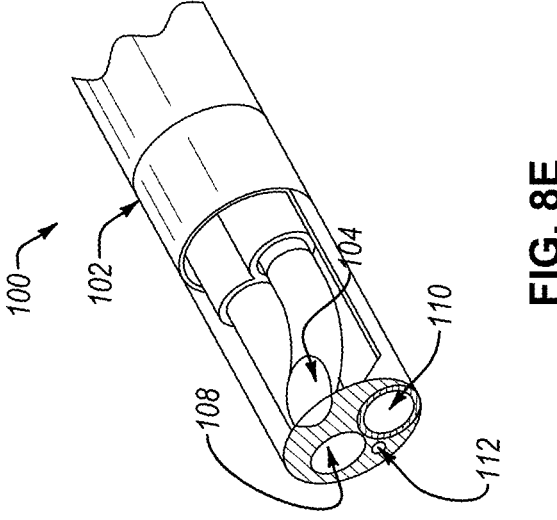
Figure 8H:
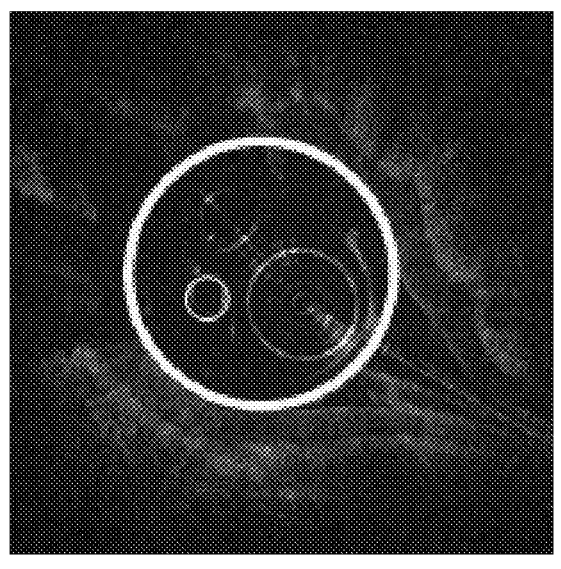
Figure 8H:
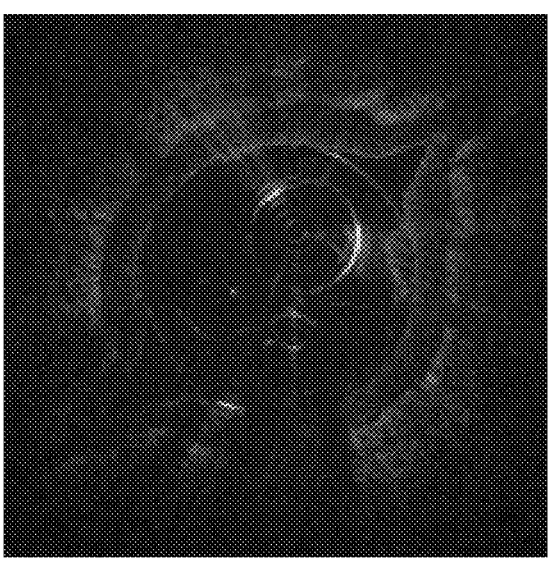

FIGS. 7-8HH and the accompanying description illustrate an exemplary method of using a catheter. For simplicity and clarity, the catheter 100 illustrated in FIGS. 1A-1C will referenced during the discussion of the method of using a catheter. However, it is noted that the method of using a catheter discussed below may be used with any suitable catheter, including any of the catheters discussed herein or any conventional catheter.

The individual (e.g., surgeon) using the catheter 100 may use the OCT imaging device 109 to facilitate using the off-ramp 114 to change the direction that the guidewire extends. In a particular embodiment, the individual using the catheter 100 may position the catheter 100 such that the off-ramp 114 faces opposite the adventitia of the lumen (e.g., the outermost tissue layer of the artery wall) since perforating of the adventitia may cause hemorrhaging into the pericardium. Such a positioning of the catheter 100 allows the off-ramp 114 to be aligned in the direction of the true lumen where the individual wants to force the guidewire. However, it may be difficult for the individual using the catheter 100 to determine the direction that the off-ramp 114 is oriented using the OCT imaging device 109.

As such, the methods and systems disclosed herein are configured to provide an off-ramp indicator 1202 (shown in FIG. 12) that indicates the general direction that the off-ramp 114 is oriented. The off-ramp indicator 121 assists the individual in identifying the direction toward which the off-ramp 114 is pointing and through which the user forces the guidewire out toward, in this case in the direction of the true lumen or artery. The off-ramp indicator 121 is configured to be accurate and clear enough to prevent confusing the individual using the catheter 100.

FIG. 7 is a flow chart of an example method 700 to provide the off-ramp indicator, according to an embodiment. The method 700 may include one or more operations, functions, or actions as illustrated by one or more of blocks 705, 710, 715, 720, or 725. The operations described in blocks 705 to 725 may be performed (or caused to be performed) in response to execution of computer-executable instructions stored on non-transitory memory.

Figure 13:
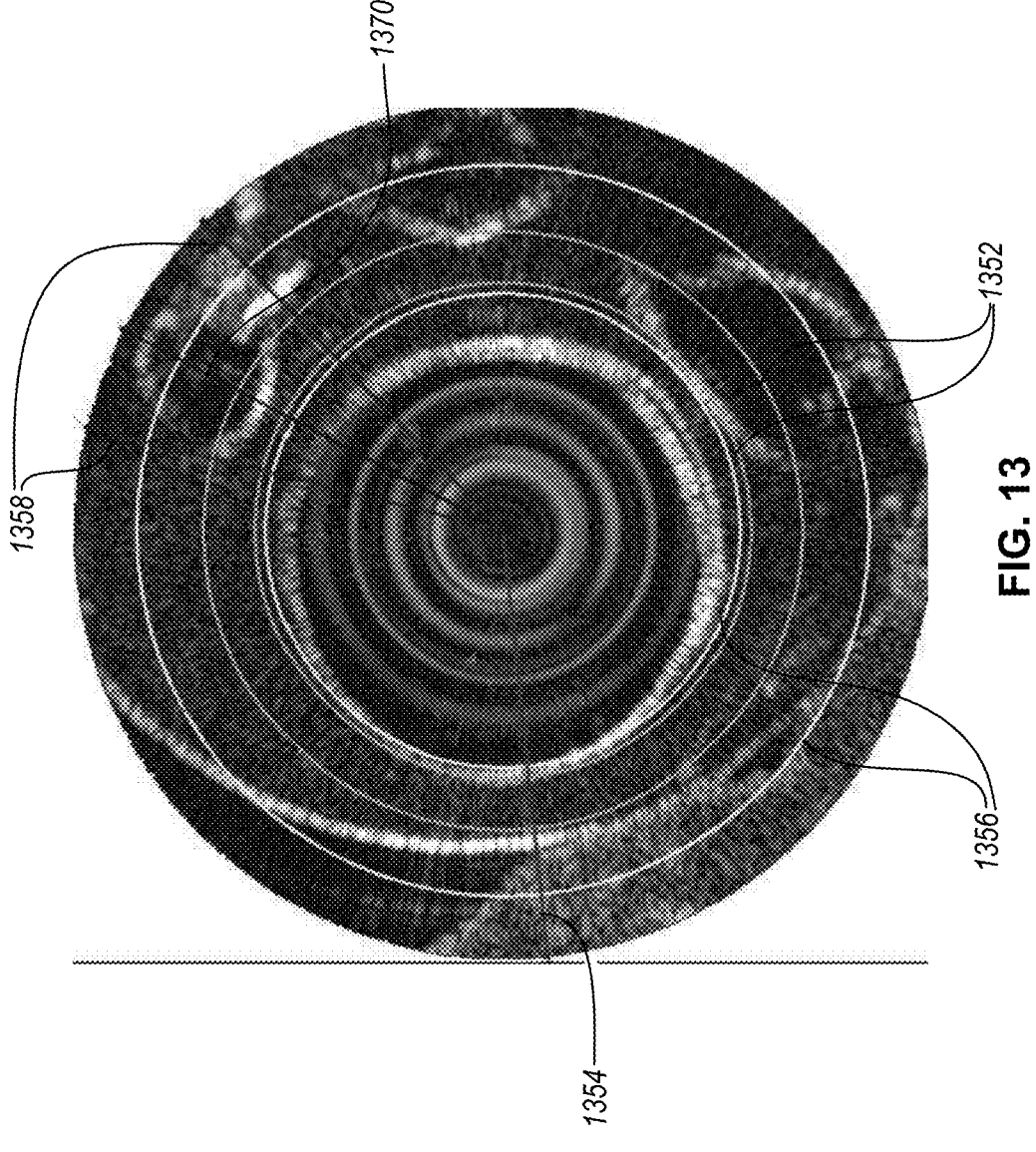
FIG. 13 is a circular image that may be used to find the orbital of the catheter and the indicator lumen, according to an embodiment.

The method 700 includes block 705, which includes obtaining one or more images using the OCT imaging device 109 at one or more locations along a length of the catheter 100. The method 700 may include block 710, which includes excluding data from the one or more images. The method 700 may include block 715, which includes detecting an orbital of the catheter 100. The method 700 may include block 720, which includes detecting a location of a fixed and constantly present landmark or feature relative to a center of the OCT imaging device 109. The method 700 may include detection of the orbital with block 715 and detection of the fixed and constantly present landmark or feature relative to a center of the OCT imaging device 109 with block 720, for one or more iterations, in a forward or backward order, that may be predetermined by an algorithm. The method 700 may include block 725, which includes applying a template including the off-ramp indicator over the one or more images (as shown in FIG. 13).

The blocks included in the method 700 are for illustrative purposes. In an example, the blocks may be performed in the order listed or in a different order. In an example, one or more of the blocks 705 to 725 may be omitted, divided into a plurality of blocks, modified, or supplemented. In an example, two or more of the blocks 705 to 725 may be combined into a single block. In an example, the method 700 may include one or more additional blocks, such as modifying or otherwise editing the one or more images (e.g., changing the brightness or contrast of the images).

Figure 9:
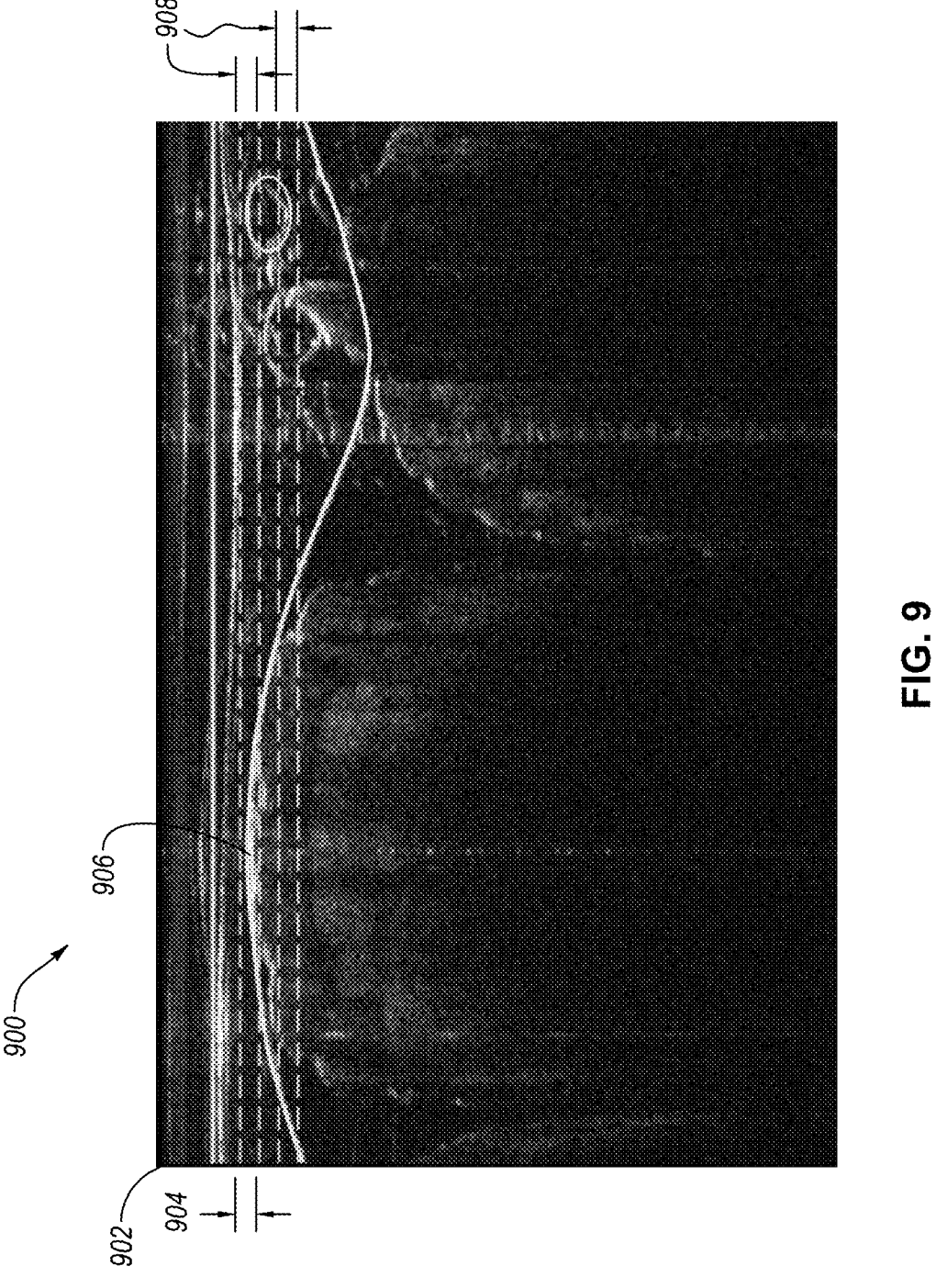
FIG. 9 is an example of a waterfall image taken at the location illustrated in FIG. 8HH, according to an embodiment.
Figure 11:
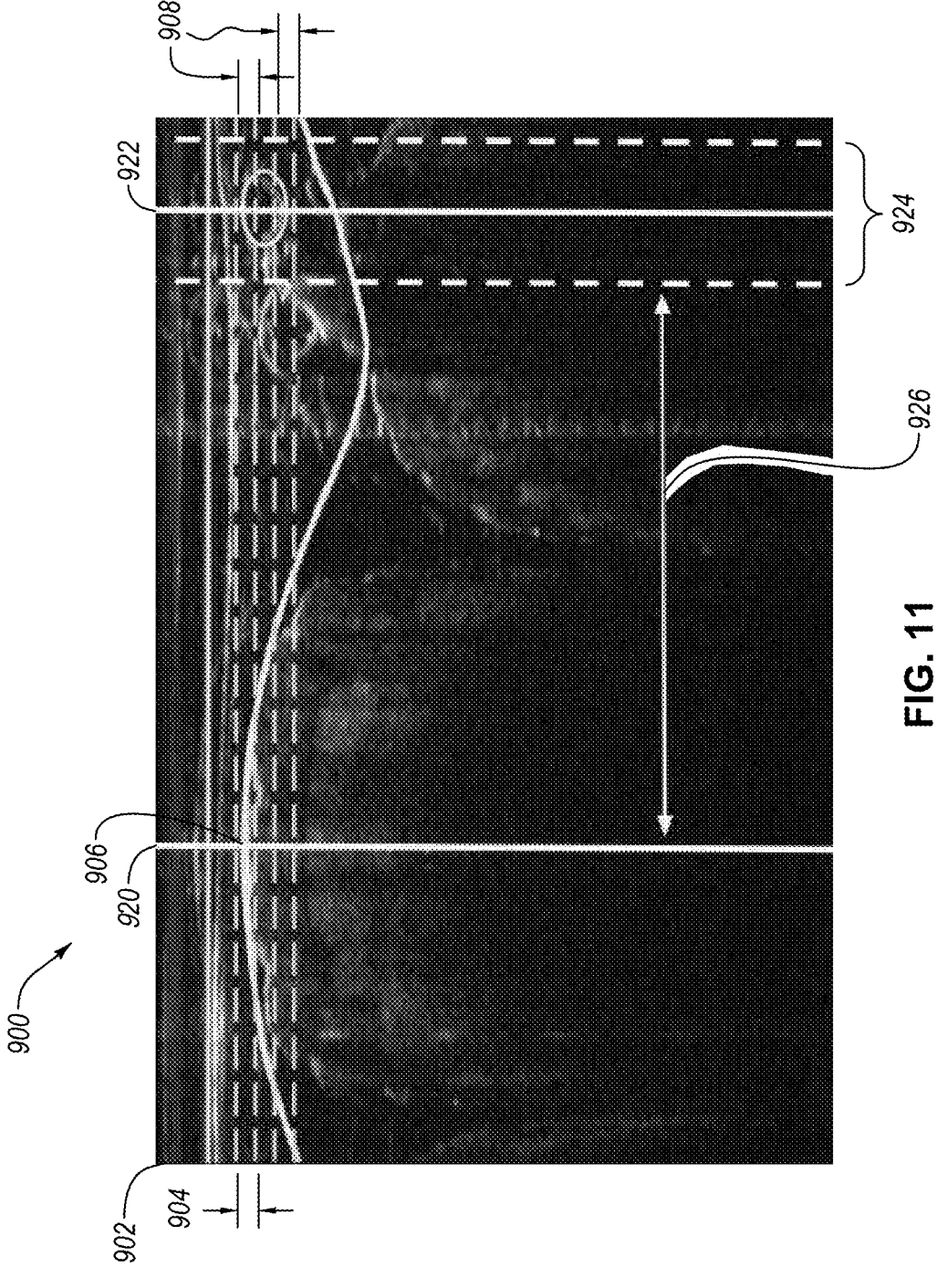
FIG. 11 is the waterfall image shown in FIG. 9 further annotated to indicate additional information shown thereon.

Block 705 includes obtaining one or more images using the OCT imaging device 109 at one or more locations along a length of the catheter 100. The OCT imaging device 109 may take 1D images. Each 1D image may include hundreds to thousands of data points (i.e., pixels). The OCT imaging device 109 may take a plurality of the 1D images to create a 2D image. The 2D image created by the OCT imaging device 109 may be a waterfall image (as shown in FIGS. 9 and 11) or a sector, non-waterfall image (as shown in FIGS. 8D, 8DD, 8F, 8FF, 8H, 8HH, 12, and 13).

In an embodiment, the OCT imaging device may capture a single 2D image at a certain location along the length of the catheter 100 or may take a plurality of 2D images at various locations along the length of the catheter 100. FIGS. 8A-8HH are examples of various locations on the catheter 100 and examples of circular, non-waterfall images (sector view) taken at each of the locations. FIG. 8A illustrates that the first image may be taken at a location where the off-ramp 114 begins to branch from the guidewire lumen 110 and FIG.

Figure 8G:
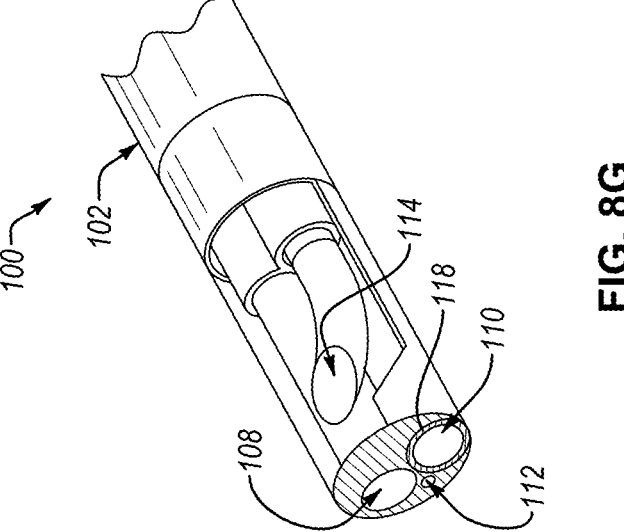

8B is an example of the first image in non-annotated form. To facilitate review of the first image, FIG. 8BB includes circles superimposed thereon indicating the edge of the catheter 100 (the larger circle) and the indicator lumen 112 (the smaller circle). It is noted that the subsequent images include similar circles superimposed thereon. FIG. 8C illustrates that the second image may be taken at a location closer to the distal end 111 than the first image (FIG. 8A) where the off-ramp 114 is distinct from the guidewire lumen 110 and FIGS. 8D and 8DD are examples of the second image in non-annotated and annotated forms, respectively. FIG. 8E illustrates that the third image may be taken at a location closer to the distal end 111 than the second image (FIG. 8C) where the off-ramp 114 meets the lateral edge 116 and FIGS. 8F and 8FF are examples of the third image in non-annotated and annotated forms, respectively. FIG. 8G illustrates that the fourth image may be taken at a location closer to the distal end 111 than the third image (FIG. 8E) between the off-ramp 114 and the distal end 111 and FIGS. 8H and 8HH are examples of the fourth image in non-annotated and annotated forms, respectively. It is noted that the locations discussed above are merely provided as examples and block 705 may include capturing 2D images at more or fewer locations and/or may include capturing 2D images at different locations on the catheter 100.

It is noted that it is difficult or impossible to determine the orientation of the catheter 100 in FIGS. 8B, 8D, 8F, and 8H. For example, it is difficult or impossible to determine which direction that off-ramp 114 extends from the guidewire lumen 110 or which direction the guidewire would extend from the off-ramp 114. As such, it is important to find the orientation of the catheter 100 and, in particular, the direction that the off-ramp 114 extends from the guidewire lumen 110, which the off-ramp indicator 1202 (shown in FIG. 12) provides.

Block 710 includes excluding data from the one or more images. The information contained in the images is highly redundant and, in some locations, is highly unlikely to provide useful information in determining the orientation of the catheter 100. As such, dropping data from the one or more images may reduce the redundancy, noise, and amount of data that is analyzed. The reduced redundancy, noise, and data makes determining the orientation of the catheter 100 quicker such that the orientation of the catheter 100 may be determined in real time (from the perspective of the individual using the catheter 100) and makes determining the orientation of the catheter 100 more accurate by decreasing the likelihood that the computer system misidentifies the features of the catheter 100.

Block 710 may include analyzing a waterfall image. FIG. 9 is an example of a waterfall image 900 taken at the location of the catheter 100 between the distal tip 111 and the off-ramp 114, according to an embodiment. The waterfall image 900 includes a plurality of 1D images taken by the OCT imaging device 109. Each of the 1D images (or A-lines in OCT, A-mode lines in ultrasound imaging) may be arranged as columns in the waterfall image. That is, the waterfall image may be arranged in a horizontal direction over the time interval (or B-scan). This exemplary waterfall image 900 is also annotated to show the catheter edge detection range 904 from the imager origin 902 where detection of the lateral edge 116 of the catheter 100 is performed, which in turn is used to detect the peak 906 of the sine wave defined by the lateral edge 116 of the catheter 100. It has been found that, in some applications, the peak 906 may be the feature of the catheter 100 that is most easily and/or reliably detected. Also depicted is the lumen detection range 908, in which the detection of the indicator lumen 112 is performed. The lumen detection range 908 decreases the likelihood that other features resembling the indicator lumen 112 is inadvertently detected and identified as the indicator lumen 112. The waterfall image shown in FIG. 9 may include 5000 1D images, though it is noted that waterfall image detected by the OCT imaging device 109 may include more or fewer than 5000 1D images. Block 710 may include reducing the number of 1D images in the waterfall image due to the redundant information contained in the 1D images. For example, block 710 may include excluding all but every $\frac{1}{10}$ to every $\frac{1}{35}$ (e.g., every $\frac{1}{27}$) 1D image from the waterfall image. In a particular example, block 710 may include reducing the number of 1D images to about 180 images.

The components of the catheter 100 are likely to within a threshold distance from the OCT imaging device 109 while anything else spaced further from the OCT imaging device 109 than the threshold distance is likely to be the lumen or portions of the body. As such, only data contained within a threshold distance from the top of the waterfall image is likely to contain data regarding the components of the catheter 100. Block 710 may include excluding data that is spaced a more than a threshold distance from the top of the waterfall image since such data is unlikely to contain information regarding the components of the catheter 100. In other words, block 710 may include retaining data that is within the threshold distance of the top of the image. In the particular example illustrated in FIG. 9, block 710 may include excluding all data that is more than 200 data points (i.e., pixels) from the top of the image since such data is unlikely to contain information about the components of the catheter 100.

As will be discussed in more detail below, blocks 715 and 720 include determining the location (e.g., distance and/or angle) of certain components, edges or interfaces of the catheter 100 relative to the center of the OCT imaging device 109. It is noted that the location of these components of the catheter 100 relative to the center of the OCT imaging device 109 may vary for a variety of reasons. In an example, the locations of these components of the catheter 100 relative to the center of the OCT imaging device 109 may depend on the particular catheter 100. In an example, the OCT imaging device 109 may move in the imaging lumen 108 which may change the location of the components of the catheter 100 relative to the center of the OCT imaging device 109. FIGS. 10A to 10D are cross-section views of the catheter 100 illustrating how moving the OCT imaging device 109 in the imaging lumen 108 changes the location of different components of the catheter 100 relative to the center of the OCT imaging device 109, according to an embodiment. In particular, FIGS. 10A to 10D illustrate the OCT imaging device 109 located at the top, bottom, left, and right regions of the imaging lumen 108, respectively. Depending on the location of the OCT imaging device 109 in the imaging lumen 108, the distance from the center of the OCT imaging device 109 and an orbital of the catheter 100 (i.e., the lateral edge 116 of the catheter 100 that is closest to the center of the OCT imaging device 109) varies. Also, depending on the location of the OCT imaging device 109 in the imaging lumen 108, the angle measured between a shortest line extending from the center of the OCT imaging device 109 to the orbital of the catheter 100 and a line extending from the center of the OCT imaging lumen 108 to a center of the indicator lumen 112 varies. It is noted that the location of the components of the catheter 100 relative to the center of the OCT imaging device 109 may also vary due to compressive forces applied from the lumen to the catheter 100, bending of the catheter 100, and/or manufacturing defects. Blocks 715 and 720 will use ranges instead of exact locations to find components of the catheter 100 to accommodate for these variations.

Block 715 includes detecting an orbital of the catheter 100. As previously discussed, the orbital of the catheter 100 is the lateral edge 116 of the catheter 100 that is closest to the center of the OCT imaging device 109. Referring back to FIG. 9, the OCT imaging device 109 may not be located in the center of the catheter 100 and, as such, the distance from the center of the OCT imaging device 109 to the lateral edge 116 of the catheter 100 may vary. The varying distance between the center of the OCT imaging device 109 and the lateral edge 116 causes the lateral edge 116 to appear as a sine wave in the waterfall image. A sine wave is superimposed on image of FIG. 9 to more clearly show the lateral edge 116 of the catheter 100. The approximate distance from the center of the OCT imaging device 109 and the orbital of the catheter 100 is known, with any uncertainty largely due to the OCT imaging device 109 not being centered in the imaging lumen 108. Two horizontally-extending lines are used to restrict the region of the waterfall image where the orbital of the catheter 100 may be located. The two lines correspond to the approximate distance from the center of the OCT imaging device 109 to the orbital of the catheter 100 with the space between the two annuli accommodating variations in the distance between the center of the OCT imaging device 109 and the orbital for the reasons previously discussed. The system may restrict or at least focus the search for the orbital of the catheter 100 in the space between the two lines. It is noted that restricting or focusing the search of the orbital of the catheter 100 between the two lines prevents or at least inhibits false positives. The orbital of the catheter 100 is the portion of the sine wave (i.e., the lateral edge 116 of the catheter 100) that is closest to the top of the waterfall image. FIG. 11 is the waterfall image shown in FIG. 9 further annotated to indicate additional information shown thereon, including indicating the orbital angle 920 of the catheter 100, which is the axis between the imager origin 902 to the closest distance to the catheter edge (e.g., peak 906 of the sine wave) . . . . As will be discussed in more detail below, FIG. 11 also depicts the indicator lumen angle 906, which is the axis between the imager origin 902 to the center of the detected indicator lumen 112. The detection of the indicator lumen 112 is facilitated by constraining the search based on the distance range 908 from the imager origin 902, but may also be constrained by the indicator lumen angle range 924. The angular distance 924 is based on the slope characteristics of the sine wave. Once the indicator lumen angle 906 is identified, the angle offset between the orbital angle 920 and the indicator lumen angle 906 may be determined.

In an embodiment, the search for the orbital of the catheter 100 is performed using an independent template search. The independent template search looks for the orbital of the catheter 100 between the two lines, as previously discussed. The template search uses templates extracted from a typical reduced waterfall image, processed by Gaussian blurring, and then rescaled. The template search includes of a squared difference between the template and patches of the search region (the template slides over the search region), and the result is then normalized. The result of the template search are sureness images, with hot spots indicating a high likelihood of a feature present at that location.

Block 720 includes detecting a location of a fixed and constantly present landmark or feature relative to a center of the OCT imaging device 109. The fixed and constantly present landmark or feature may be constantly present along at least a portion of a length of the catheter 100. For brevity, the indicator lumen 112 is discussed as being the fixed and constantly present landmark feature. However, it is noted that other components, edges, or interfaces of the catheter 100 may be the fixed and constantly present landmark feature instead of or in addition to the indicator lumen 112.

In an embodiment, block 720 includes detecting the orbital(s) of the indicator lumen 112 relative to the center of the OCT imaging device 109. The orbital of the indicator lumen 112 may refer to the portion of the indicator lumen 112 that is closest to and/or furthest from the center of the OCT imaging device 109. The approximate distance from the center of the OCT imaging device 109 (the top of the waterfall image) and the orbital(s) of the indicator lumen 112 is known, which any uncertainty largely due to the OCT imaging device 109 not being centered in the imaging lumen 108. The distance from the center of the OCT imaging device 109 to the orbital(s) of the indicator lumen 112 may be known, experimentally or empirically determined (e.g., using the OCT images), or calculated based on the geometry of the particular catheter. Referring to FIG. 11, one or more sets of two horizontally-extending lines 908 are used to restrict the region of the waterfall image where the orbital(s) of the indicator lumen 112 may be located. The one or more sets of two lines correspond to the approximate distance from the center of the OCT imaging device 109 to the orbital(s) of the indicator lumen 112 with the space between the two lines accommodating variations in the distance between the center of the OCT imaging device 109 and the orbital(s) of the indicator lumen 112 for the reasons previously discussed. In FIGS. 9 and 11, two sets of two horizontally-extending lines 908 are used, one to restrict or focus the search for the orbital of the indicator lumen 112 that is closest to the center of the OCT imaging device 109 and the other to restrict or focus the search for the orbital of the indicator lumen 112 that is furthest from the center of the OCT imaging device 109. It is noted that the two lines 904 used to restrict or focus the search for the orbital of the indicator lumen 112 that is closest to the center of the OCT imaging device 109 are the same as the two lines 908 used to find the orbital of the catheter 100, though these two set of lines do not need to be the same depending on the geometry of the catheter 100. It is noted that restricting or focusing the search of the indicator lumen 112 between the two lines 908 prevents or at least inhibits false positives. To facilitate review, the indicator lumen 112 is illustrated in FIGS. 3 and 5 using a superimposed circle.

In an embodiment, the location of the orbital of the catheter 100, as detected during block 715, may be used to detect the location of the indicator lumen 112 relative to the center of the OCT imaging device 109. For example, the approximate angle is known between a line extending from the center of the OCT imaging device 109 to the orbital of the catheter 100 and a line extending from the center of the OCT imaging device 109 to the center of the indicator lumen 112 (hereinafter referred to as the "orbital/indicator angle"), with the uncertainty of the orbital/indicator angle largely due to the OCT imaging device 109 not being centered in the imaging lumen 108. The orbital/indicator angle may be known, experimentally or empirically determined (e.g., using the OCT images), or calculated based on the geometry of the particular catheter. Referring to FIG. 11, an angle offset 926 is a distance on the waterfall image that corresponds to the smallest approximate orbital/indicator angle. An indicator lumen angle range 924, which corresponds to the uncertainty in the orbital/indicator angle, extends from the angle offset 926. At least a portion of the indicator lumen 112 (e.g., the orbital(s) of the indicator lumen 112) is expected to be located within the indicator lumen angle range 924. Thus, search for the indicator lumen 112 may be restricted to or focused within the indicator lumen angle range 924. In a particular example, the search for indicator lumen 112 may be restricted to or focused within the overlap between the indicator lumen angle range 924 and between the one or more sets of two lines 908. It is noted that restricting or focusing the search of the indicator lumen 112 within the indicator lumen angle range 924 prevents or at least inhibits false positives.

Block 720 may detect the center of the indicator lumen 112 (indicated using the reference number 922 on FIG. 11) using the orbital(s) or other information of the indicator lumen 112 detected during block 720.

In an embodiment, the search for the fixed and constant landmark or feature is performed using an independent template search. The independent template search looks for the fixed and constant landmark or feature between the two lines, as previously discussed. The template search uses templates extracted from a typical reduced waterfall image, processed by Gaussian blurring, and then rescaled. The template search includes of a squared difference between the template and patches of the search region (the template slides over the search region), and the result is then normalized. The result of the template search are sureness images, with hot spots indicating a high likelihood of a feature present at that location.

Generally, the orbital of the catheter 100 is more reliably found in the waterfall image than the indicator lumen 112. As such, the orbital of the catheter 100 may be used to detect the orbital/indicator angle. However, in some embodiments, the indicator lumen 112 may be found with very high certainty (e.g., more reliably detected than the orbital of the catheter 100). In such embodiments, the indicator lumen 112 may be used to detect the orbital of the catheter 100, using the techniques discussed above. For instance, the location of the indicator lumen 112 and the known approximate orbital/indicator angle may be used to restrict or at least focus the search for the orbital of the catheter 100 to a certain area (i.e., the angle offset may be measured from the center of the indicator lumen 112 and an angle range extending from the angle offset is used to restrict or focus the search).

In an embodiment, block 705 may include detecting a plurality of images at different locations along the length of the catheter 100, as previously discussed. In such an embodiment, blocks 710 to 720 may be performed on only one, some, or all of the plurality of images. A sureness value may be detected for each of the images that blocks 710 to 720 are performed on. Only the images with the highest sureness value or images (if any) with a sureness valve above a threshold value is used to determine the orientation of the catheter 100 and the direction that the off-ramp 114 extends from the rest of the catheter 100.

Block 725 includes applying a template 1200 (shown in FIG. 12) including the off-ramp indicator 1202 over the one or more images. Preferably, block 725 applies the template 1200 to the one or more images substantially in real time thereby allowing the individual using the catheter 100 to known the orientation of the catheter 100 and the direction that the off-ramp 114 extends at any given time. As used herein, substantially in real time refers to a time period that is sufficiently small that the individual using the catheter 100 is unable to detect any delay or any delay is unlikely to adversely affect the operation of the catheter 100. For example, substantially in real time may allow a delay of about 5 seconds or less, more preferably a delay of about 1 second or less, or, even more preferably, less than about 0.5 seconds, or less than about 0.1 seconds.

The template 1200 includes the location (e.g., angles between) and relative distance between the imaging lumen 108, the guidewire lumen 110, the indicator lumen 112, the direction of the off-ramp 114 (shown using the off-ramp indicator 1202), and the lateral edges 116 of the catheter 100. The template 1200 may be known, experimentally or empirically determined (e.g., using the OCT images), or calculated on a per catheter basis. For example, three parameters of the template 1200 that may be known, determined, or calculated include the angle between the centers of the guidewire lumen 110 and the indicator lumen 112, the radial distance between the center of the imaging lumen 108 and the guidewire lumen 110, and the off-ramp angular direction relative to a vector from the center of the imaging lumen 108 and the center of the guidewire lumen 110. The template 120 may also make one or more assumptions, such as the diameter of the catheter 100, the diameter of the imaging lumen 108, the diameter of the guidewire lumen 110, the diameter of the indicator lumen 112, the relative angles of the centers of the three lumens, and the relative position of the three lumens in the catheter 100. The template 1200 may be aligned on the image such that the characteristics of the catheter 100 detected during blocks 715 and 720 are aligned with the corresponding portions of the template 1200.

Figure 12:
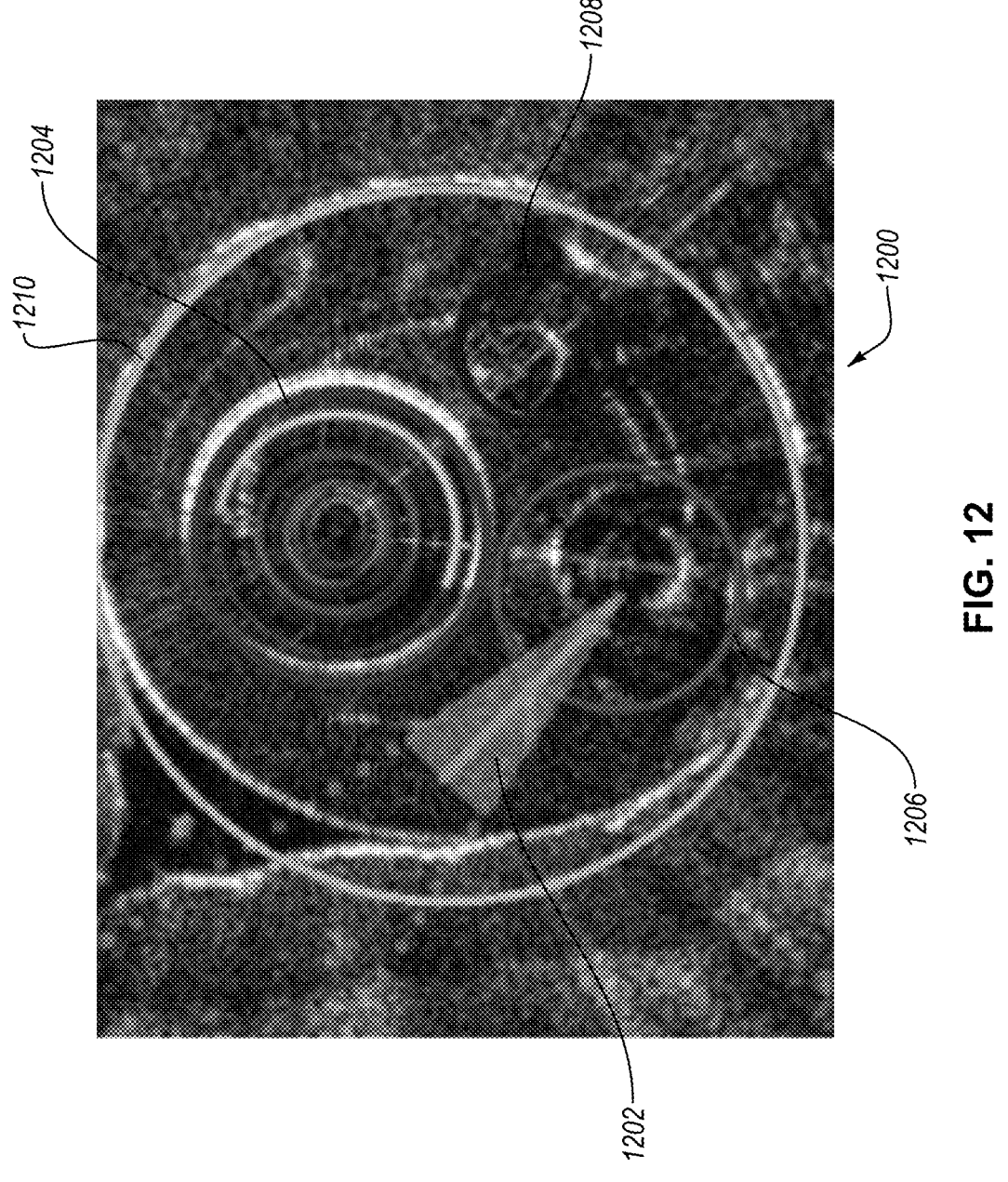
FIG. 12 illustrates a template superimposed on an image, according to an embodiment.

The template 1200 is a visual template. That is, the template 1200 adds one or more visual indications when superimposed over an image. FIG. 12 illustrates a template 1200 superimposed on an image, according to an embodiment. The template 1200 includes an off-ramp indicator 1202. The off-ramp indicator 1202 indicates the angular direction that the off-ramp 114 extends relative to the catheter 100 (e.g., relative to the guidewire lumen 110). The off-ramp indicator 1202 also indicates the orientation of the catheter 100. In an embodiment, the off-ramp indicator 1202 may include a line indicating the general angular direction that the off-ramp 114 extends relative to the rest of the catheter 100. In an embodiment, the off-ramp indicator 1202 may be a triangle, two lines extending from a point, a single line with an arrow, or other indicator that indicates the general angular direction that the off-ramp 114 extends relative to the rest of the catheter 100 along with any uncertainty. In an embodiment, as shown, the off-ramp indicator 1202 may include a line and an indicator that indicates the uncertainty (e.g., a triangle).

In an embodiment, the template 1200 may include at least one of an imaging circle 1204, a guidewire circle 1206, an indicator circle 1208, or a catheter edge circle 1210 that are shown when the template 1200 is superimposed on the image. The imaging circle 1204 may correspond to the location, size, and shape of the imaging lumen 108. The guidewire lumen 1206 may correspond to the location, size, and shape of the guidewire lumen 110. The indicator lumen 1208 may correspond to the location, size, and shape of the indicator lumen 112. The indicator lumen 112 provides a user of the catheter 100 a direct and real time visual feedback of how accurate the off-ramp indicator 1202 is predicting the guidewire exit trajectory. For example, if the indicator lumen 112 is misaligned from the indicator lumen, the user can accordingly estimate how deviated the guidewire would exit from the off-ramp indicator 1202. The catheter edge circle 1210 corresponds to the location, size, and shape of the lateral edge 116 of the catheter 100. The imaging circle 1204, the guidewire circle 1206, the indicator circle 1208, and/or the catheter edge circle 1210 provide a visual indication to the individual using the catheter 100 and facilitates the individual interpreting what is shown in the image. The imaging circle 1204, the guidewire circle 1206, the indicator circle 1208, and/or the catheter edge circle 1210 also helps indicate the orientation of the catheter 100 to the individual using the catheter 100. In an embodiment, the imaging circle 1204, the guidewire circle 1206, the indicator circle 1208, and/or the catheter edge circle 1210 may be selectively displayed. It is noted that the imaging circle 1204, the guidewire circle 1206, the indicator circle 1208, and/or the catheter edge circle 1210 may be slightly off on the image, for example, due to compression of the catheter 100 during use or manufacturing defects. Display of the off-ramp indicator 1202 or any elements of the template may be of any color or suitable form or shape that makes it easy for the user to identify. Not all the elements 1202, 1204, 1206, 1208 and 1210 need to be displayed. The off-ramp indicator 1202 displaying with the indicator circle 1208, for example, would satisfy the need for indicating the direction or trajectory of the guidewire exiting the off ramp 114 with a reference (the indicator circle) indicator relative to the position of a fixed landmark (the indicator lumen 112) to enable the user to judge if the off-ram indicator 1202 is displaying correctly.

The method 700 may include one or more additional blocks other than blocks 705 to 725. In an example, the method 700 may include creating the template 1200 customized for each catheter. Calibrating and creating the template 1200 each catheter may be tedious. As such, software may be used to acquire the variations for each catheter 100. The software may include generate various images of the catheter 100. The software may analyze the images and calibrate the template 1200 based on the various images. For instance, the software may detect one or more features of the catheter 100 and calibrate the template 1200 based on the detected features. In an embodiment, a user of the catheter 100 may review of the images to determine if the software accurately features and may allow the user to modify the template to accommodate errors in detecting the features.

In an example, the method 700 includes an optional block of copying a portion of the waterfall image before blocks 715 and 720. For example, the algorithms disclosed herein may have difficulty detecting the orbital of the catheter 100 and/or the indicator lumen 112, as discussed in blocks 715 and 720, if the orbital of the catheter 100 and/or the indicator lumen 112 is at least partially located at or near the lateral edges (e.g., left or right edge) of the waterfall image. As such, the method 700 may include copying a columnar portion of one edge of the waterfall image (either the right or left side) and adding the copied columnar portion to the other edge of the waterfall image. The columnar portion that is copied may include 5-30% (e.g., 15-25%) of the waterfall image. In a particular example, when the image includes 180 1D images, the first 40 1D images on the right side may be copied and added to the left side such that the water fall image now has 220 1D images. Copying the columnar portion of the waterfall image and adding the columnar portion to the opposing edge of the waterfall image ensures that the orbital of the catheter 100 and the indicator lumen 112 are not located at or near a lateral edge of the waterfall image.

In an example, the method 700 includes an optional block of detecting the sureness values of the orbital of the catheter 100 and the indicator lumen 112 detected during blocks 715 and 720 to decide whether there is sufficient certainty to warrant displaying the off-ramp indicator 121. In such an example, the off-ramp indicator 121 may be displayed when the sureness value is above a pre-determined threshold value. Detecting the sureness values of the orbital of the catheter and the indicator lumen 112 detected during blocks 715 and 720 prevents displaying erroneous results to individual using the catheter 100 that may confuse the individual.

In an example, the method 700 includes an optional block of editing the image. For instance, the method 700 may include adjusting the brightness of the image, adjusting the contrast of the image, or otherwise editing the image. Editing the image may facilitate detecting the orbital of the catheter 100 and/or detecting the indicator lumen 112. Editing the image may also make it easier for the individual using the catheter 100 to understand and interpret the OCT image.

In an example, the method 700 includes displaying the image detected to the individual as a catheter-centric view of the catheter 100 as opposed to the OCT imaging device 109 being the center of the image. In such an example, the template 120 may be catheter-centric.

It is noted that a circular image, instead of a waterfall image, may be used to find the orbital of the catheter 100 and/or the indicator lumen 112. For example, FIG. 13 is a circular image that may be used to find the orbital of the catheter 100 and the indicator lumen 112, according to an embodiment. Since FIG. 13 is not a waterfall image, annular lines are added to the image instead of horizontal lines. The outer two lines 1352 may indicate the space where the orbital of the catheter 100 may be found. The line 1354 indicates the location of the orbital of the catheter 100. The inner two annular lines 1356 indicate the space where the orbital of the indicator lumen 112 is expected to be found. The angled lines 1358 are the indicator lumen angle range. The line 1360 within the angled lines 1358 indicate the center of the indicator lumen 112.

In other embodiments, the indicator lumen 112 may be placed outside of the detection range 304 to entirely de couple it from the orbital edge detection. The indicator lumen 112 may also be of any shapes other than circular and sizes within the physical constraints of the catheter 100 to differentiate it from other features within the cross-section of the catheter 100.

In other embodiments, the lateral edge 116 of the catheter 100 may include a fixed feature along the travel range of the imaging device 109 in catheter 100. Such a feature may include placement and adhesion of a small clear or opaque elongated object or a groove along the travel range of the imaging device 109.

Figure 14:
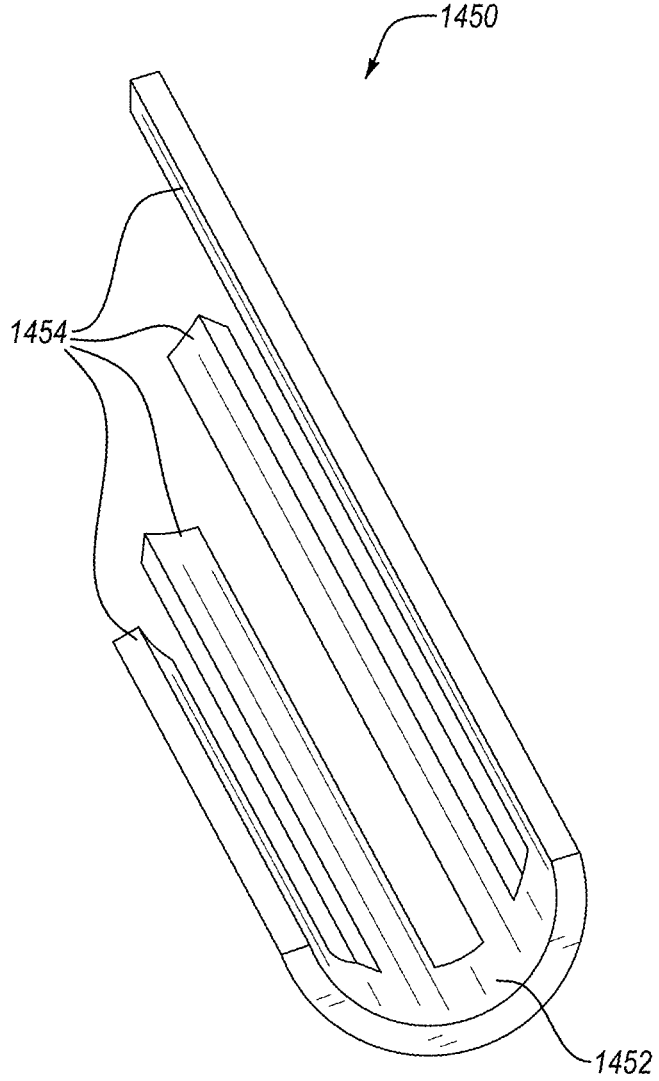
FIG. 14 is an isometric view of a detectable structure that may be disposed in or on a catheter (not shown), according to an embodiment.

As previously discussed, the imaging device of the catheters disclosed herein may detect images of the catheter at one or more locations along the length of the housing. For example, the imaging device may detect one or more images by physically moving the imaging device along the length of the housing. During use, it may be difficult for a user of the catheter to know the location of the imaging device at any given time and the location of the catheter and environment about the catheter that is being imaged by the imaging device. As such, any of the catheters disclosed herein may include a detectable structure configured to indicate the position of the imaging device along the length of the housing. FIG. 14 is an isometric view of a detectable structure 1450 that may be disposed in or on a catheter (not shown), according to an embodiment. The detectable structure 1450 is configured to be disposed in or on the housing 102.

The detectable structure 1450 is configured to be detectable by the imaging device 109. As such, the detectable structure 1450 is formed from a material that is easily detectable by an imaging device. For example, the detectable structure 1450 may be formed from a material that is at least partially opaque to or reflects the stimulus emitted or received by the imaging device. In an example, when the imaging device is an OCT imaging device, the detectable structure 1450 may be formed from a material that is at least one opaque (e.g., more opaque than the surrounding housing) or reflective to light. In an example, when the imaging device is an ultrasound device, the detectable structure 1450 may be formed from a material that is at least partially opaque (e.g., more opaque than the surrounding housing) or reflective to ultrasound wavelengths.

The detectable structure 1450 is configured to indicate a location of the imaging device relative the housing. For example, the detectable structure 1450 may indicate a distance from the distal tip, the intersection of the distal and proximal sections of the guidewire lumen, and/or distance from the intersection of the catheter body and the imaging body of the housing. The detectable structure 1450 indicates the location of the imaging device relative to the housing because the detectable structure 1450 has a known location on the housing.

The detectable structure 1450 includes a base 1452. The base 1452 may exhibit an annular or semi-annular shape since the housing 102 generally exhibits a circular cross-sectional shape. The annular or semi-annular shape of the base 1452 also allows lumens of the catheter to pass through the base 1452. In a particular embodiment the base may exhibit a semi-annular shape which allows the imaging device to detect at least a portion of the environment about the catheter when the imaging device is at least partially surrounded by the annular base 1452. The detectable structure 1450 also includes one or more elongated arms 1454 extending from the base 1452. The detectable base 1452 and the one or more elongated arms 1454 may be used to determine the position of the imaging device 109. For example, the imaging device may detect the base 1452 when the imaging device is adjacent to the base 1452 or within the volume at least a portion defined by the base 1452 thereby indicating the position of the imaging device. Similarly, the imaging device may detect the one or more elongated arms 1454 when the imaging device is adjacent to the one or more elongated arms 1454 thereby indicating the position of the imaging device. In an embodiment, as shown, the detectable structure 1450 includes a plurality of elongated arms 1454 extending from the base 1452. Each of the plurality of elongated arms 1454 may extend a different length from the base 1452. The position of the imaging device 109 may be determined based on the number of elongated arms 1454 detected by the imaging device 109. For example, using the particular detectable structure 1450 illustrated in FIG. 14, the imaging device 109 is position between the base 1452 and the terminal end of the shortest elongated arm 1454 when the imaging device 109 detects four elongated arms 1454 and the imaging device 109 is position between the terminal end of the second longest elongated arm 1454 and the terminal end of the longest elongated arm 1454 when the imaging device 109 detects one elongated arm 1454.

Figure 15:
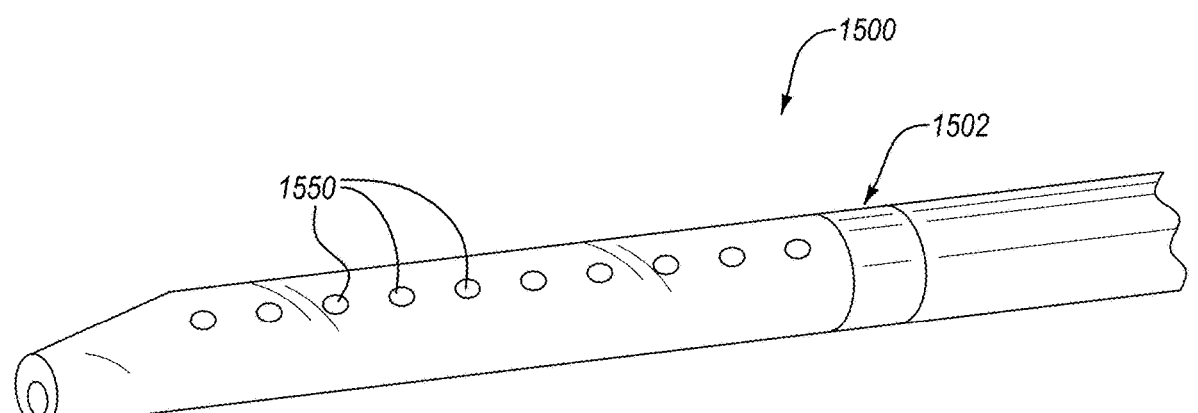
FIG. 15 is an isometric view of the catheter that includes a detectable structure, according to an embodiment.

The catheters disclosed herein may include the detectable structure other than the detectable structure 1450 illustrated in FIG. 14. For example, FIG. 15 is an isometric view of the catheter 1500 that includes a detectable structure 1550, according to an embodiment. Except as otherwise disclosed herein, the catheter 1500 may be the same as or substantially similar to any of the catheters disclosed herein. The catheter 1500 includes a housing 1502. To facilitate the illustration, the lumen(s) defined by the housing 1502 are not illustrated. The housing 1502 defines one or more holes and/or divots. The holes and/or divots may be spaced along a longitudinal axis of the housing 1502. The relative position of each of the holes and/or divots on the housing 1502 may be known. The holes and/or divots the may be detectable by the imaging device. As such, the holes and/or divots form of the detectable structure 1550. The position of the imaging device in the housing 1502 may be determined by counting the number of holes and/or divots that the imaging device passes as imaging device moves in the housing 1502.

Figure 16A:
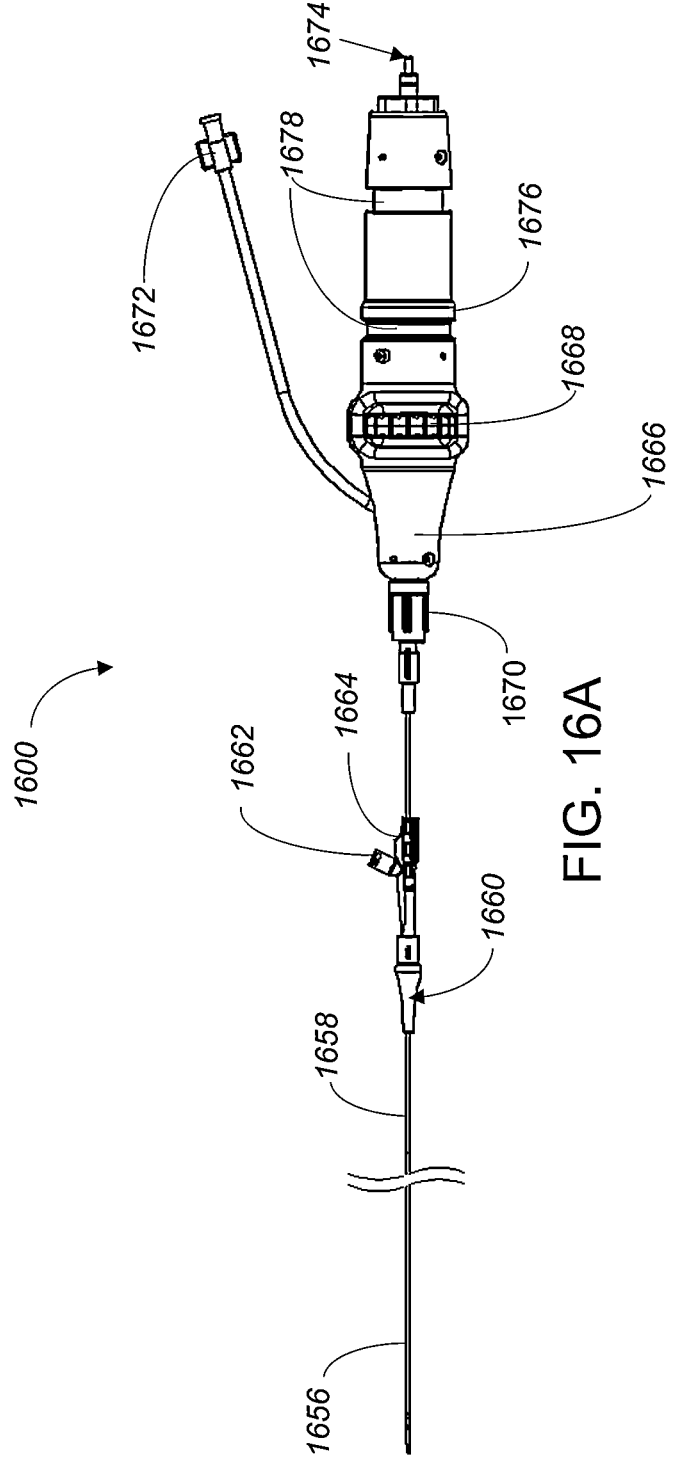
FIGS. 16A to 16D are side elevational, side cross-sectional, top and top cross-sectional views of an exemplary proximal catheter assembly.
Figure 16B:
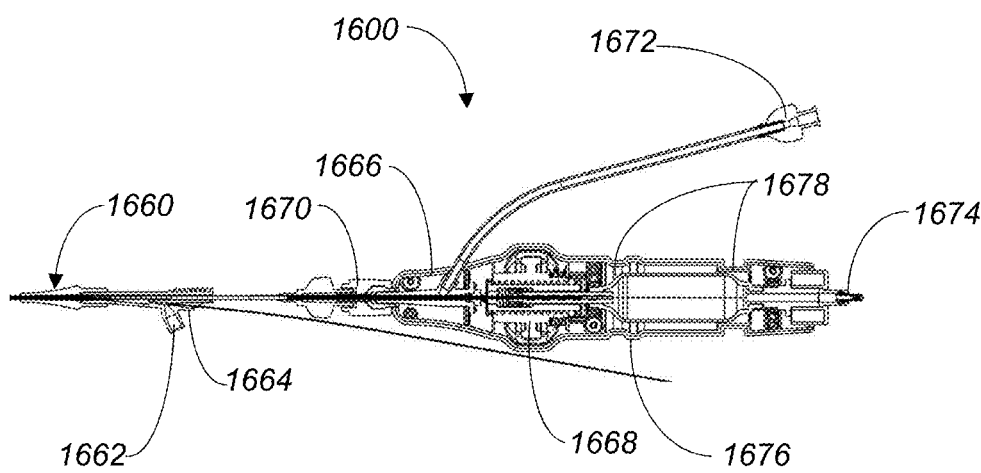
Figure 16C:
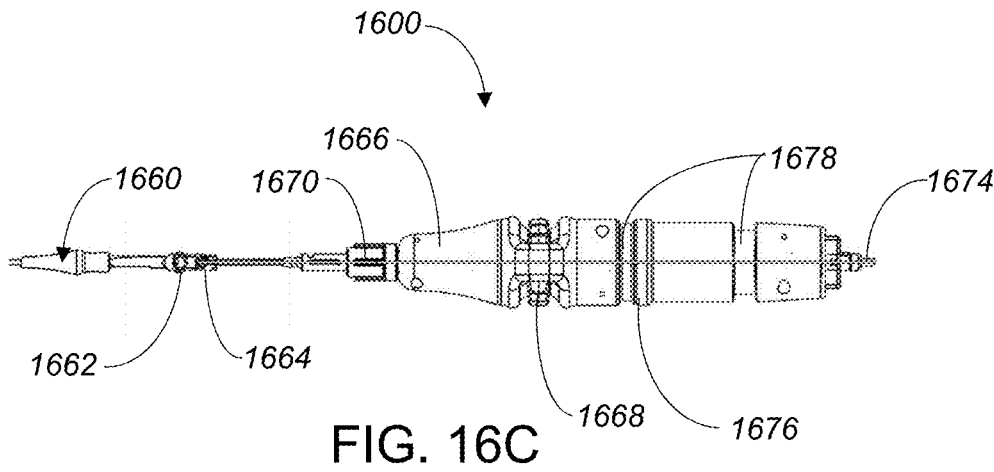
Figure 16D:
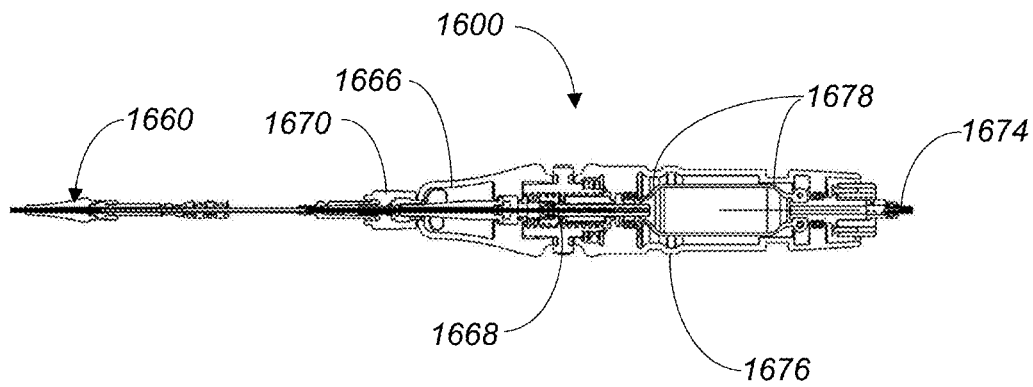

FIG. 16A is an side view of the catheter 1600, according to an embodiment. Except as otherwise disclosed herein, the catheter 1600 is the same as or substantially similar to any of the catheters disclosed herein. For example, the catheter 1600 includes a distal catheter region 1656 and a proximal catheter region 1658. The distal catheter region 1656 may be the same as or substantially similar to the catheter's shown in FIGS. 1A-6B. The overall length of the catheter 1600 from the terminal end of the distal catheter region 1656 to the proximal catheter region 1658 may be about 1 m to about 3 m. The portion of the catheter 1600 formed in the distal catheter region 1656 and the proximal catheter region 1658 may exhibit any suitable size, such as 4 French or smaller.

The catheter 1600 may include a hub 1660 attached to the terminal end of the proximal catheter region 1658. The hub 1660 may be optionally tapered in the distal direction, as depicted in FIG. 16A. The hub 1660 may be attached to the proximal catheter region 1658 using any suitable technique. For example, a portion of the proximal catheter region 1658 adjacent to the terminal end thereof may be disposed within the distal end of the hub 1660 attached thereto using an interference fit or the proximal catheter region 1658 may be integrally formed with the hub 1660. The hub 1660 may include one or more openings therein that allow access to one or more of the lumens of the distal scratch that of the catheter 1600. For example, the distal connector 1660 may include a guidewire flush port 1662 that is configured to allow one or more fluids to flow into the guidewire lumen. The hub 1660 may also include a guidewire introducer port 1664 that allows the guidewire to be introduced into the catheter and/or the distal end of the guidewire to extend out of the catheter 1600, as needed.

The catheter 1600 also includes a housing 1666. The housing 1666 is configured to be gripped and manipulated by a user of the catheter 1600. The housing 1666 may include one or more actuators that may be manipulated by the user of the catheter 1600 thereby allowing the user to operate the catheter 1600. For example, the housing 1666 may include a first actuator 1668 and the second actuator 1670, as well as one or more flanges 1676 and/or recesses 1678 to facilitate engagement or releasable attachment to other components, such as the sled assembly, an interconnect or handle socket for the housing 1666 or a sterile cover. The first and second actuator 1668, 1670 may include a knob (e.g., rotatable knob) or any other suitable actuator. The first and second actuators 1668, 1670 may be configured to control one or more operations of the catheter 1600. In an example, the first actuator 1668 may be used to adjust the longitudinal position of an imaging device inserted into and/or engaged to the housing 1666. In such an example, the first actuator 1668 may comprise a rotatable knob which utilizes a helically threaded interface to advance or retract the imaging device engaged to the interface. In other variations, the first actuator 1668 may comprise a mechanical slide or a rack-and-pinion assembly to move the imaging device. In an example, the second actuator 1670 is a catheter body rotation interface or adapter that facilitates rotation of the distal and proximal catheter regions 1656, 1658 without requiring rotation of the entire catheter 1600 and/or the housing 1666. As such, the rotation of the catheter off-ramp of the distal catheter region 1656 does not result in rotation of all the catheter structures. When the actuators are configured to rotate portions of the catheter 1600, the housing 1666 may include a fiber optic rotating junction, such as those made by Spinner (Munich, Germany), (Princetel (Hamilton, NJ), Moog (Elma, NY).

The housing 1666 may also include an optical connector 1672 (e.g., a standard 2.5 mm optical connector) provided at the proximal end of the housing 1666 to connect the catheter 1600 to a standard superluminescent diode (SLED) light source or a swept laser source of the OCT system. Any of a variety of known ophthalmic or medical OCT control systems or components may be used, (e.g. Zeiss CIRRUS® (Carl Zeiss Meditec USA, Inc.; Dublin, CA) and EnFocus (Leica Microsystems Inc.; Deerfield, IL)). The housing 1666 may also include one or more ports, for instance, the housing 1666 may include an image flushing port 1672 that is configured to allow one or more fluids that flowed into the imaging lumen.

Figure 16E:
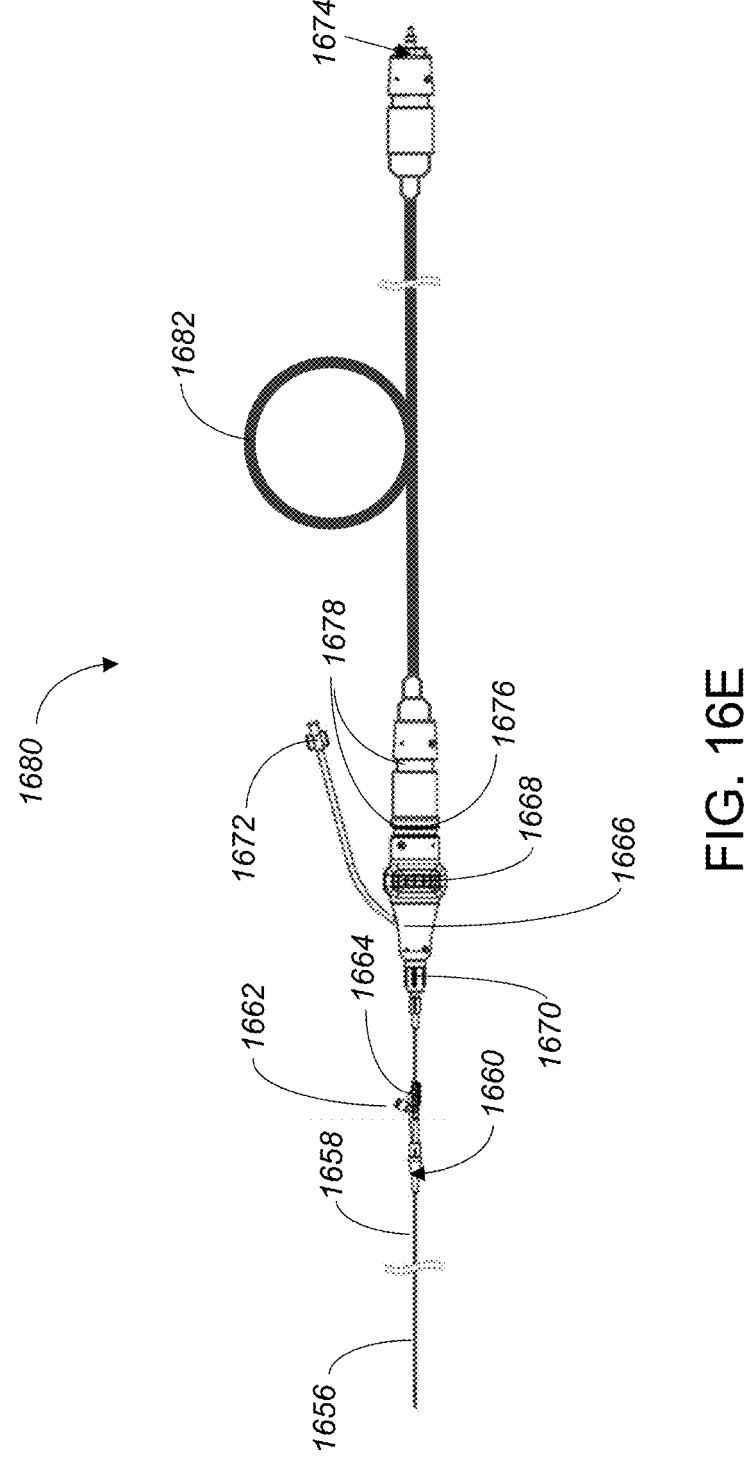
FIG. 16E depicts a variant of the catheter comprising a proximal cable between the catheter housing and connector.

FIG. 16E depicts another embodiment of a catheter 1680 that is similar to catheter 1600 in FIGS. 16A to 16D, except that a fiber optic cable 1682 is provided between the catheter housing 1666 and the fiber optic connector 1674. In this embodiment, the catheter housing 1666 is manipulated by the user like a proximal catheter handle, rather than the combined catheter/sled assembly as depicted in FIGS. 33A to 33M, as the catheter 1600 in FIG. 16A was configured. This cabled catheter 1680 also allows the system to shift the boundary between the sterile and non-sterile environments proximally away from the catheter housing 1666, which may simplify the connection between the catheter connector 1674 and the sled, such that a sterile drape is not required at the junction of the connector 1674 and sled. The length of the cable 1682 may be in the range of 6 inches to 6 feet, or 12 inches to 4 feet, or 1 foot to 3 foot, or 18 inches to 3 feet, for example. permanent part of the imaging driver/sled assembly at the proximal end, with a handle or housing socket at the distal end connected to catheter 1600 in FIG. 16A.

Figure 17:
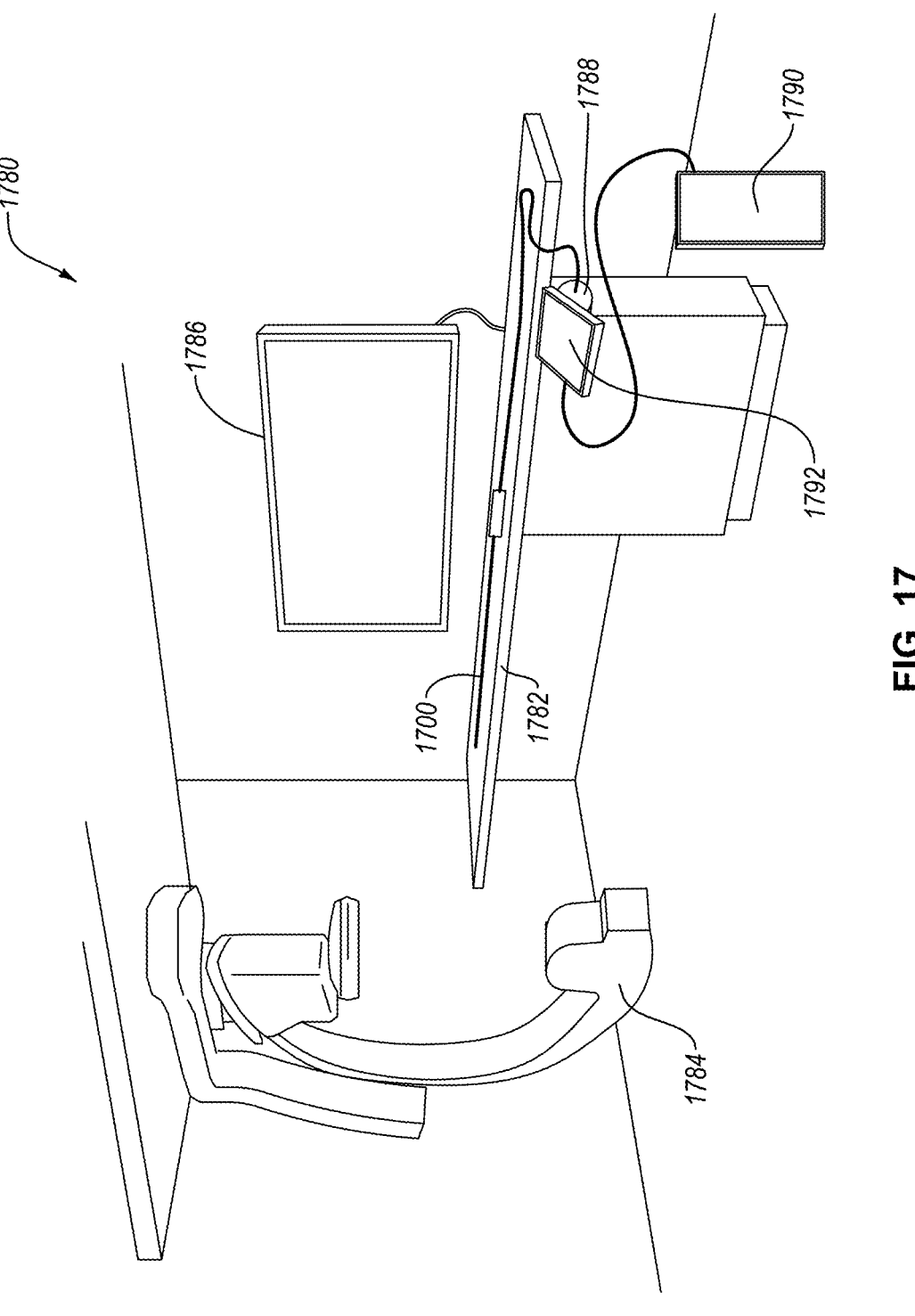
FIG. 17 is an illustration of a system, according to an embodiment.

FIG. 17 is an illustration of a system 1780, according to an embodiment. The system 1780 includes a catheter 1700. The catheter 1700 may include any of the catheters disclosed herein. The system 1780 may also be configured to execute any of the methods disclosed herein.

The system 1780 includes one or more components that facilitate operation of the catheter 1700. For example, the system 1780 may include a bed 1782 or other structure on which a patient may rest of the catheter 1700 is used. The system 1780 may also include an external imaging device 1784 that is configured to image tissue within the body of the patient and the catheter 1700. The external imaging device 1784 may include, for example, a projectional radiography device (e.g., x-ray machine), a magnetic resonance imaging (MRI) machine, the computed topography machine (e.g., CT scanner), and ultrasound device, or any other external imaging device. The system 1780 may also include an imaging display 1786 configured to provide data to the user (e.g., medical practitioner) of the system 1780. The imaging display 1786 may display, for example, images detected by the imaging device of the catheter 1700 and/or images detected by the external imaging device 1784.

The system 1780 may include one or more components configured to operate and/or use data acquired by the catheter 1700. For example, the system 1780 may include an imaging driver 1788. The imaging driver 1788 may be configured to be connected to the catheter 1700, e.g., the image interconnect 1674, such as the DMI fiber optic connector (Diamond SA; Losone, Switzerland). The imaging driver 1788 may also include software that allows the imaging device of the catheter 1700 to communicate with other components of the system 1780, such as at least one of the imaging display 1786, the console 1790, or the touchscreen 1792. The imaging driver 1788 may be physically attached to the touchscreen 1792, or the imaging driver 1788 may be separately situated on the operating table inside or outside the sterile field.

The system 1780 may also include the console 1790 connected or connectable to the catheter 1700. The console 1790 is configured to facilitate operation of the catheter 1700. In an example, the console 1790 may at least one of provide power to the catheter 1700 or light or other stimulus to the catheter 1700 (e.g., via optical cables) when the imaging device requires the light or other stimulus. In an example, the console 1790 may also provide control one or more operations of the catheter 1700 and analyze any data generated by the catheter. In such an example, the console 1790 may further include a housing with a SLED light source or swept laser source output, a graphics processing unit (GPU) for generating output to the touchscreen and optional larger non-touchscreen display, as well as corresponding connecting cable interfaces for the laser source output and the GPU output. The SLED light source or swept laser source output may comprise an imaging source interconnect and an interconnect for an optional aiming beam that is described elsewhere herein. The console 1790 may also include one or more power switches, a locking mechanism (key or keyless) and an emergency stop button or actuator.

Figure 18A:
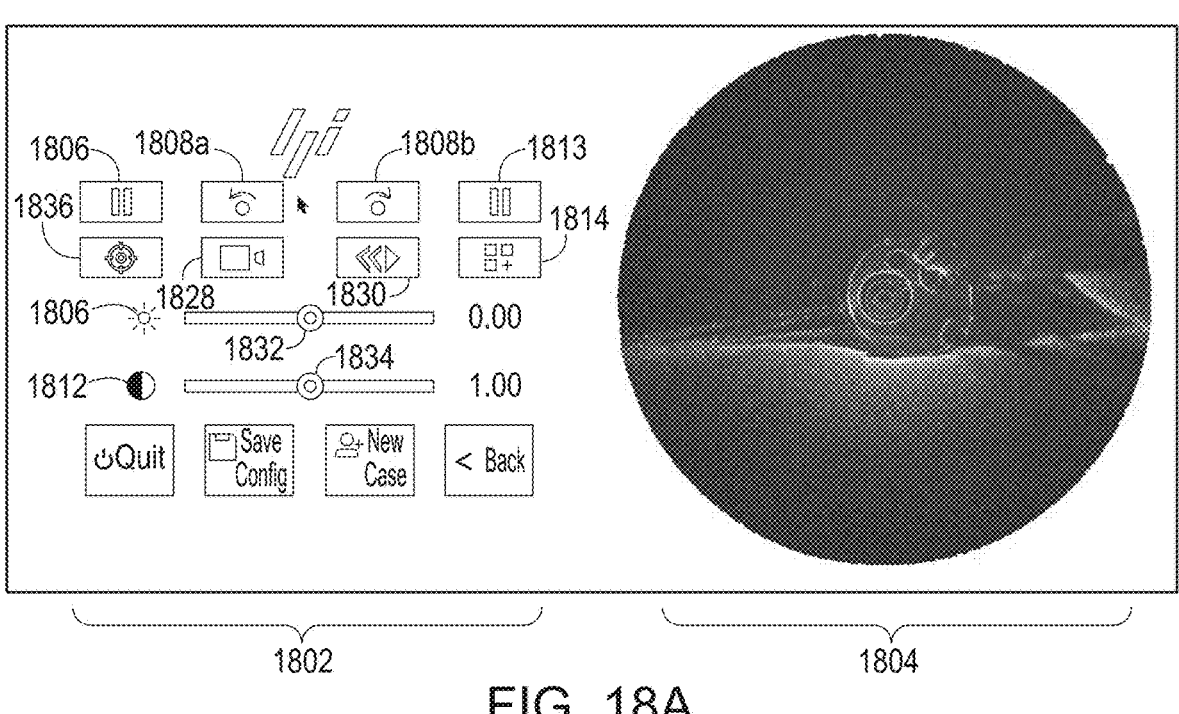
FIGS. 18A and 18B are images of an example graphical user interface that may be used with the touchscreen, according to an embodiment.
Figure 18B:
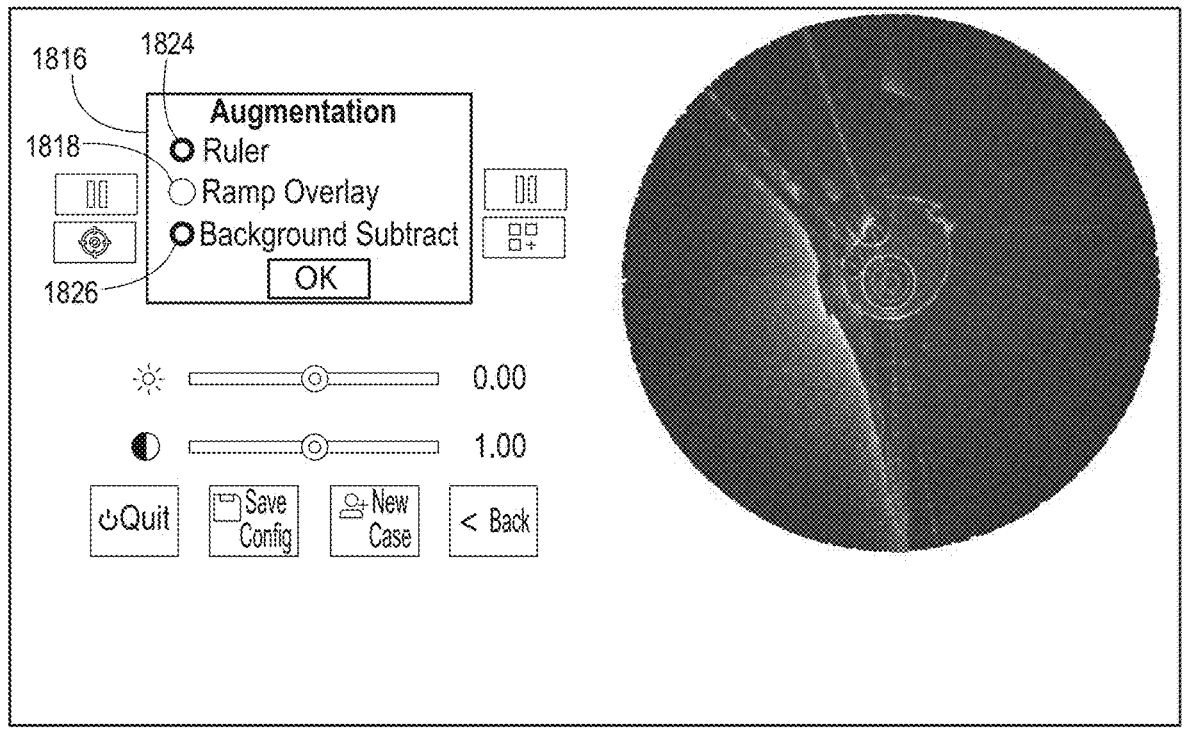

As previously discussed, the system 1780 may include a touchscreen 1792 (e.g., a tablet). The touchscreen 1792 may allow the system 1780 to provide information or control options to the user of the system 1780 and allow the user to at least partially control the operation of the system 1780. The touchscreen 1792 (or a device configured to provide images to the touchscreen 1792 and receive inputs from the touchscreen 1792) may include a graphical user interface that provides information to the user and allows the user to input commands to the system 1780. FIGS. 18A and 18B are images of an example graphical user interface 1800 that may be used with the touchscreen, according to an embodiment. The user interface 1800 includes a command region 1802 that allows the user to interact with the user interface 1800 (e.g., input commands into the user interface 1800) and a display portion 1804 that is configured to provide data or images to the user. For example, the display portion 1804 may provide an image generated by the imaging device of the catheter using the methods previously discussed.

Figure 18D:
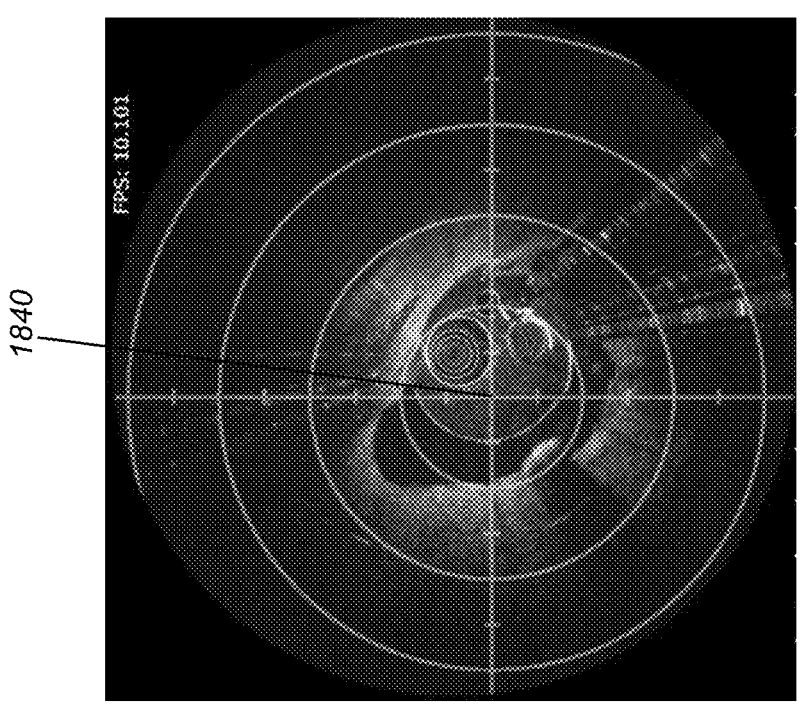
FIGS. 18C and 18D depict the ruler overlay on an OCT image of the touchscreen and secondary display, respectively.
Figure 18C:
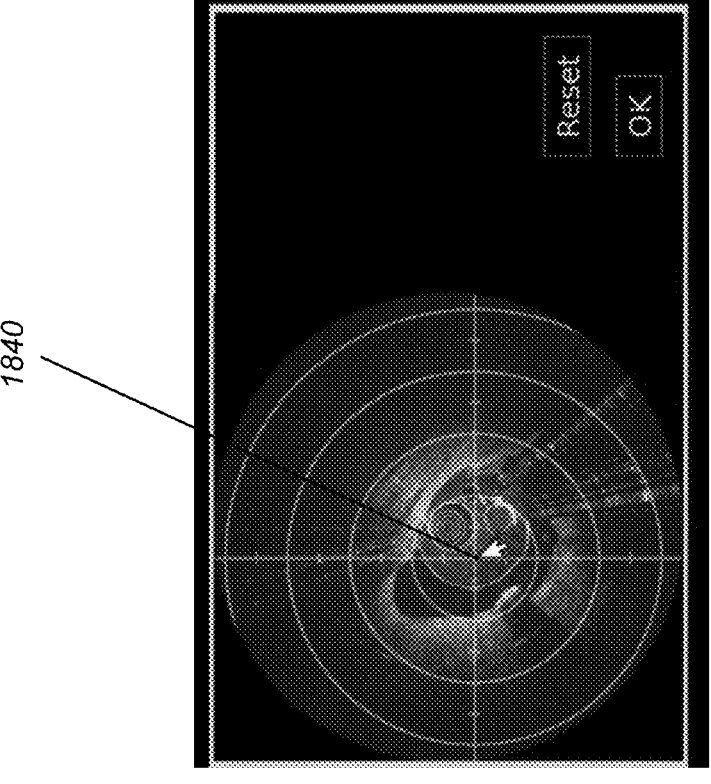

Referring to FIG. 18A, the command region 1802 may include one or more icons displayed thereon that, when pressed by the user, change the image provided in the display portion 1804. Typically, the command region 1802 is displayed on the touchscreen 1792 and the display portion 1804 is displayed on the imaging display 1786. In an example, the icons may include a pause icon 1806 that, when pressed by the user, causes the image provided in the display portion 1804 to show a live feed of the image detected by the imaging device or a stillframe of the live feed. In an example, the icons may include one or more rotating icons 1808*a* and 1808*b* that, when pressed, cause the image provided in the display portion 1804 to rotate. The icons may also include a brightness icon 1810 and a contract icon 1812 that are configured to change the brightness and contrast, respectively, of the image when manipulated by the user. The icons may include an instant replay icon 1813 that, when pressed by the user, causes the display portion 1804 to show a replay of what was previously shown. The icons may also include an augmentation icon 1814. Referring to FIG. 18B, the augmentation icon 1814 may cause the graphical user interface 1800 to display an augmentation box 1816 when pressed. The augmentation box 1816 may include one or more additional icons (e.g., selectable circles). For example, the augmentation box 1816 may include a ramp overlay icon 1818. When pressed, the ramp overlay icon 1818 may superimpose a template on the image. The template may include any of the templates disclosed herein and may illustrate, for example, the off-ramp indicator 1820 and an indicator circle 1822 (as shown). The augmentation box 1816 may also include a ruler icon 1824 that, when pressed, causes a scale to be superimposed onto the image. FIGS. 18C and 18D depict an exemplary ruler overlay 1840 that may be provided on the touchscreen and secondary displays, respectively, comprising an intersecting X and Y axis ruler with 0.5 and/or 1 mm increment markings. In this particular example, each of the rings are 1 mm apart, while the axis marks are 0.5 mm apart. In use, in addition to turning the ruler overlay 1840 on and off via the user interface icon 1824, the user interface may also be movable relative to the OCT image, using the touchscreen or input device (e.g. keyboard, mouse, gesture tracker), which may facilitate measurement of the lumen or other anatomical structure, when the catheter is not at a central location of the lumen or anatomical structure. The augmentation box 1816 may also include a background subtract icon 1826 that subtracts or at least reduces the background detected by the imaging device. Referring back to FIG. 18A, the graphic user interface 1800 may include additional control icons, optionally including but not limited to a video recording start/stop icon 1828, a replay/reloop icon 1830 that replays the last segment of the current video to allow the user to review the procedure, as well as brightness and contrast icon controls 1832 and 1834. The interface may also include icon 1836 to turn on and off an aiming beam 3326, depicted in FIG. 33H, which can be used to confirm the function of the catheter, the light source, and the optical coupling between them, prior to insertion of the catheter into the patient.

Referring back to FIG. 17, the system 1780 may include one or more input and output devices other than or in addition to the touchscreen 1788. In an example, as illustrated the system 1780 may include the imaging display 1786. In an example, the system 1780 may include a keyboard, mouse, joystick, or other input device that allows the user to modify the image detected by the imaging device.

The catheter systems disclosed herein are typically used with coronary and other peripheral vasculature, including arterial and venous vasculature, but in other variations, the re-entry may be used with other non-vascular body lumens, e.g. lymphatic system, biliary tree, etc., as well as cerebral or neurovascular structures. Although the catheter systems include an imaging device like OCT or ultrasound, the systems may also be used in conjunction with an external visualization or imaging system, such as a fluoroscopy system in a catheterization laboratory or interventional radiology suite.

Figure 19:
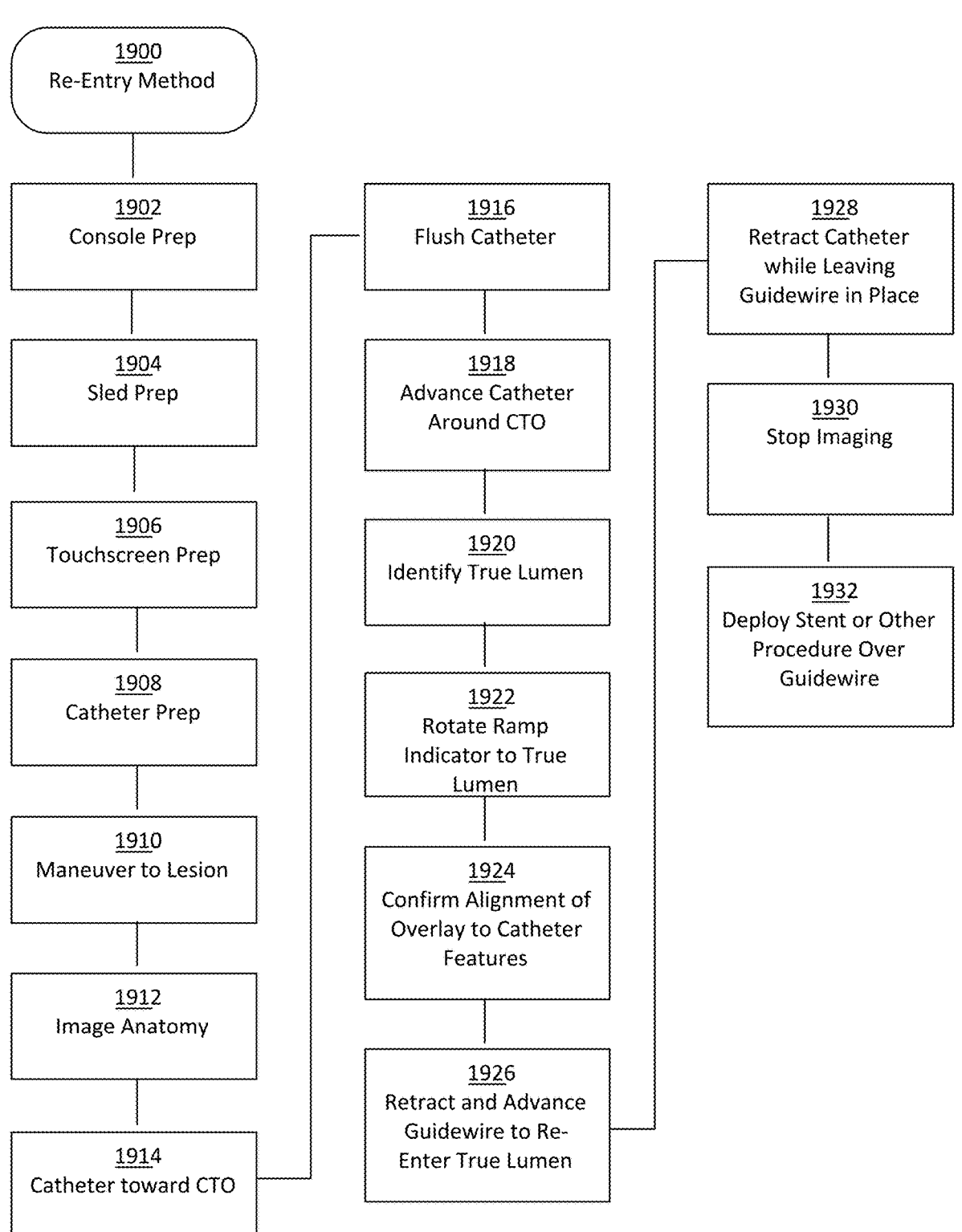
FIG. 19 is a flow chart of general system operation during a re-entry procedure.

In one example, a method of using re-entry catheter system is provided, as depicted in FIG. 19. Generally, the method 1900 includes console preparation 1902, sled preparation 1904, touchscreen preparation 1906, and catheter preparation 1908. The catheter is then maneuvered to the lesion 1910 under fluoroscopic guidance. Using the imaging system of the catheter 1912, including imager position knob and catheter rotation adapter, the surrounding anatomy is visualized. The catheter is advanced 1914 closer to the chronic total occlusion ("CTO"). The catheter is flushed with saline 1916 if necessarily or desired, which is visible on OCT imaging. The catheter is then advanced 1918 to and around the CTO, into the subintimal space. Once passed the CTO, the OCT imaging is used to identify 1920 the true lumen pulsating region and adventitia fibrous/honeycomb layer region. Using the imaging overlay, the guidewire ramp indicator is then rotated 1922 toward the true lumen and away from the pericardium or adventitia, to avoid the risk of perforation. Before advancing the guidewire, confirm that the overlay augmentation of the flush lumen circle is concentric with the OCT image of the flush lumen 1924. The guidewire can then be advanced and re-entry into the true lumen is confirmed by the OCT imaging 1926. Once the guidewire is positioned, the catheter is retracted 1928 while maintaining the position of the guidewire. Once the catheter is removed, the imaging system is turned off 1930. A stent may then be deployed 1932 or other procedure performed over the guidewire.

Exemplary Detailed Procedure

The patient and the procedure area is prepped and draped in the usual sterile fashion. A clear/transparent sterile drape may also be applied to the non-sterile touchscreen of the console. The touchscreen drape may comprise a silicone adhesive, hook-and-loop interface or snap buttons to facilitate attachment. The drape may also be used to grasp the touchscreen in a sterile fashion for repositioning or attachment to a rail of the procedure bed or fluoroscopy system.

Figures 33A, 33B:
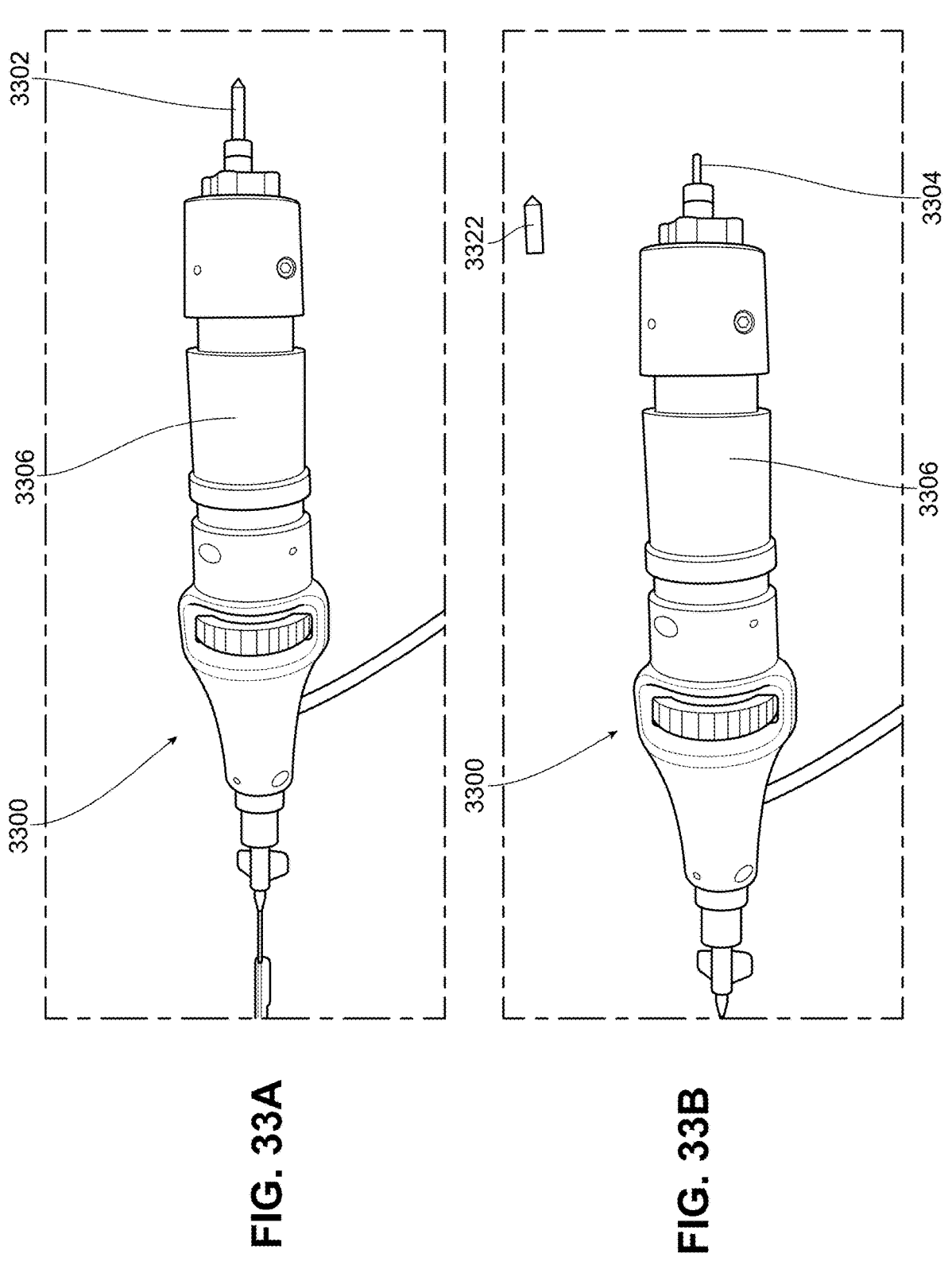
FIGS. 33A to 33M depict exemplary preparation steps for using the OCT imaging system.
Figures 33C, 33D:
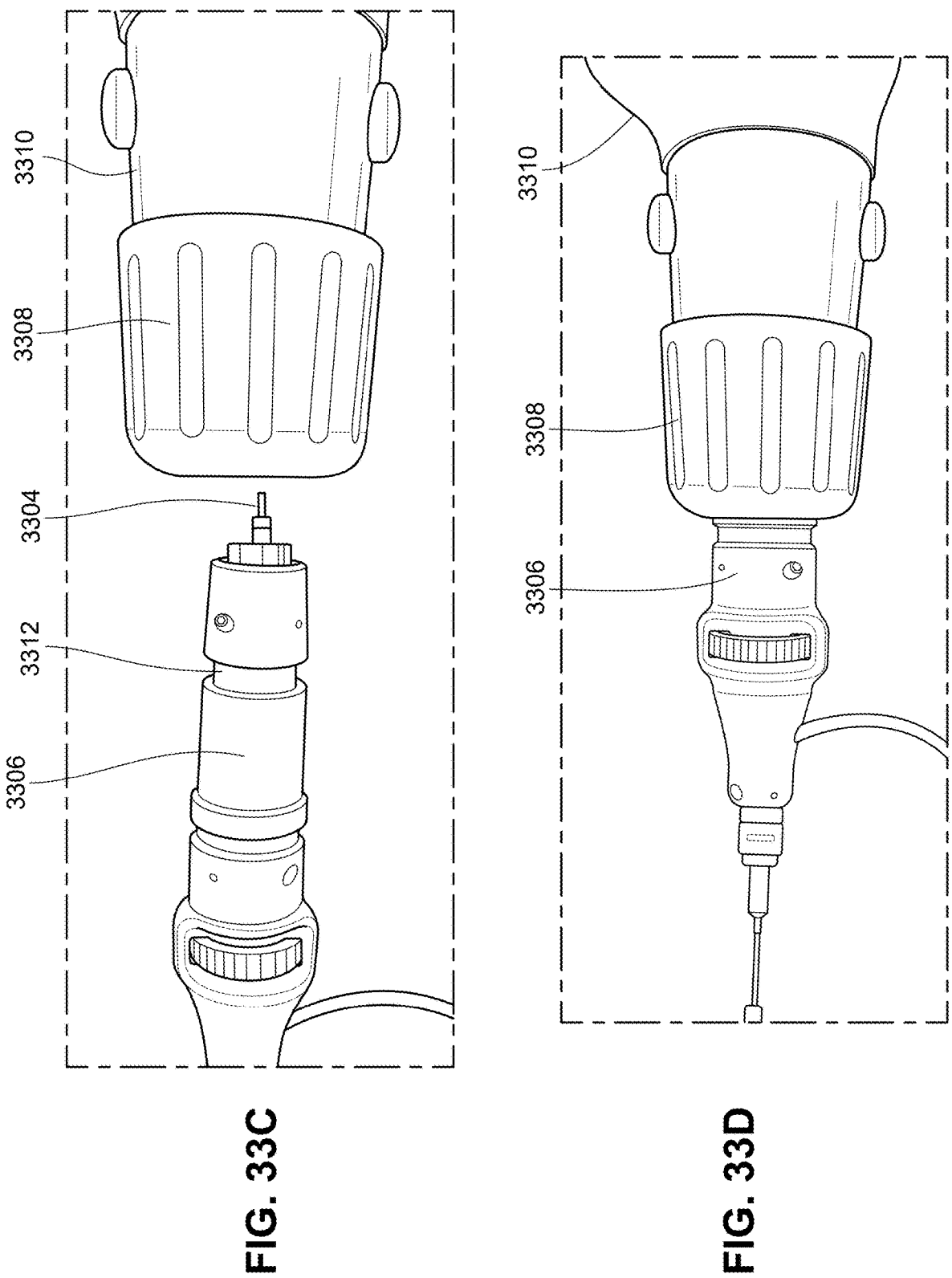
Figure 33E:
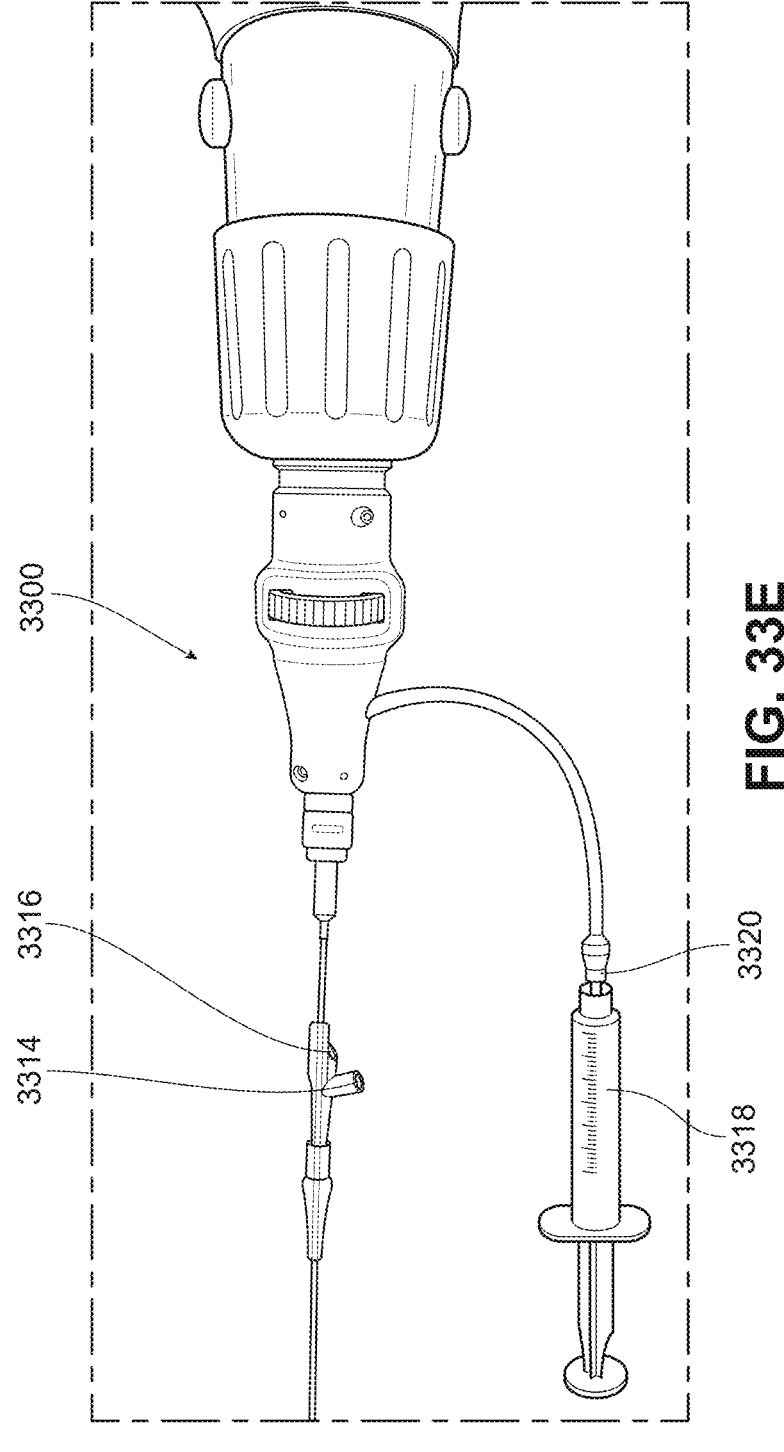

The catheter 3300 is inspected for damage, and using sterile technique, is removed from its packaging and transferred to the sterile field for further inspection. The protective cap 3302 that covers the proximal optical fiber connector 3304 of the catheter housing 3306 is removed (FIGS. 33A and 33B). The proximal optical fiber connector 3304 may be a standard 2.5 mm ferrule. The catheter housing 3306 and connector 3304 is then inserted through the cap 3308 and into to the sled 3310 (FIG. 33C) until the catheter housing is fully attached via the circumferential recess 3312 (FIG. 33D). The interface between the catheter housing 3306 and sled 3310 may be configured to provide visual, audible and/or via tactile feedback to indicate engagement, via surface indicia, a latch, or change in resistance, for example. The catheter shaft is then hydrated in sterile saline for a period of time, e.g. 20 seconds to 120 seconds, 30 seconds to 60 seconds, or 30 seconds to 45 seconds. Using a syringe (e.g., 5 cc or 10 cc), the catheter 3300 may be flushed with sterile heparinized saline using the guidewire lumen flush port 3314 while blocking the guidewire introducer port 3316, and verifying patency with saline flow out of the distal end of the catheter 3320. Blocking of the guidewire introducer port 3318 may be performed using the user's finger. A hemostatic valve may be optionally attached to the guidewire lumen flush port and/or introducer port to block or resist leakage. A syringe 3318 is then attached to the imaging lumen port 3320 and to verify that fluid exists the distal tip as well (FIG. 33E).

After reconfirming that the console has been turned on, the catheter is then tested by selecting and entering case information on the touchscreen. This may include catheter specific information, such as the catheter identifier or serial number. The catheter user interface is then available. Various healthcare record information may be entered and edited on a data entry screen, e.g. patient ID, case ID, site ID, catheter serial number, etc. After this data entry, the catheter user interface may then change to the catheter control screen (FIG. 18A), with various exemplary catheter control elements as described elsewhere herein. Various catheter controls and interface elements are tested and/or configured before beginning the procedure. To initiate imaging, an actuator, .e.g. button 3322, on the sled 3310 may be activated (FIG. 33F), and the rotation of the imager within the catheter 3300 is confirmed via the sector view on the system display. In some variations, an indicator light provided on the system or in the actuator button, and may glow with a first color (e.g. white or green color) if working correctly, or may provide a warning (red color, or flash) if a problem with imager rotation are detected by sensor and/or by the image output itself. In an issue was detected, the catheter 3300 can be detached and released from the sled 3310 by actuating a detachment latch or button(s) 3324a and 3324b (FIG. 33G) and then reconnected to reattempt and confirm proper mounting and functioning. Tactile and/or audible feedback may be confirmed to ensure proper mounting, and then activation of the imager can be reinitiated. Image quality and continuity of the light source to the end region of the catheter 3300 can be tested and confirmed, by turning on the aiming beam 3322 (FIG. 33H) via the aiming beam icon 1826 of the user interface (FIG. 18A) to check for visible light emission from the end region of the catheter 3300. The catheter 3300 may need to be replaced if the aiming beam 1826 is not seen or is very dim.

Figure 33F:
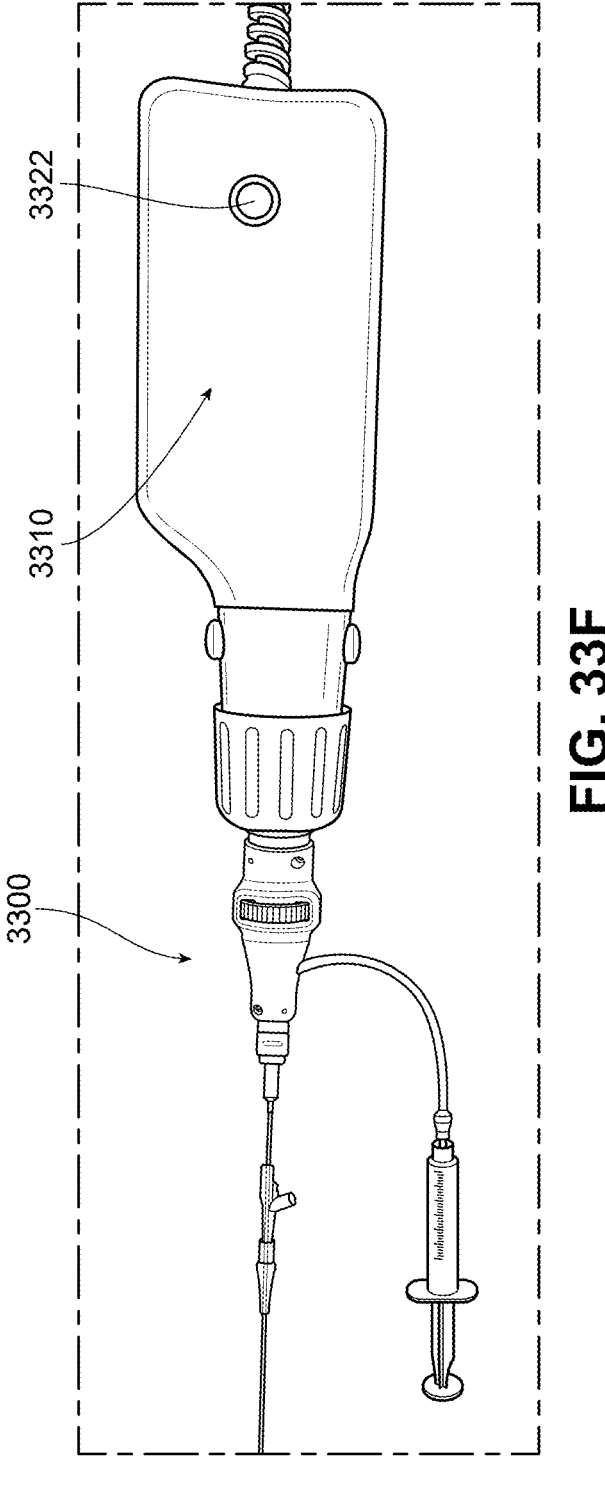
Figures 33G, 33H:
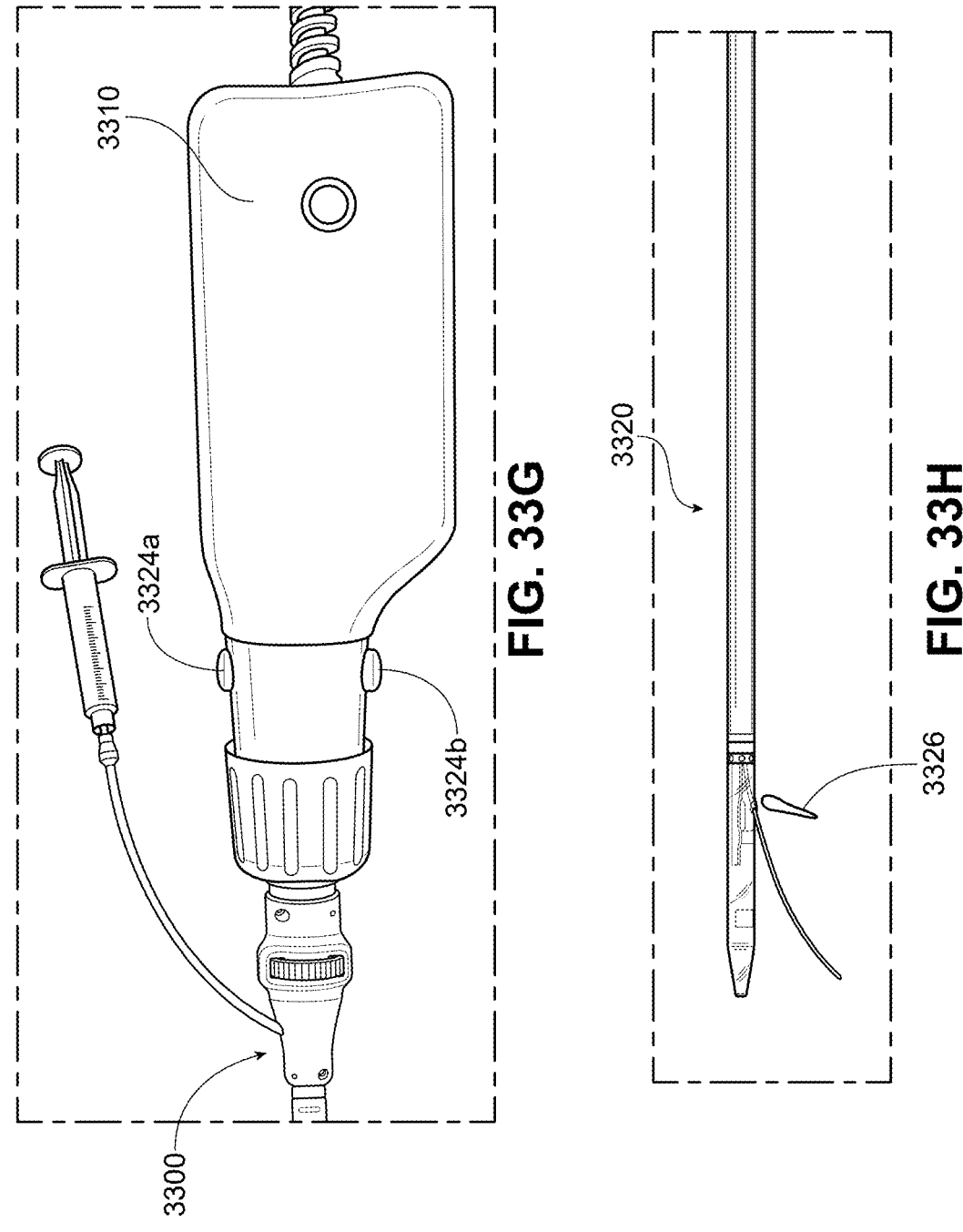
Figure 33I:
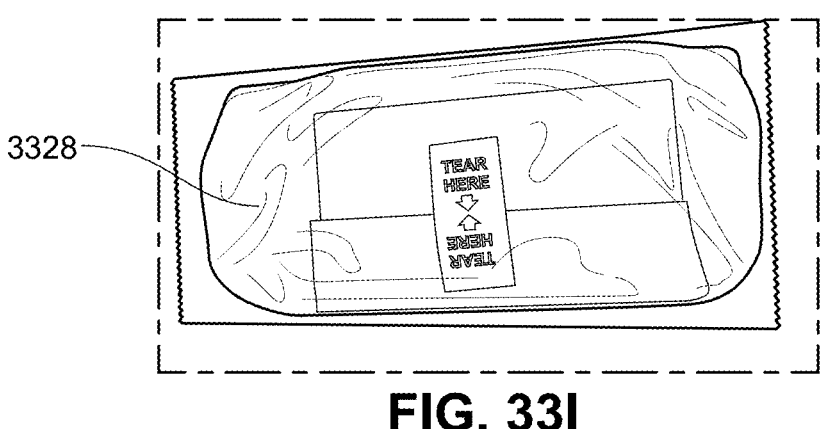
Figure 33J:
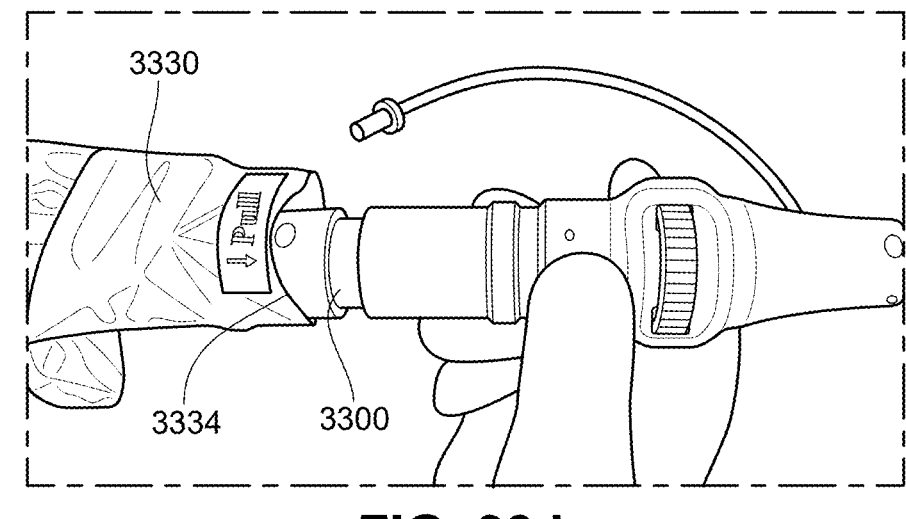
Figure 33K:
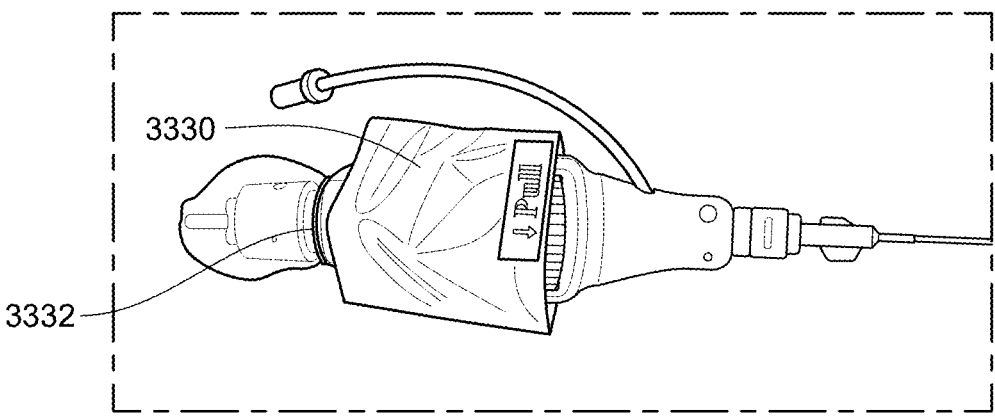

Before inserting the catheter 3300 into the patient, the sled 3310 and catheter 3300 should be turned off by re-actuating the sled button 3318 (FIG. 33F). The light of the sled button 3318 should turn off and the rotation mechanism within the sled should stop spinning. The catheter 3300 is then detached from the sled 3310 via the detachment buttons 3320a/3320b. The exposed connector 3304 should be recapped using the protective cap 3302. Because the proximal end of the catheter 3300 is no longer sterile, having been in contact with the sled 3310, the catheter 3300 will need to be covered to maintain or protect the sterile field. In FIGS. 33I to 33K, a sterile probe cover package 3328 is opened, containing a plastic cover 3330 and an elastic or rubber band 3332. The sterile end 3334 of the cover 3330 is held and the cover 3330 is pushed over the proximal end of the catheter 3300 (FIG. 33J). The cover 3330 is then secured to the catheter 3300 via the rubber band 3332 around a recess of the catheter 3300 (FIG. 33K).

The catheter is then advanced into the patient under visual guidance, e.g. fluoroscopy, through an inserted sheath and over a guide wire to the target lesion site. The guidewire lumen of the catheter is configured to accommodate a standard 0.014" guidewire, but in other variations, other guidewire sizes may be accommodated. In this example, the guidewire has a minimum length of 180 cm, to be used with a 6 F to 8 F trapper, 7 F sheath, and 7 F guiding catheter (minimum 0.081"). In another example, if the guidewire is paired with a guide extension catheter, e.g. TRAPLINER® guide extension catheter (Teleflex; Morrisville, NC), an 8 F TRAPLINER® catheter should be used along with an 8 F sheath, and a 8 F guiding catheter. If no trapper or TRAPLINER® guide extension catheter is used, a 300 cm guidewire should be used to ensure guidewire position.

The tip of the catheter is observed visually via fluoroscopy as the catheter is advanced within the guiding catheter inserted into the patient. Advancement is stopped when the catheter tip is located just proximal to the end of the guiding catheter. The sterile cover 3330 and the protective cap 3302 is then removed from the connector 3304 so that the catheter 3300 can be reattached to the sled 3310, as depicted in FIG. 33F. The system is reactivated via the sled button 3322, and the recording icon 1828 on the user interface (FIG. 18A). Using the imaging to visualize the vasculature during the procedure on either the touchscreen or secondary display connected to the system. The imager knob 3336 of the catheter 3300 in FIG. 33L can be used to adjust the longitudinal position of the imager along the nosecone to the ramp around the side port of the catheter. The imager knob 3336 may also be used to advance or retract the imager to visualize the ramp and/or guidewire lumen. The rotation knob or adapter 3338 on the catheter 3300 may also be used to rotate the catheter clockwise or counterclockwise, to orient the guidewire and guidewire ramp toward the direction of the true lumen.

Figures 33L, 33M:
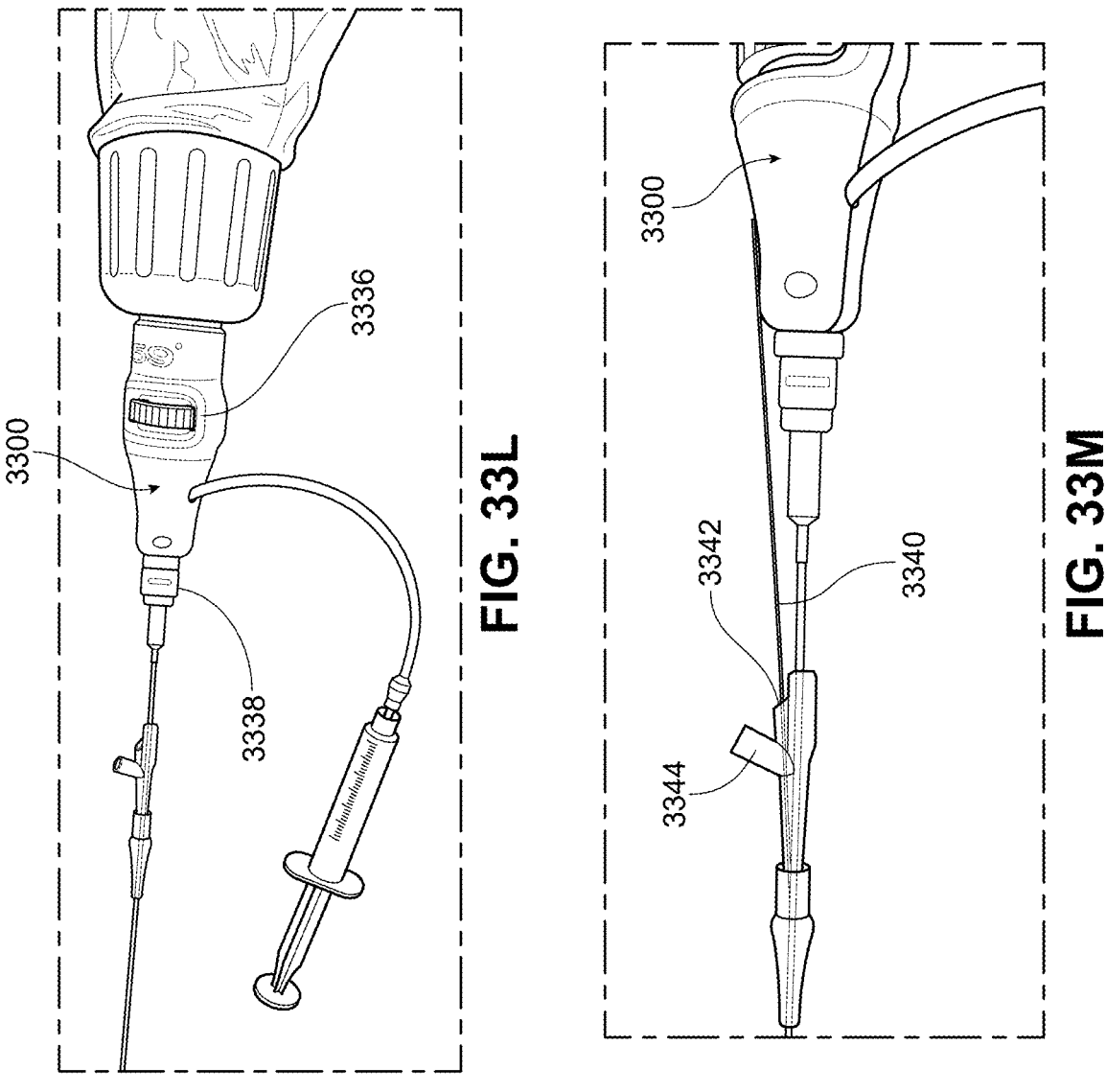
Figure 34B:
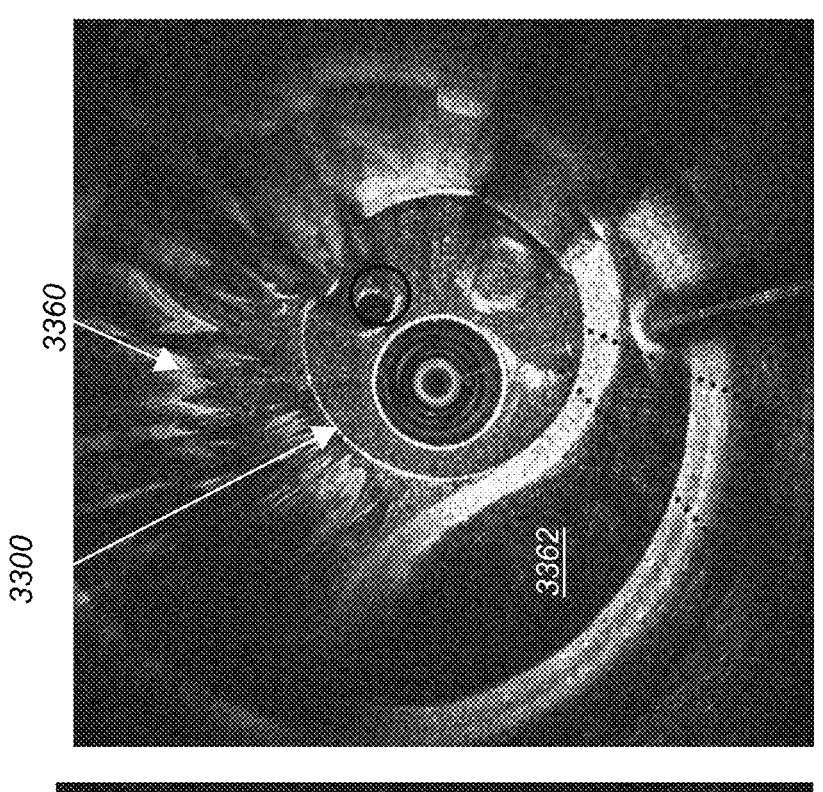
FIGS. 34A to 34F depict exemplary OCT images acquired during use of the OCT imaging system.
Figure 34A:
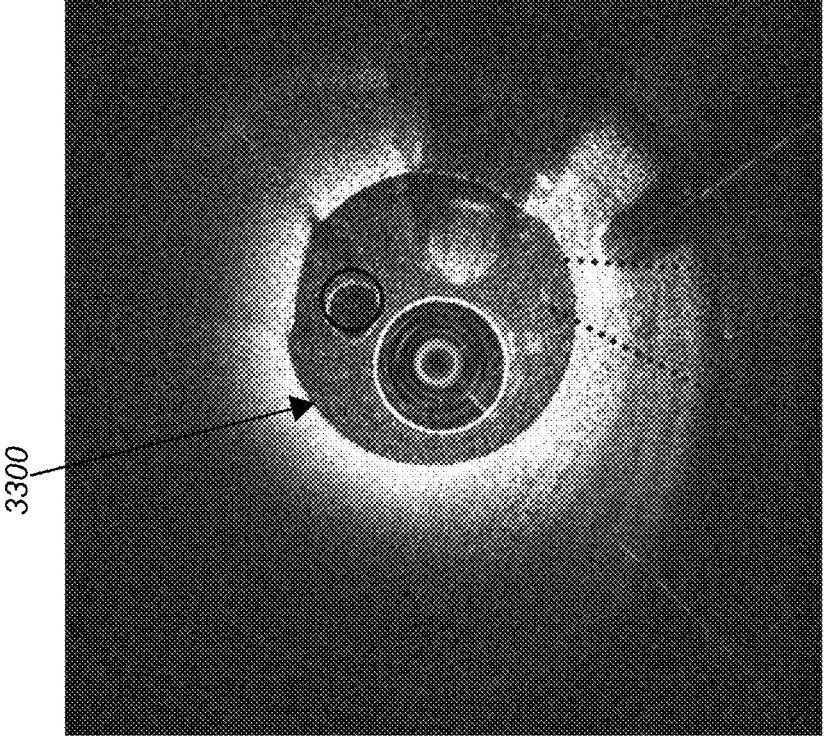

The catheter is then advanced over the guidewire toward the target CTO lesion. Some tactile resistance may be felt or detected by the user if the guidewire advanced into the subintimal space. Fluoroscopic visualization is used during advancement to confirm the catheter position and the end of the guidewire, relative to the CTO lesion. Once the distal end of the catheter is in the vicinity of the CTO lesion, the distal end of the catheter should also be close to the distal end of the guidewire. The proximal end of the guidewire 3340 should be protruding through the introducer port 3342 at the proximal region of the catheter 3300, as illustrated in FIG. 33M. A localized flush in the imaging area can be performed via the guidewire lumen flush port 3344 adjacent to the guidewire introducer port 3342. A larger volume flush can also be performed via the flush port of the guiding catheter when needed, e.g. in larger vessels. FIG. 34A depicts an exemplary OCT image with blood in the visual field, acting as an optical scatting medium at the operating wavelength of the OCT imaging system, thus exhibiting a general haziness, cloudiness or fogginess in the image. FIG. 34B depicts an exemplary OCT image with a reduced amount of blood in the visual field, resulting from a saline flush through the guidewire lumen flush port. The vascular structures around the catheter are more visible. The saline flush itself can be confirmed via the starburst-like region 3360 in the OCT image, resulting from the fluid dynamics around the catheter 3300. FIG. 34B also depicts the subintimal dissection from the catheter, with the true lumen 3362 seen as a flattened pancake shape extending from the 5 o'clock to 9 o'clock region of the image.

Figure 34C:
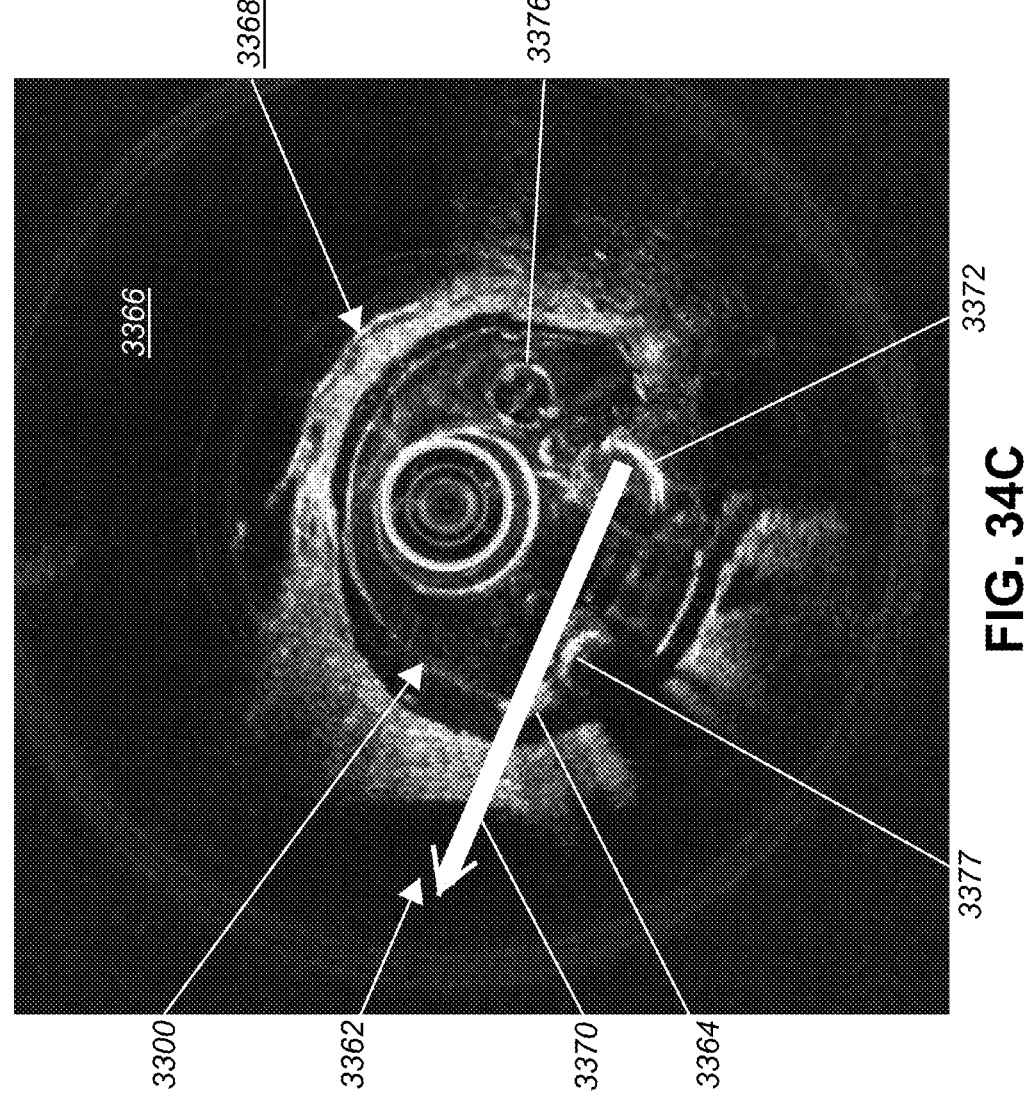

To re-enter the true lumen from the subintimal space, the catheter is advanced toward the lesion site. The catheter tip/ramp orientation is visually confirmed prior to advancing the catheter. The user confirm the location of the true lumen and identify the desired re-entry location or path based on the OCT image. Referring to FIG. 34C, once the true lumen 3362 location is identified, the catheter 3300 is rotated using the rotation adapter to aim the guidewire ramp 3364 toward true lumen 3362 and away from the pericardium 3366 and adventitia 3368 of the vessel. The direction of the guidewire trajectory 3370 can be determined by the axis between the guidewire lumen 3372 and the guidewire ramp 3364. This can also be confirmed based on its relative orientation to other visualized structures of the catheter 3320, such as the indicator lumen or flush lumen 3376, and by the orientation of the guidewire 3377 as it is advanced through the ramp 3364.

Figure 34E:
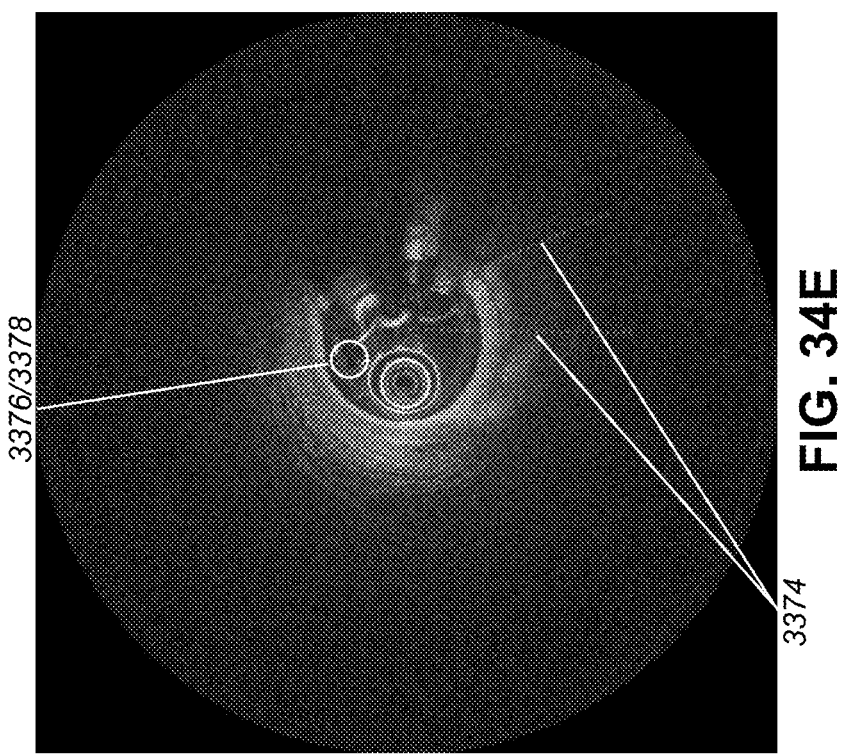
Figure 34D:
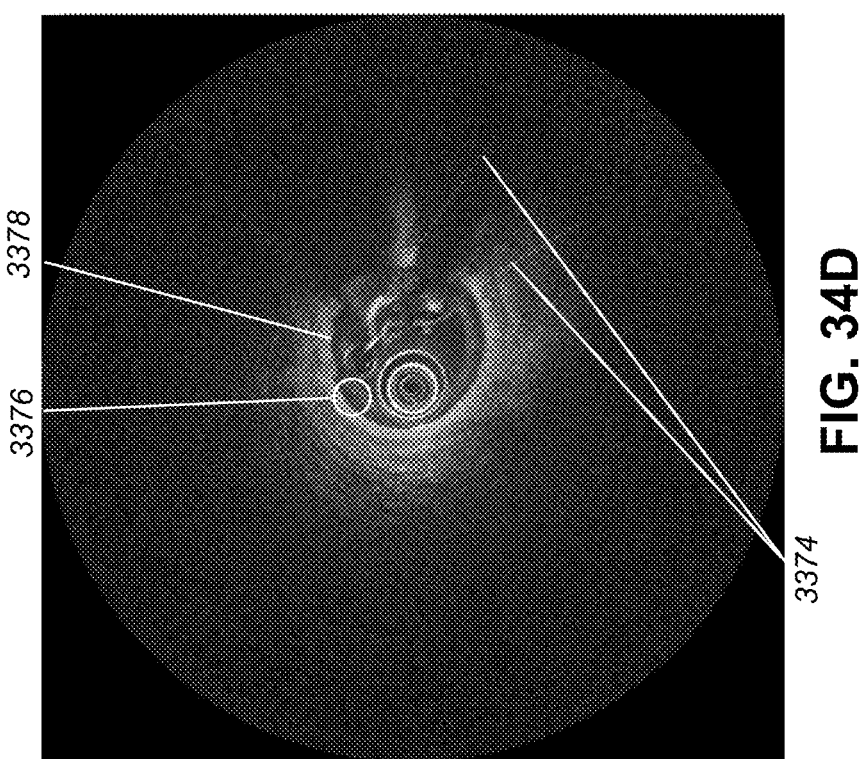

The ramp indicator overlay 3374 and a circular indicator 3376 of the flush lumen 3378 or indicator lumen (FIGS. 34D and 34E) can be turned on and off via the ramp indicator icon 1818 of the augmentation menu 1816 (FIG. 18B). When turned on, three potential states may occur. If the system is not confident in identifying the catheter orientation, no overlay graphics will be provided. If the system is confident in its determination of catheter orientation, a circle indicator 3376 and the frustoconical ramp indicator overlay 3374 will appear on the OCT images (FIGS. 34D and 34E). As shown in FIG. 34D, however, the system may be confident but still err in showing the predicted trajectory of the guidewire ramp/guidewire trajectory, as exhibited by the offset between the circular indicator 3376 and the flush or indicator lumen 3378, while FIG. 34E depicts a greater alignment between the circular indicator 3376 and the flush lumen 3378, such that the ramp indicator 3374 in FIG. 34E is likely to be more accurate. When using or relying on the ramp indicator 3374, the user should confirm alignment between the circular indicator 3376 and the flush lumen 3378, and also make a final and independent assessment of the guidewire trajectory before and during guidewire advancement.

Figures 34F, 34G:
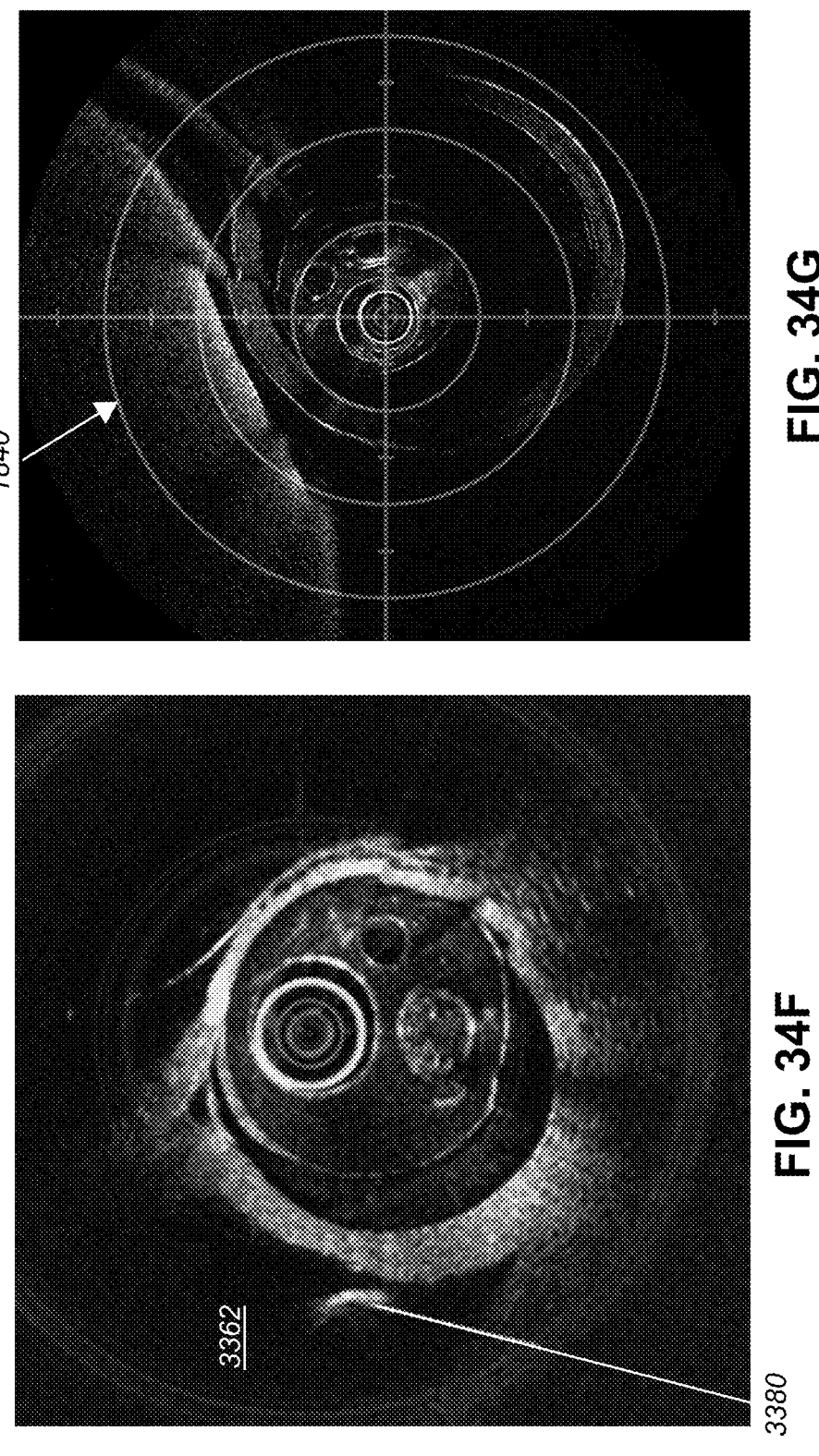
FIG. 34G depicts the ruler overlay on an OCT image.

Once the user has made the decision to deploy or advance the guidewire toward the true lumen, the guidewire is retracted until the distal end of the guidewire is located in the common lumen of the catheter, proximal to the ramp lumen, and then advanced through the ramp lumen and into the true lumen. FIG. 34F depicts an OCT image of a successful re-entry of the guidewire 3380 from the subintimal space and into the true lumen 3362, where the guidewire 3380 is visible within the true lumen 3362. The user should confirm re-entry via fluoroscopy, with contrast injection under fluoroscopy showing artery or side branch revascularization. Once the site and direction of re-entry is determined, the user may also replace or exchange the existing guidewire via the guidewire introducer port 3342 in FIG. 33M, depending on the user decision as to whether a different type and/or different stiffness of guidewire is appropriate. If the guidewire is stuck in the catheter during advancement or retraction, the guidewire lumen may be flushed through the guidewire lumen flush port 3344. During pullback or retraction of the guidewire back into the catheter, the user should stop if any resistance is encountered and should assess the cause of the resistance. If the guidewire cannot be freed with flushing of heparinized saline through the guidewire lumen flush port 3344, or if the guidewire appears to prolapse or kink, the guidewire should not be pulled back, and instead the guidewire and catheter should be withdrawn slowly and gently under fluoroscopic guidance together as a single unit or assembly.

Upon proper placement of the guidewire, the catheter should be retracted while leaving the guidewire in place using standard catheterization lab procedures for catheter removal or exchange. Once the catheter is withdrawn from the body, the activation button 3322 on the sled 3310 is de-actuated to stop imaging and to turn off the motor, per FIG. 33F, and the catheter 3300 is disconnected by actuating the detachment latch or buttons 3324a/3324b per FIG. 33G. The catheter is then discarded per standard disposal techniques once the catheter is removed from the sterile field. Alternatively, the operator may choose to de-actuate the imaging and motor and disconnect the catheter from the sled 3310 before retracting the catheter while keeping the guidewire in position.

As indicated during the procedure, to size the artery or lumen, the ruler overlay 1840, depicted in FIGS. 18C, 18D and 34G, may turned on by selecting the ruler icon 1824 depicted in FIG. 18B. FIG. 23G depicted the crosshatch pattern overlaying the OCT image, with 0.5 mm accuracy in water/saline environment. As noted earlier, the ruler overlay 1840 comprises ring indicators that are 1 mm apart and axis markings in 0.5 mm increments. In the particular example depicted in FIG. 34G, the ruler overlay 1840 has an imager field-of-view with a radius/diameter greater than 3.5 mm and 7 mm, respectively. Generally, arteries are filled with optically scattering media, such as blood, which obscure OCT signals beyond the catheter cross-section. Imaging resolution may be improved by transiently or temporarily displacing the surrounding blood by flushing optically clear fluid through the guiding catheter flush port and/or the guidewire lumen flush port, preferably with 50/50 saline/contrast in order to expose the surrounding arterial structures. By flushing, the image resolution may be improved and it may make it easier to measure the inner diameter of an artery or lumen with the assistance of the ruler overlay 1840.

Case Report

Figures 10A, 10B, 10C, 10D:
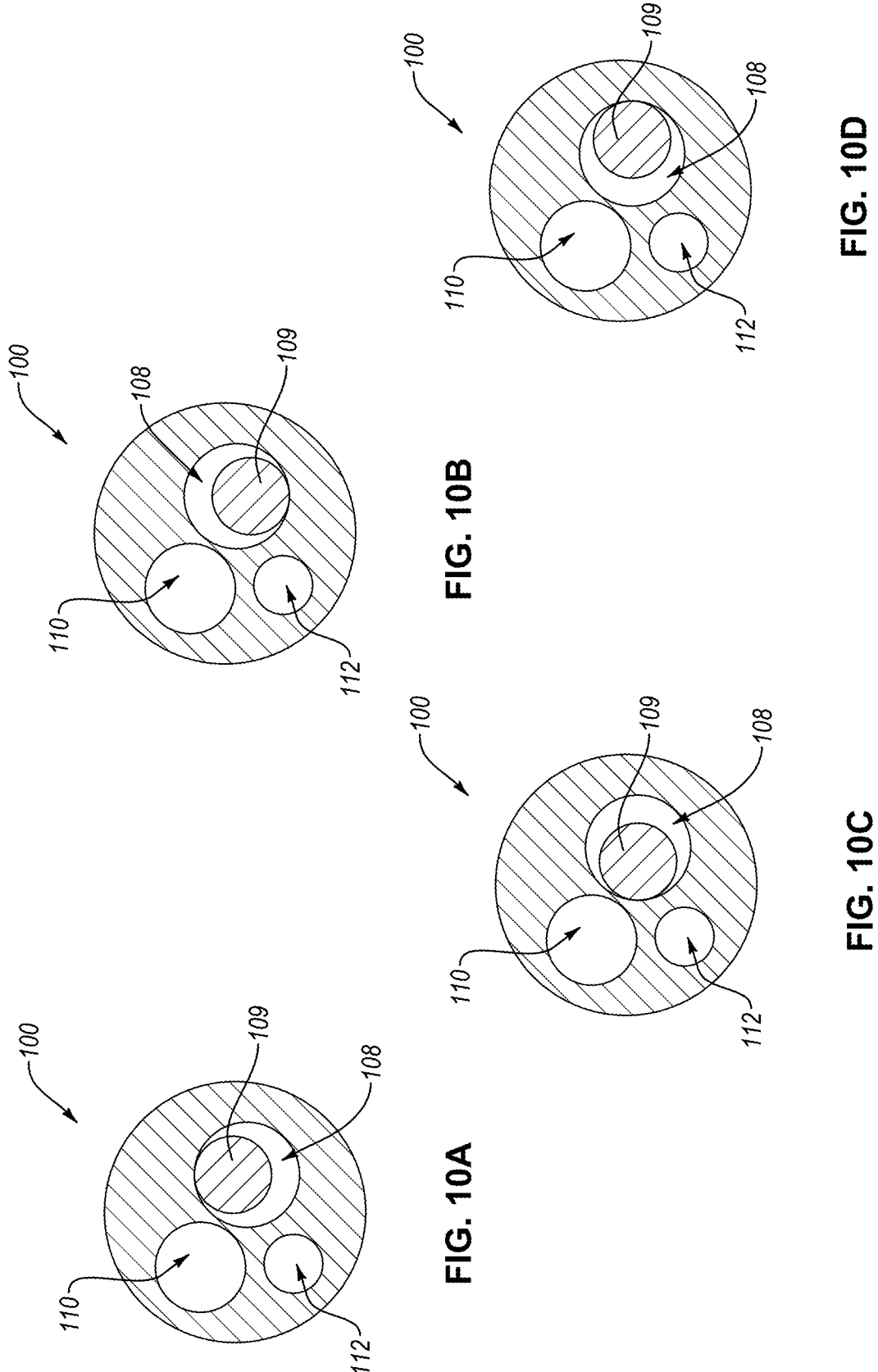
FIGS. 10A to 10D are schematics illustrating how moving the OCT imaging device in the imaging lumen changes the location of different components of the catheter relative to the center of the OCT imaging device, according to an embodiment.
Figure 20A:
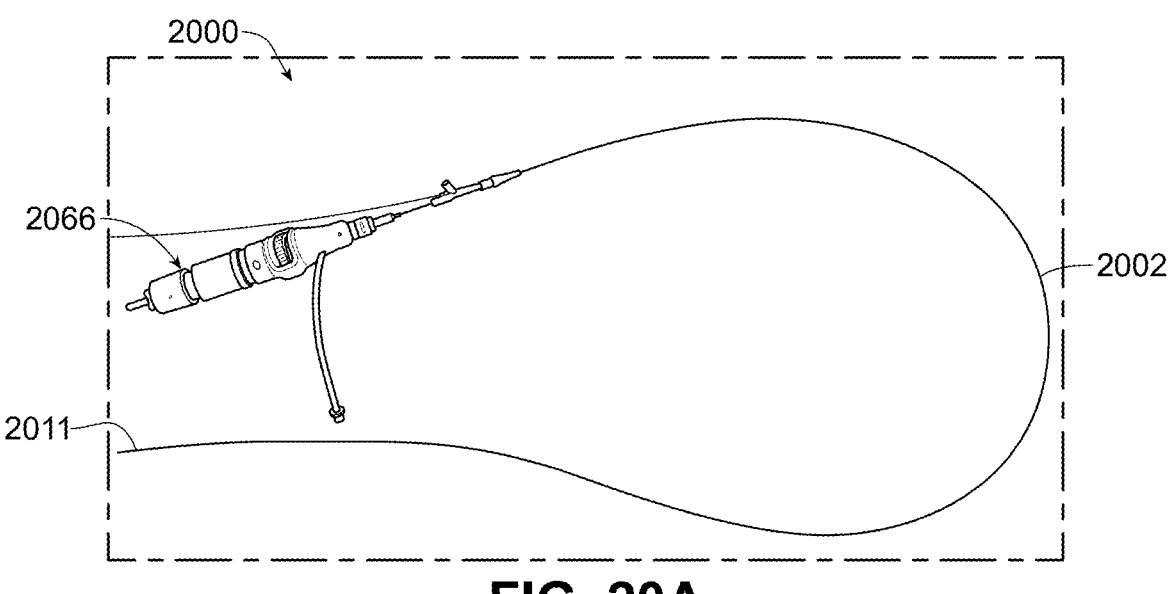
FIGS. 20A to 20C depicts overall, proximal and distal plan views of another exemplary catheter system comprising a 4-Fr image-guided re-entry catheter.
Figure 20B:
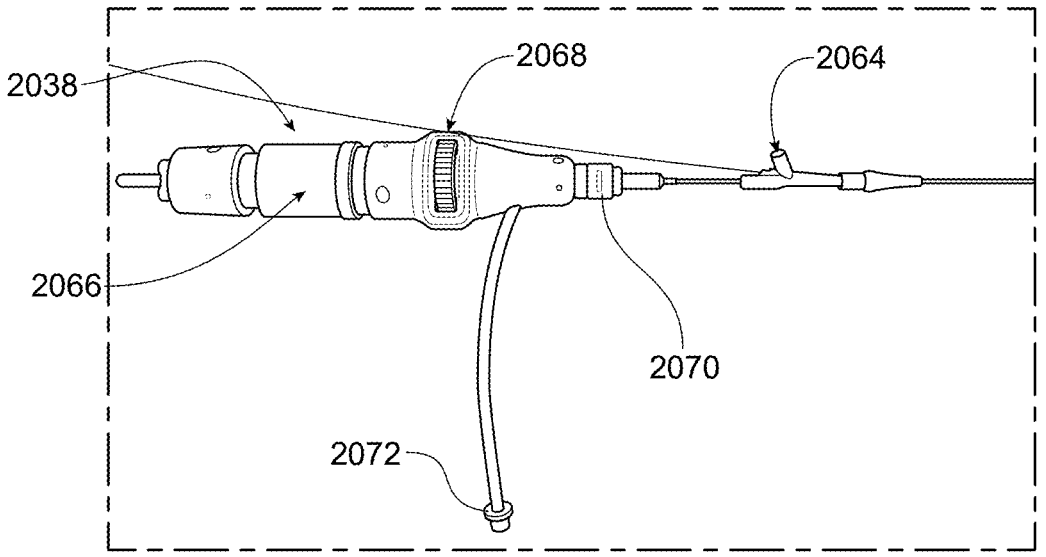
Figure 20C:
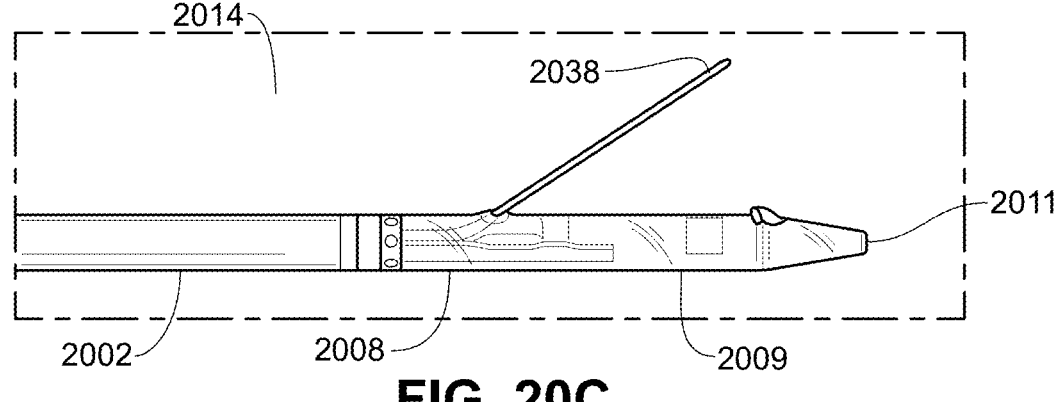

A first in human case of successful contemporary ADR using an exemplary OCT guided re-entry catheter was performed, that utilized real-time high-resolution visualization with image augmentation and precision steering and advancement of a guidewire. FIGS. 20A to 20C depicts the catheter 2000, comprising a proximal housing 2066 and catheter body 2002 with a distal end 2011. Referring to FIG. 10B, the proximal housing 2066 includes an imager position adjustment knob or actuator 2068, a flush port 2072, a catheter orientation knob or controller 2070, and a guidewire introducer 2064 into which a guidewire 2038 has been inserted. At the distal end 2011 of the catheter body 2002, depicted in FIG. 10C, the guidewire 2038 is depicted extending out of a side port 2014, with the imaging device 2009 visible in the imaging lumen 1222. An easily maneuverable and torqueable imaging catheter facilitates the operator to steer and aim a 0.014″ guidewire out the side port in any continuous orientation with better than 5-degree precision.

Figure 21A:
FIGS. 21A to 21E depict fluoroscopic images of the therapeutic procedure.
Figure 21B:
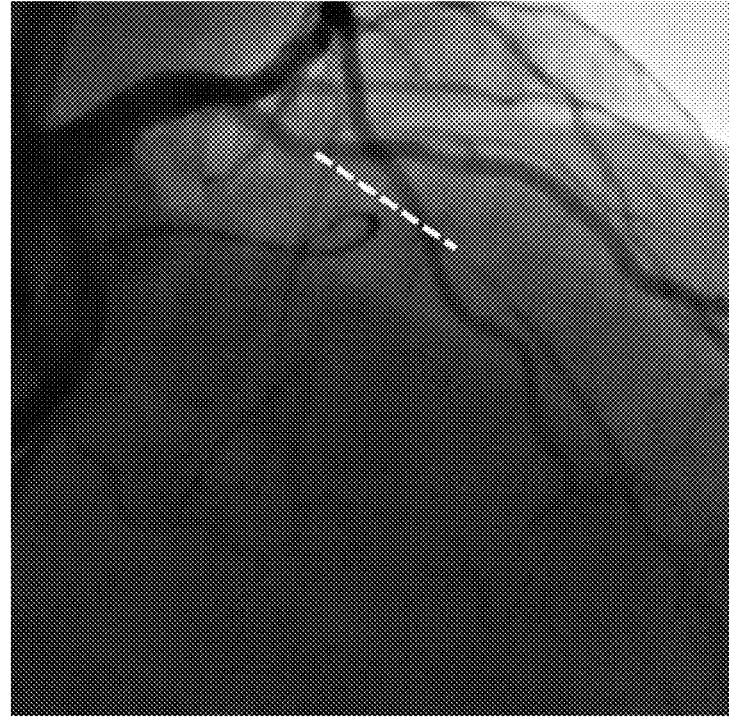
Figure 21C:
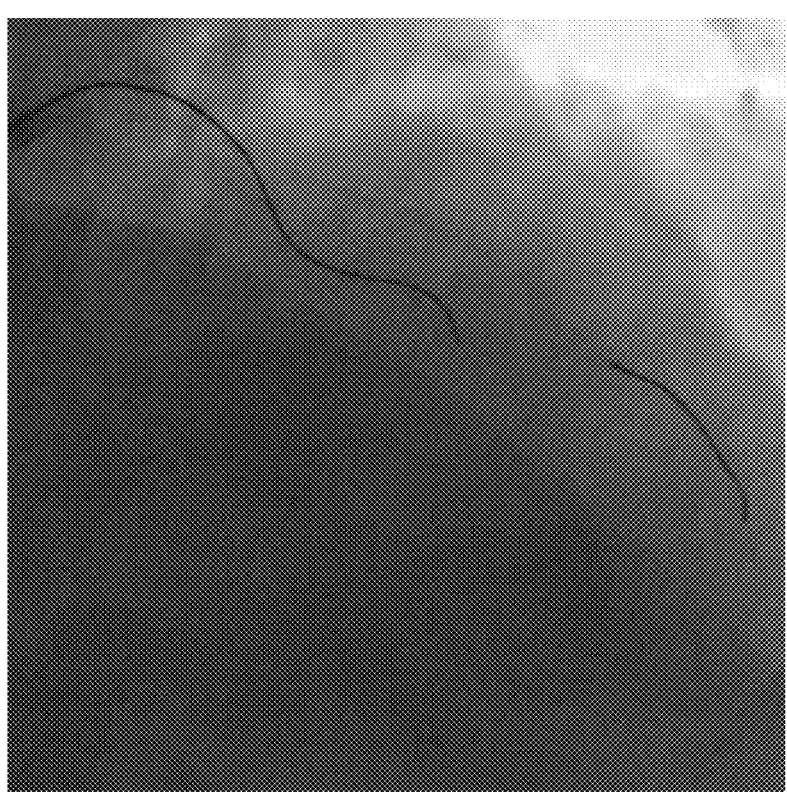
Figure 21D:
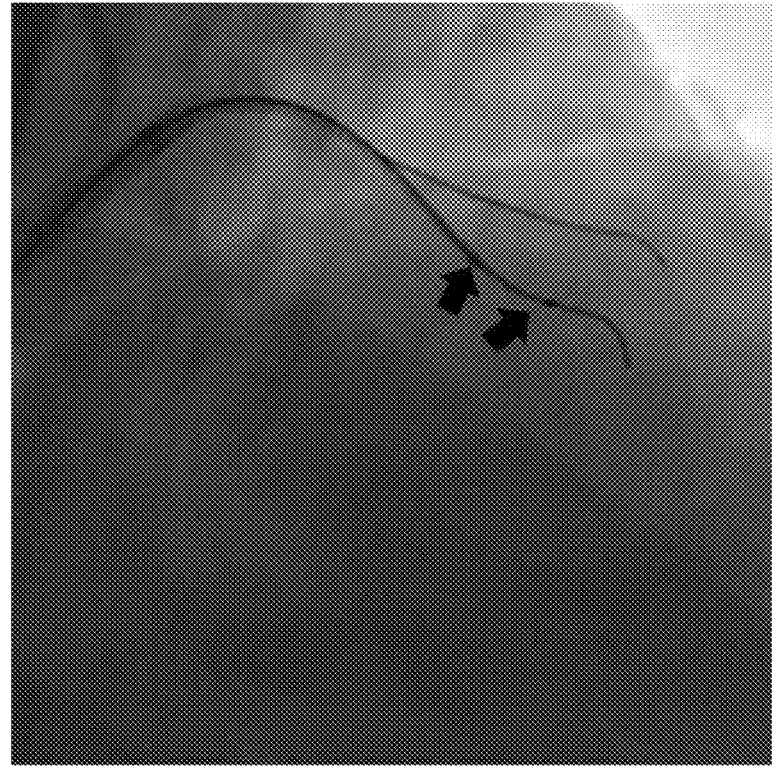
Figure 21E:
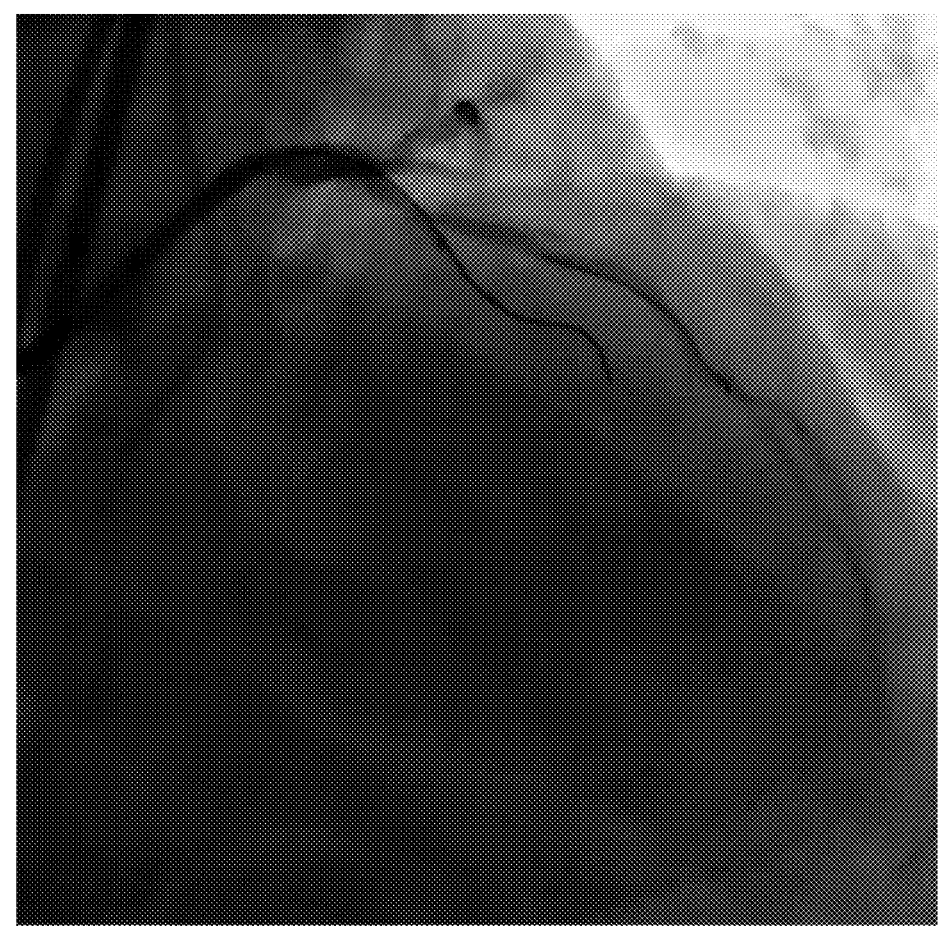

A 74 year-old male presented with CCS class III angina in the setting of left anterior descending artery (LAD) CTO. Dual coronary angiography showed a mid-LAD CTO with tapered proximal cap adjacent to the diagonal branch (FIG. 21A), occlusion length of >20 mm and calcification within the CTO segment (J-CTO score of 2) (FIG. 21B). An AWE strategy was initially used, but the polymer-jacketed guidewire was found to be in the extraplaque space (FIG. 21C) so the ADR technique was performed using an exemplary ADR catheter (FIG. 21D). The catheter was advanced over a MIRACLEBROS® 12 guidewire (Asahi Intecc USA; Irvine, CA) past the distal cap to the re-entry zone in the extraplaque space (FIG. 21E). Retrograde contrast injection showed poor distal target visualization due to extraplaque hematoma formation.

Figures 22A, 22B:
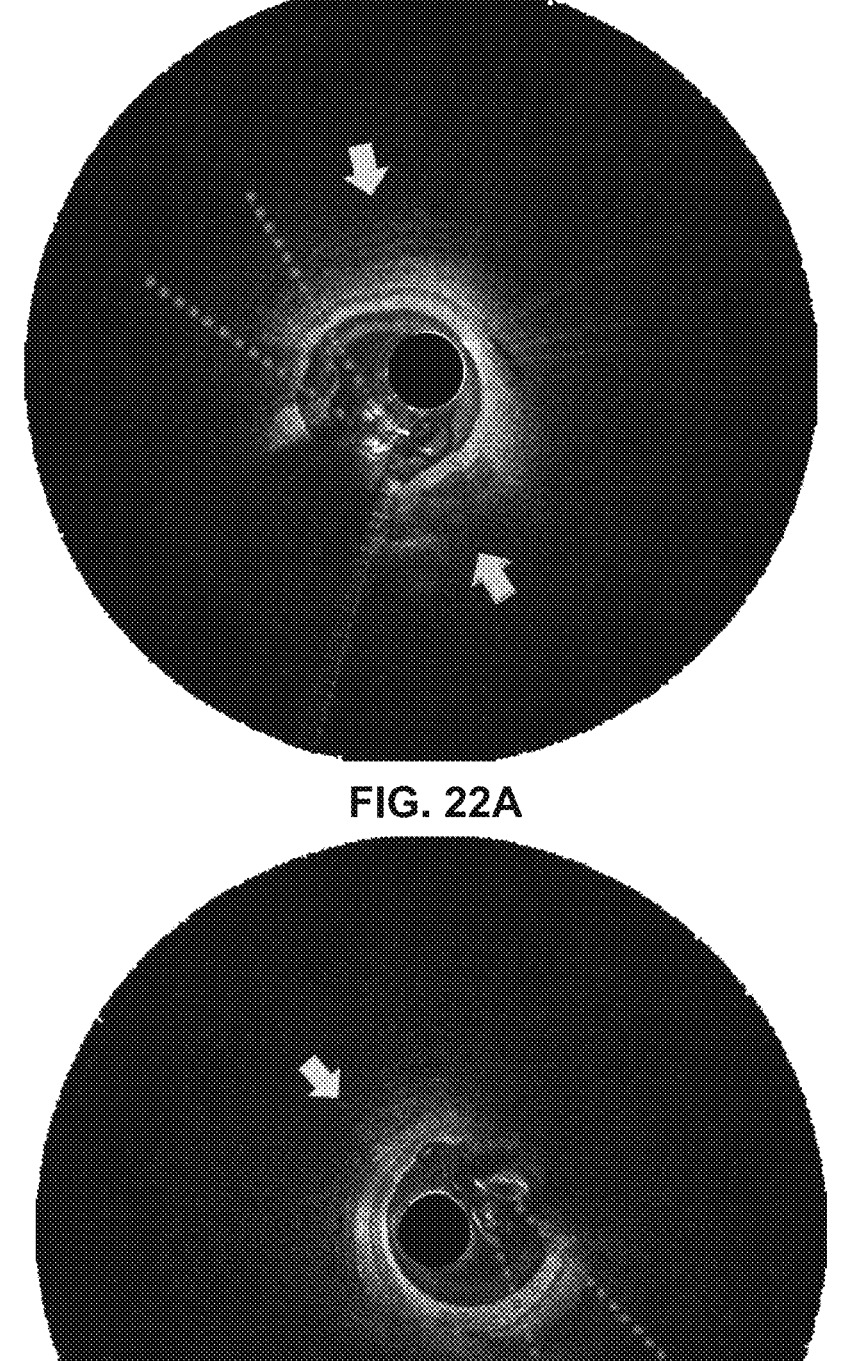
FIGS. 22A and 22B depict OCT images at the same anatomical location but at different rotational orientations.
Figure 22C:
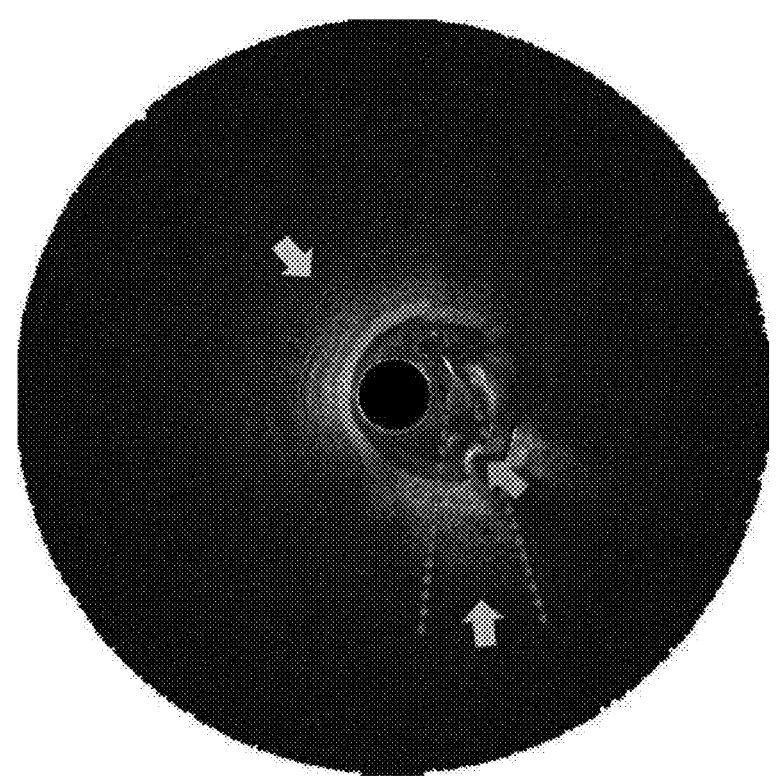
FIGS. 22C and 22D depict OCT and angiogram images at the same anatomical location and similar rotation orientation as FIG. 22B, with a guidewire extending out of the side port.
Figure 22D:
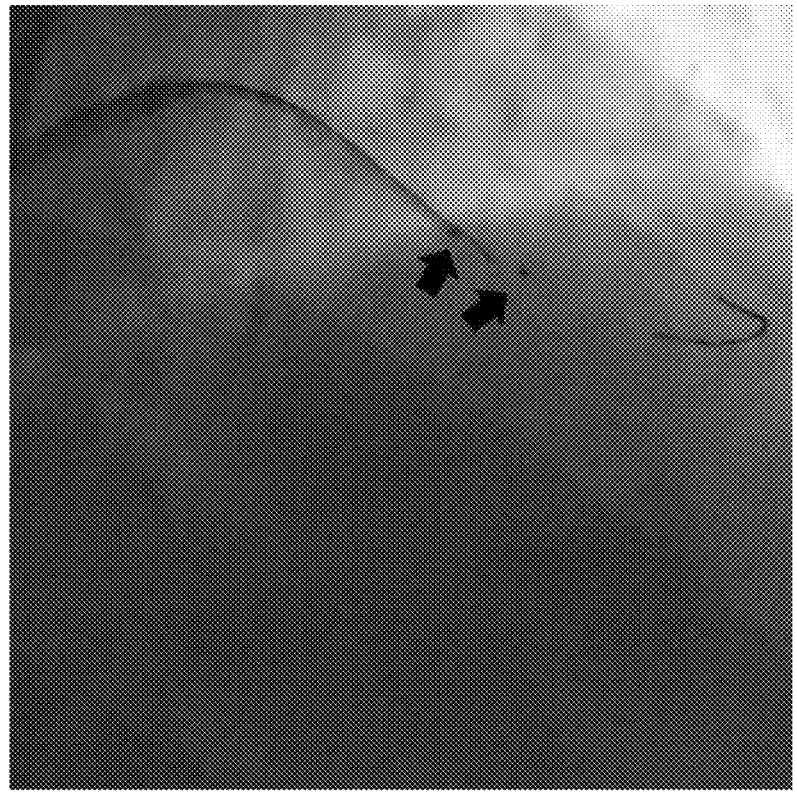
Figure 22E:
FIGS. 22E and 22F are an OCT and angiogram images, respectively, confirming guidewire re-entry.
Figure 22F:
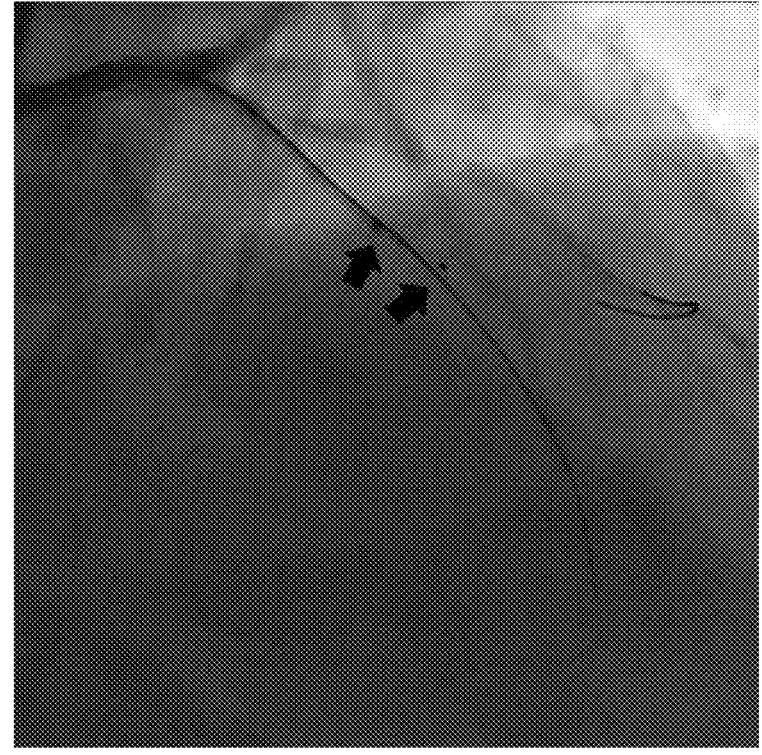
Figure 22G:
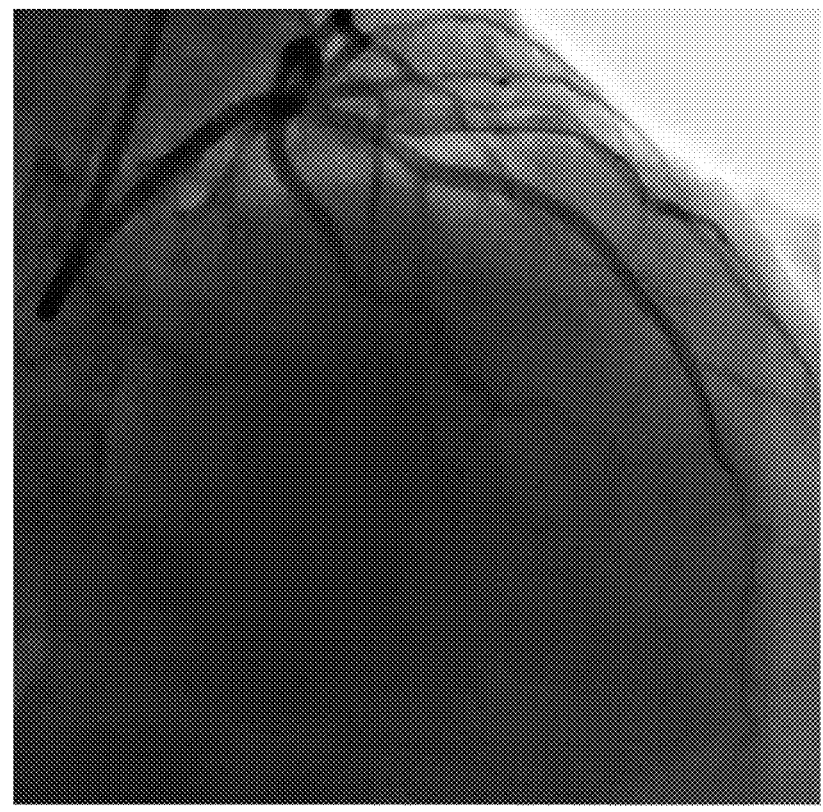
FIG. 22G is an angiogram image after reentry and stenting.

Using the augmented real-time OCT image guidance, a pulsating artery with blood flow—at 5 o'clock in the OCT image/clip—was visualized past the distal cap of the CTO from the extraplaque space (FIG. 22A). The ramp overlay augmentation is depicted by the projecting lines, indicating the side port orientation from which guidewire advancement would be existing, between the two projecting lines. In FIG. 22A, the ramp overlay is pointing in the direction of the adventitia, as marked by the area identifying the fibrous/honeycomb layer structure. The catheter was then torqued/rotated to re-direct the exit ramp overlay augmentation away from the adventitia (10 to 1 o'clock in the OCT image) and towards the true lumen at 5 o'clock in the OCT image/clip (FIG. 22B). An ASTATOR XS 20 wire (Asahi Intecc USA)

was then advanced through the dedicated re-entry port exit ramp (FIGS. 22C and 22D) to successfully re-enter the true lumen in the mid LAD. Guidewire position in the true lumen was confirmed by angiography and OCT imaging (FIGS. 22E and 22F). FIG. 22G shows the final angiographic result and restoration of flow following stent deployment, depicting full recanalization of the LAD after stenting.

The ADR catheter provided real-time OCT based augmentation with orientation information of the catheter relative to displayed vascular morphology (e.g. true lumen, adventitia, calcified nodule, etc.), allowing users to directionally control the coronary guidewire for re-entry. This real time image-guided re-entry helps overcome challenges posed by extraplaque hematoma formation and subsequent loss of distal vessel visualization. The high resolution provides clear morphologic details in conjunction with software augmentation for ease of use, representing significant advancement over current device based re-entry approaches and IVUS-guided techniques.

While some imaging system utilize an array of imaging elements to capture a full 2D image, other imaging systems may use, an image capture sensor that may be moved during image capture in order to obtain a sequence or series of images at different locations. These images may then be aggregated into a single 2D image or a 3D image or model. Examples of such imaging systems include the A-line images captured by an OCT imaging system, or A-mode linear images captured by an ultrasound imaging system. This type of imaging is especially useful in miniaturized and elongated imaging systems found, for example, in catheter-based or endoscopy-based imaging systems where space constraints do not permit a fixed array of imaging elements to capture a complete image. In a catheter-based imaging system, the imaging element may be rotated to capture sequential or consecutive images at a different angular orientations of the imaging element. These images may then be aggregated to provide a two-dimensional representation of the structures surrounding the imaging catheter. Such imaging catheters may be inserted directly into a patient for imaging, or may be inserted into a lumen of another catheter, for example, so that other functions or procedures may be provided by the catheter.

Figure 23B:
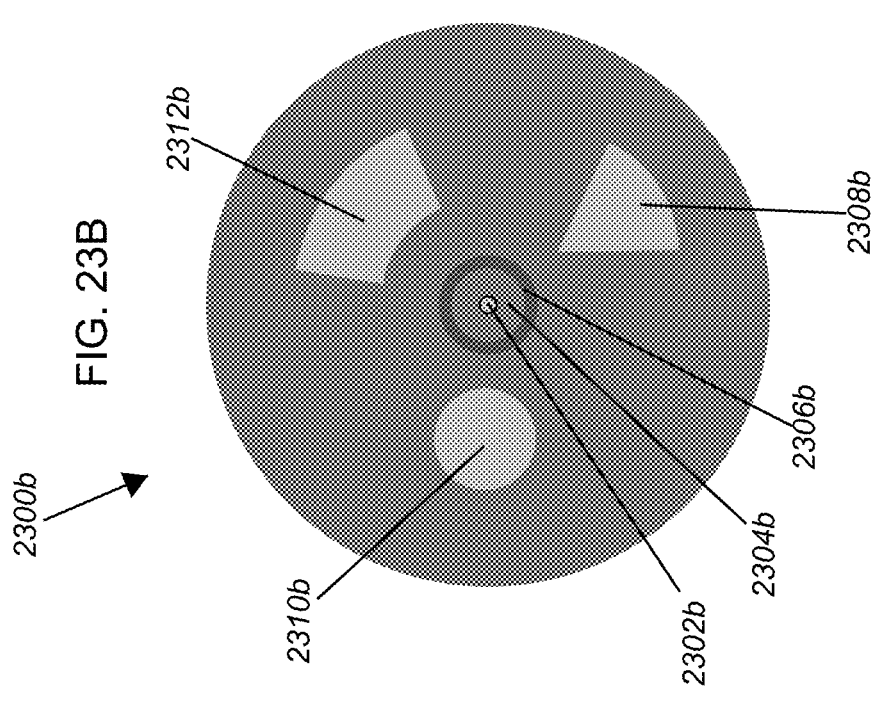
FIG. 23B is the schematic circumferential reconstruction of the waterfall image from FIG. 23A.
Figure 23A:
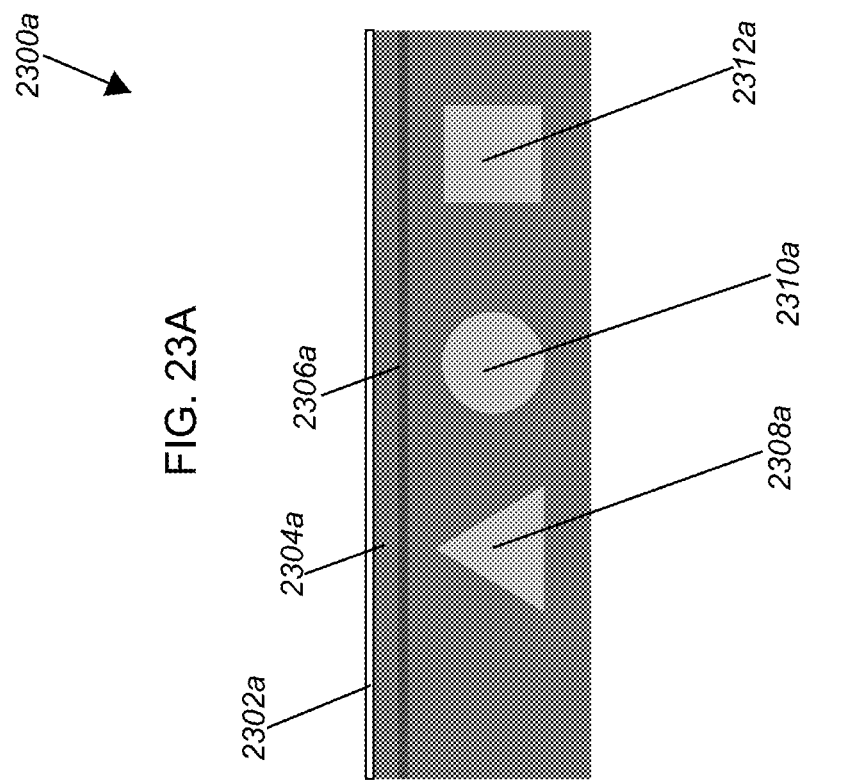
FIG. 23A is a schematic waterfall image of a captured 2D image from a concentric rotational imaging catheter system.

FIG. 23A, for example, schematically illustrate a composite set of consecutive line images in the vertical axis, arranged in a temporal sequence in the horizontal axis and in parallel fashion, known as a waterfall image 2300a, as generated from an imaging catheter located in a larger catheter, e.g. a guide catheter or interventional catheter. The top line 2302a in the image 2300a corresponds to the imager origin or starting location of the imaging element, followed by the rectangular interior zone 2304a of the larger catheter, followed by the outer wall 2306a of the larger catheter. Beyond the wall, various structures 2308a, 2310a and 2312a in the surrounding tissue or environment may be visualized. In this particular example, because the imaging catheter is located in a concentric lumen of another catheter, the distance from the imaging source to the outer wall of the other catheter is nominally a constant distance, so that in the waterfall image 2300a, the outer wall 2306a has a generally linear shape.

Referring to FIG. 23B, the same composite set of consecutive line images may also be arranged in a temporal sequence in a radial fashion, to generate a circumferential image 2300b (or sector view) around the imaging catheter. Because of this radial arrangement of the linear images, the starting location of the imaging element is a circle or point 2302b, rather than the line 2302a depicted in FIG. 23A.

Likewise, the interior zone 2304b of the larger catheter is now an annular zone that is more indicative of the actual geometry of the larger catheter, as is the outer wall 2306b now represented as a circle, rather than the linear line 106a in FIG. 1A. The various structures 2308a, 2310a and 2312a are now depicted in a different position and orientation, respectively, 2308b, 2310b, and 2312b, surrounding the point of reference 2302b of the imager origin.

One potential issue with the reconstruction of the waterfall or radial images is that ideally the movement or rotation rate of the imaging element is nominally uniform or constant, so that the simple aggregation of the linear images into the waterfall or radial images can be uniformly arranged. If, however, the movement or rotation rate is variable, it may result in oversampling or undersampling at some image orientations, which when aggregated, will result in image distortion. This is commonly known as Non-Uniform Rotation Distortion (NURD) of the image. This may result from frictional rotation resistance, which may result in excessive speed after the resistance is overcome or falls.

Figure 24B:
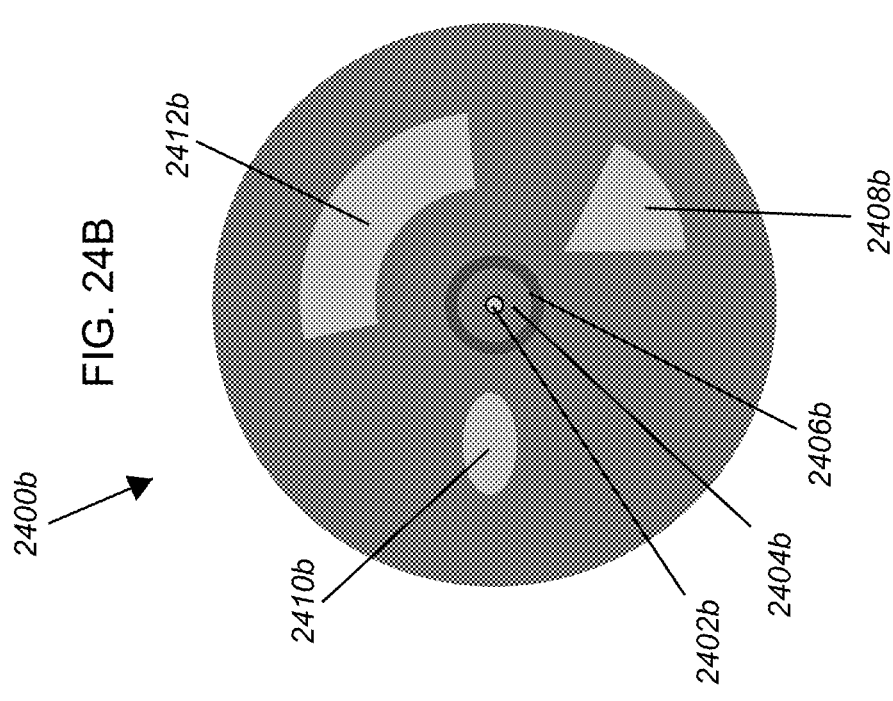
FIG. 24B is the schematic circumferential reconstruction of the waterfall image from FIG. 24A.
Figure 24A:
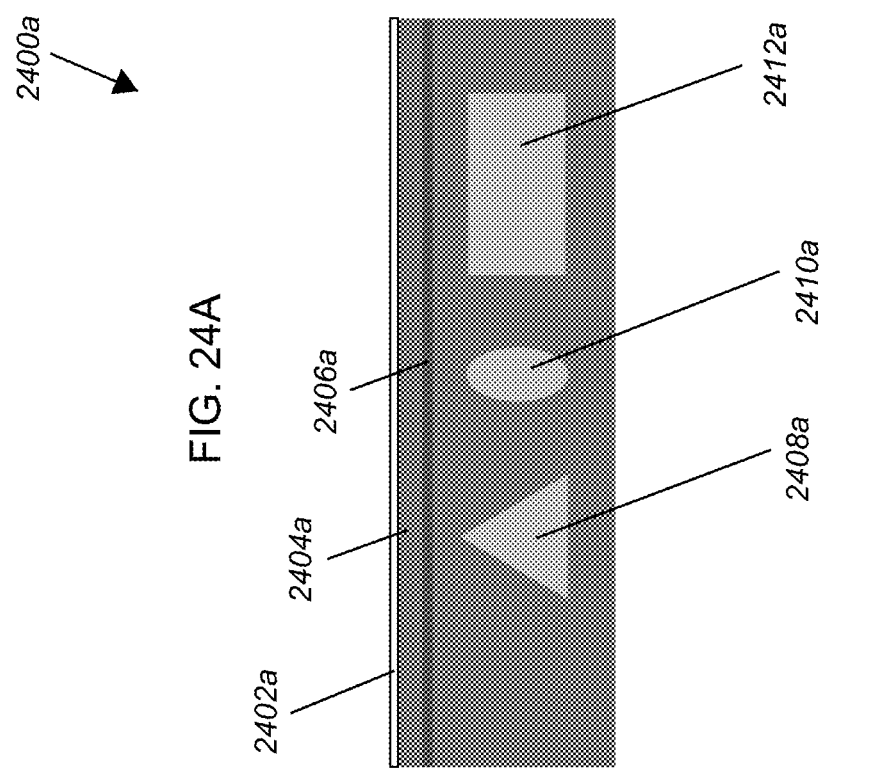
FIG. 24A is a schematic waterfall image of a captured 2D image from a concentric rotational imaging catheter system with distortion from rotational variations.

FIGS. 24A and 24B schematically depicts some of the distortion that may occur. During the scanning of structure 2408a/2408b, if the imaging element is maintained a constant rotation rate, the composite image of structure 2408a/2408b may be relatively accurate and undistorted, as compared to structure 2308a/2308b in FIGS. 23A and 23B. If however, the rotation rate or scanning speed is higher than expected, a particular region may be undersampled, and result in a compressed appearance, as depicted by structures 2410a/2410b in FIGS. 24A and 24B, where they may appear as compressed ovals, compared to the circles 2310a/2310b in FIGS. 23A and 23B. If the rotation rate or scanning speed is slower than expected in a particular region, it may be oversampled and result in a horizontally or circumferentially elongated appearance, as depicted by the structures 2412a/2412b in FIGS. 24A and 24B appearing as rectangles, rather than the square appearance of structures 2312a/2312b in FIGS. 23A and 23B. Notably, however, the wall line and wall circle 2406a/2406b may appear undistorted, due to the lack of effect of the scanning speed or rotation rate on the distance from the imager origin 2402a/2402b to the outer wall 2406a/2406b, where the imaging catheter is concentrically located in the other catheter.

To correct such distortions, some imaging catheters will utilize sensors (such as encoders) and/or fiducials on the catheter in order to detect the speed variations and correct for them. As an example, sensors have to be present at the distal end at the point of signal collection, as well as at the proximal end of the catheter or endoscope from which the imaging element is rotated. Presumably, the proximal end is well-controlled with uniform or constant rotational speed, whereas the imaging element at the distal end collecting incoming signal is experiencing unpredictable and non-uniform friction along the rotational axis. If the differential angular displacement or rotational speed between these two ends may be measured, a distorted image caused by NURD may be corrected. Other image correction algorithms may rely on external fiducials, such as the struts of a stent loaded in the catheter, or deployed into the vessel by the catheter or prior procedure. Others still may analyze the degree of heterogeneity of consecutive line images to detect oversampling and to delete the line images that are causing the distortion. It may be difficult, however, to distinguish oversampled line images from anatomical regions which lack anatomical variability along some sectors of the image. In other words, correction to image distortion requires the ability to detect known periodicity, uniformity, or predictability of an external object at all orientation which is lacking in biological tissue anatomy, or the integration of a sensory means within the construct of the catheter or endoscope.

Figures 25A, 25B:
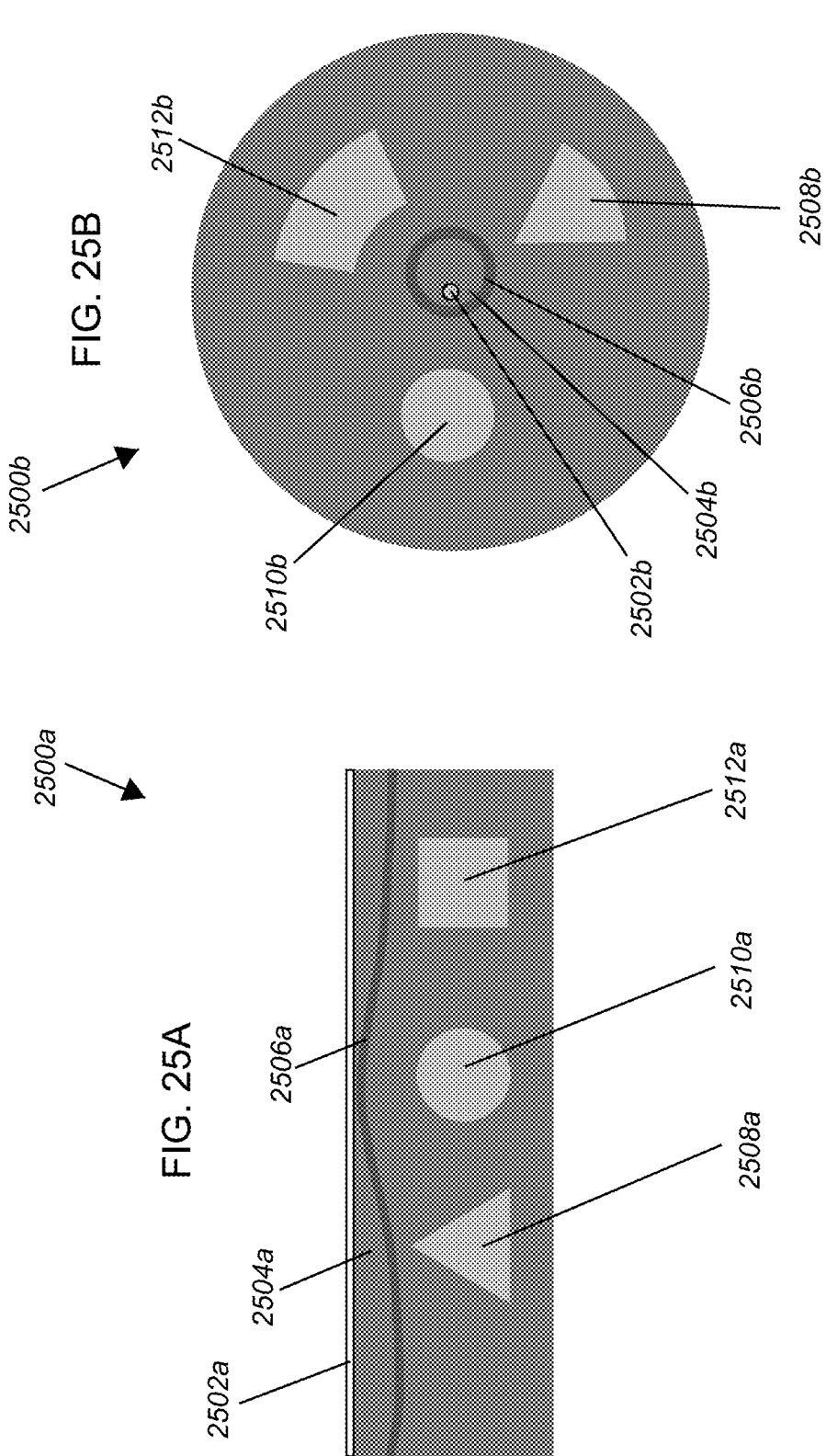
FIG. 25A is a schematic waterfall image of a captured 2D image from an eccentric rotational imaging catheter system.
FIG. 25B is the schematic circumferential reconstruction of the waterfall image from FIG. 25A.

Referring to FIGS. 25A and 25B, if, however, the imaging catheter is located in an imaging lumen of a catheter where the imaging lumen and imaging element is eccentrically located, then the catheter wall 2506*a* in the waterfall image 2500*a* will have a sinusoidal appearance, with the amplitude of the sinusoidal wave proportional to the degree of eccentricity. For a perfectly cylindrical (circular cross-section) catheter with an eccentrically placed imaging element, the catheter wall appearance in the waterfall view is necessarily a complete and single-period sinusoidal wave. On the radial image 2500*b*, the outer wall 2506*b* will still have a circular appearance in a circular catheter, but the outer wall 306*b* will be offset from the imager origin 2502*b*. If a uniform movement or rotation rate/speed is maintained, structures 2508*a/b*, 2510*a/b* and 2512*a/b* will be largely unaffected by the eccentric location of the imaging catheter if the catheter materials are generally transparent as to OCT imaging.

Figure 26B:
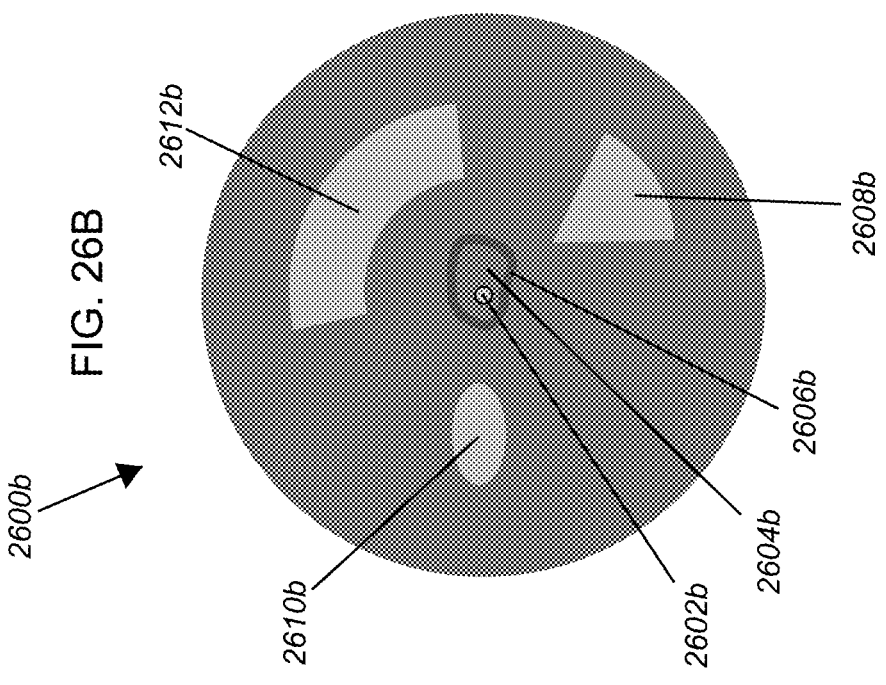
FIG. 26B is the schematic circumferential reconstruction of the waterfall image from FIG. 26A.
Figure 26A:
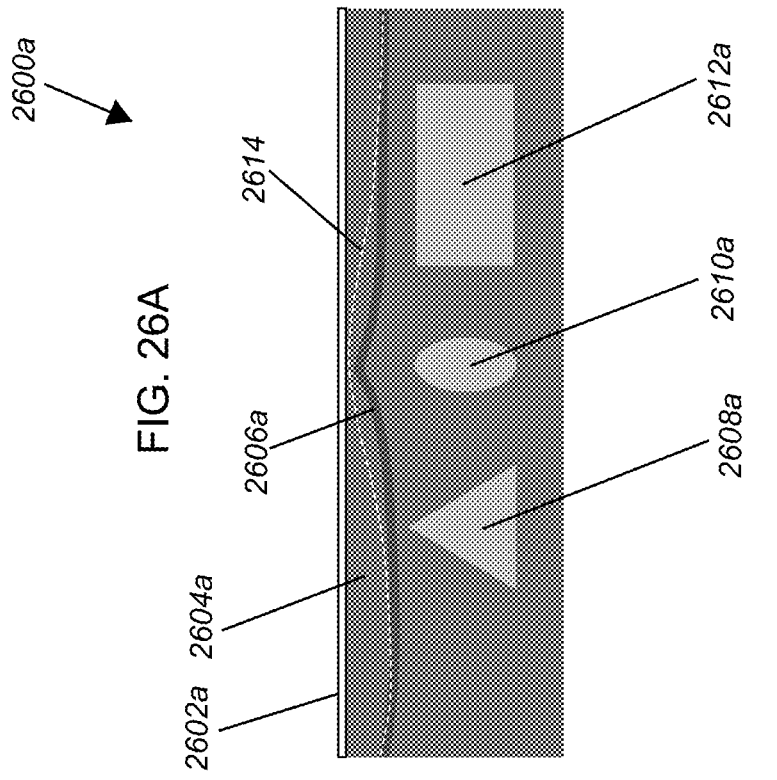
FIG. 26A is a schematic waterfall image of a captured 2D image from an eccentric rotational imaging catheter system with distortion from rotational variations.

If the rotation rate varies during image acquisition, the resulting images from an eccentric imaging catheter will exhibit deviations in the sinusoidal pattern of the outer wall of the larger catheter, which are not generally seen in the wall line images of a concentric imaging catheter system. FIGS. 26A and 26B, for example, depicts outlying structures 2608*a/b*, 2610*a/b* and 2612*a/b* that were imaged with the same rotation rate variations as in FIGS. 24A and 24B. Here, however, the outer wall line 2606*a* may deviate from the predicted sinusoidal pattern 2614 on the waterfall image 2600*a*, and have more of a piqued wave pattern 2616 or a flatter sinusoidal pattern, depending on the type of variation occurring. On the radial image 2600*b*, instead of the offset circular shape, the outer wall 2606*b* may have an irregular closed shape or oblong shape.

By utilizing the predicted or reference shape or line of the outer wall of the larger catheter, however, the outer wall locations of the actual line images that are acquired by be adjusted to conform to the predicted or reference shape or line of the outer wall, thereby compensating for the image distortion caused by uniform allocation of non-uniform line images in the waterfall image, which can then be used to construct the radial image with less distortion.

Figure 27:
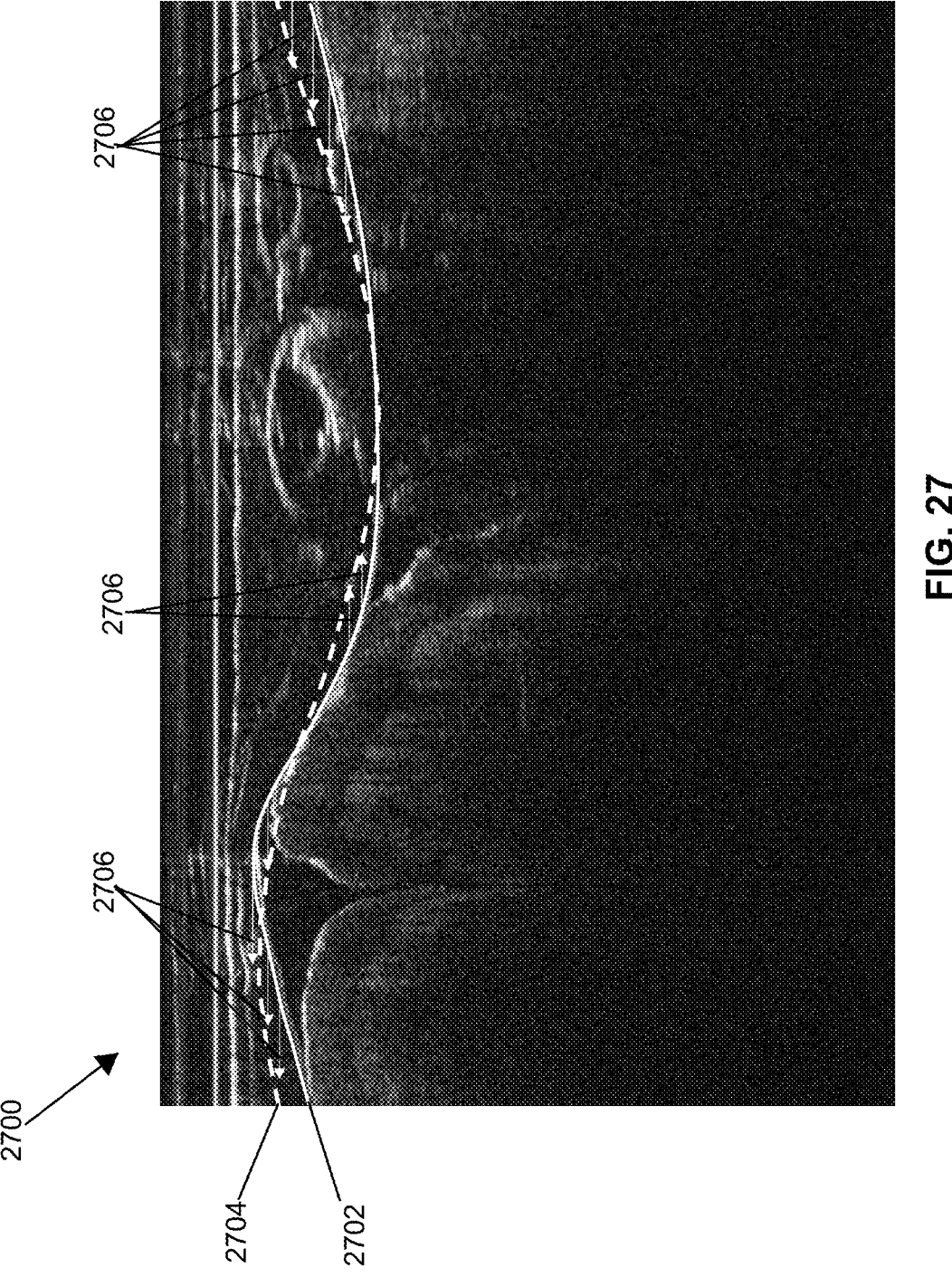
FIG. 27 is an exemplary waterfall image from an eccentric OCT catheter system annotated with the imaged and predicted catheter edge and the corresponding set of image corrections.

FIG. 27 depicts an exemplary waterfall image 2700 obtained from an OCT imaging catheter inserted into an imaging lumen of a multi-lumen catheter. The solid line 2702 represents the identified or detected outer wall of the multi-lumen catheter from the acquired series of line images making up the waterfall image, from one 360 degree set of acquired line images. The dashed line 2704 represents the one period of a reference sinusoidal line pattern that would have been expected had the imaging catheter maintained a uniform rotation speed. To correct for the variations in rotation speed, one or more line images may be deleted from the waterfall image to horizontally or temporally shift the wall location of the remaining line images to a relative location within the period or time interval of line images that matches the reference wall location in the reference sinusoidal line pattern. This horizontal shifting is depicted by arrows 2706. This deletion of line images to conform to the reference sinusoidal line pattern corrects the relative distortion, without significant loss in image detail, as the density of the A-lines are typically much higher than the pixel density of high resolution display.

In one embodiment, to minimize processing time so that the corrected OCT images can be displayed during the procedure with minimal time delay, only the deletion of line images from the acquired images is performed to reduce image distortion. In other variations, however, interpolation is applied to the undersampled region to somewhat restore the lost data and maintain overall image resolution. This may, however, introduce additional processing time that may result in lag or delay in the corrected image display.

In another embodiment, the edge location of the catheter wall along each A-line in the waterfall view is located and the resulting edge deviation is compared to a template sine wave aligned to the peak, valley, or any reference point along the template, and all the A-lines are then re-adjusted and shifted such that the edge locations are aligned to the template. The catheter walls and reference points can be detected through use of existing methodologies including traditional image processing and neural networks. The A-Line adjustment can be done through various methods including brute force pick-and-place or matrix transforms. When reconstructed in the sector view, the image is now undistorted and corrected.

In another embodiment, a model characterizing the NURD is created, a remapping matrix to reverse the distortion is produced, and the matrix is applied to the distorted waterfall image to produce a corrected waterfall image. Model constants can be inferred real-time by leveraging catheter wall detection methods previously described and includes properties such as the imaging element's acceleration and velocity. Alternatively, one or more fixed models can be used if the NURD observed can be generalized across devices, cutting down on computational cost and minimizing processing time at a slight cost in quality.

Figure 28A:
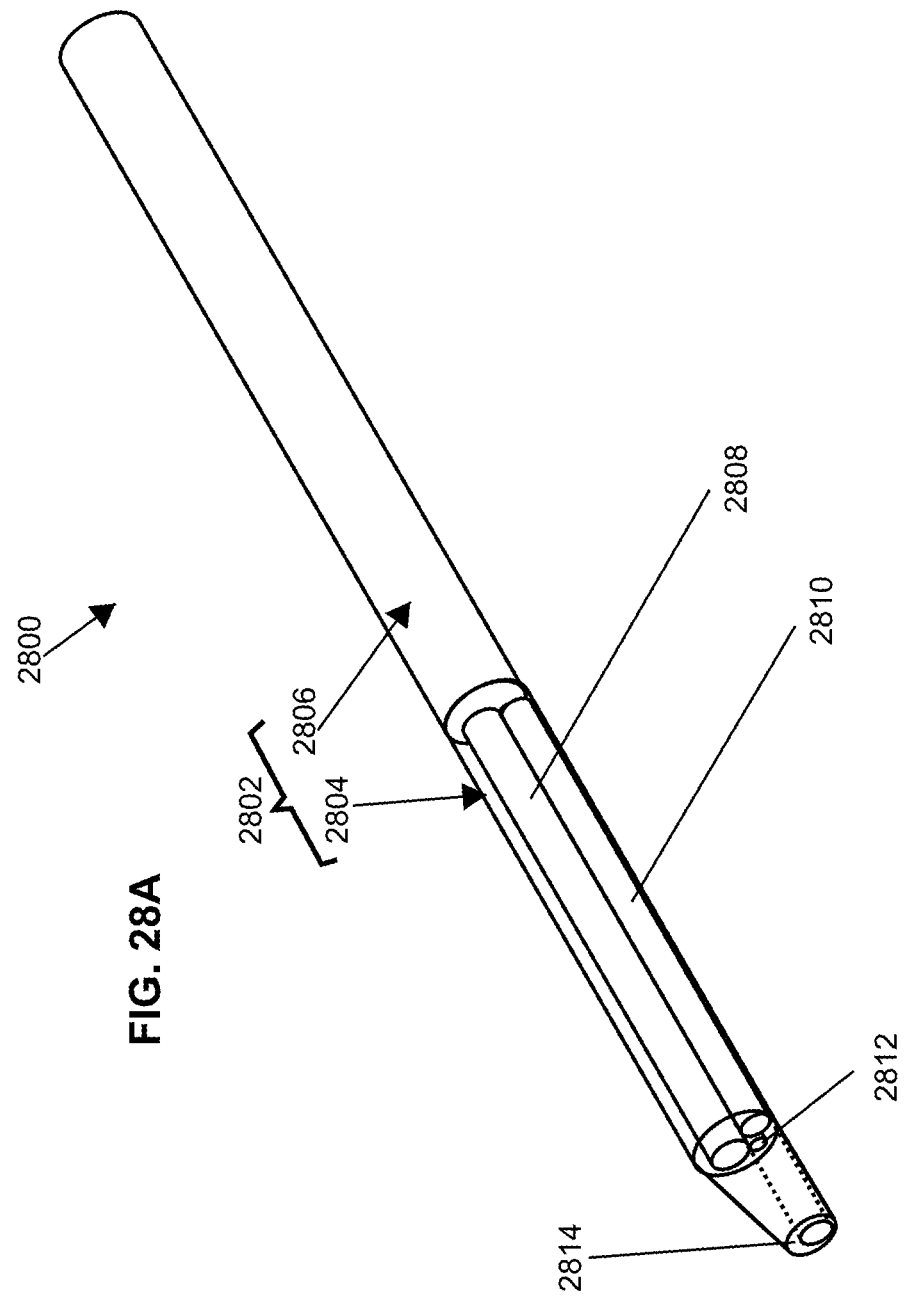
FIG. 28A is schematic perspective view of an exemplary multi-lumen catheter with an eccentric imaging lumen.
Figure 28C:
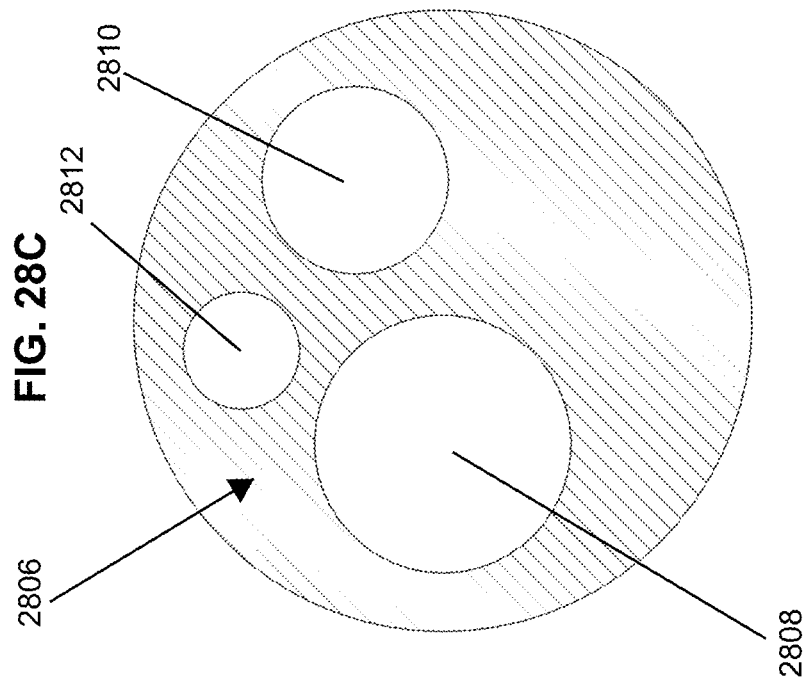
FIGS. 28B and 28C are various cross-sectional views of the catheter in FIG. 27.
Figure 28B:
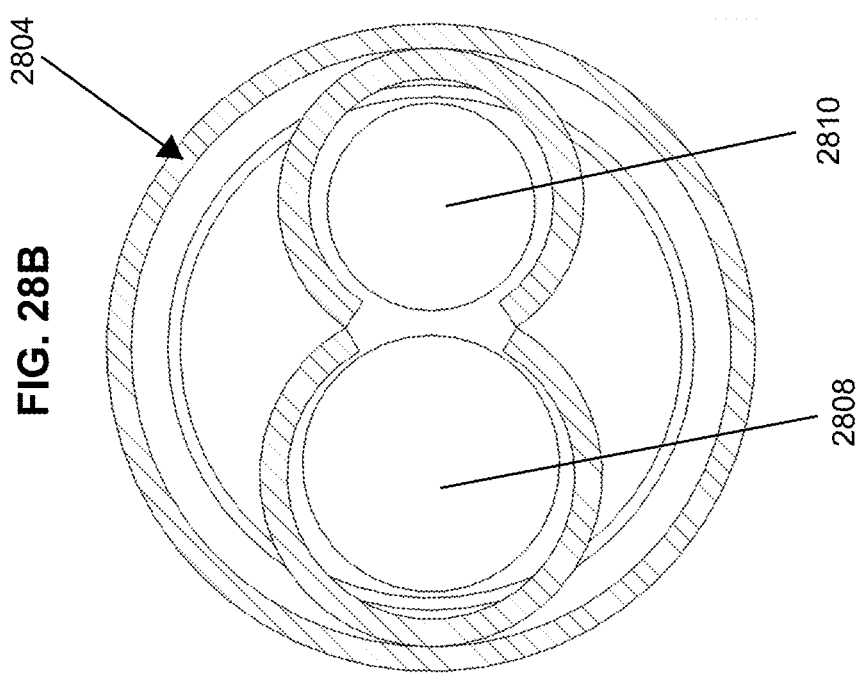
Figures 29A, 29B, 29C:
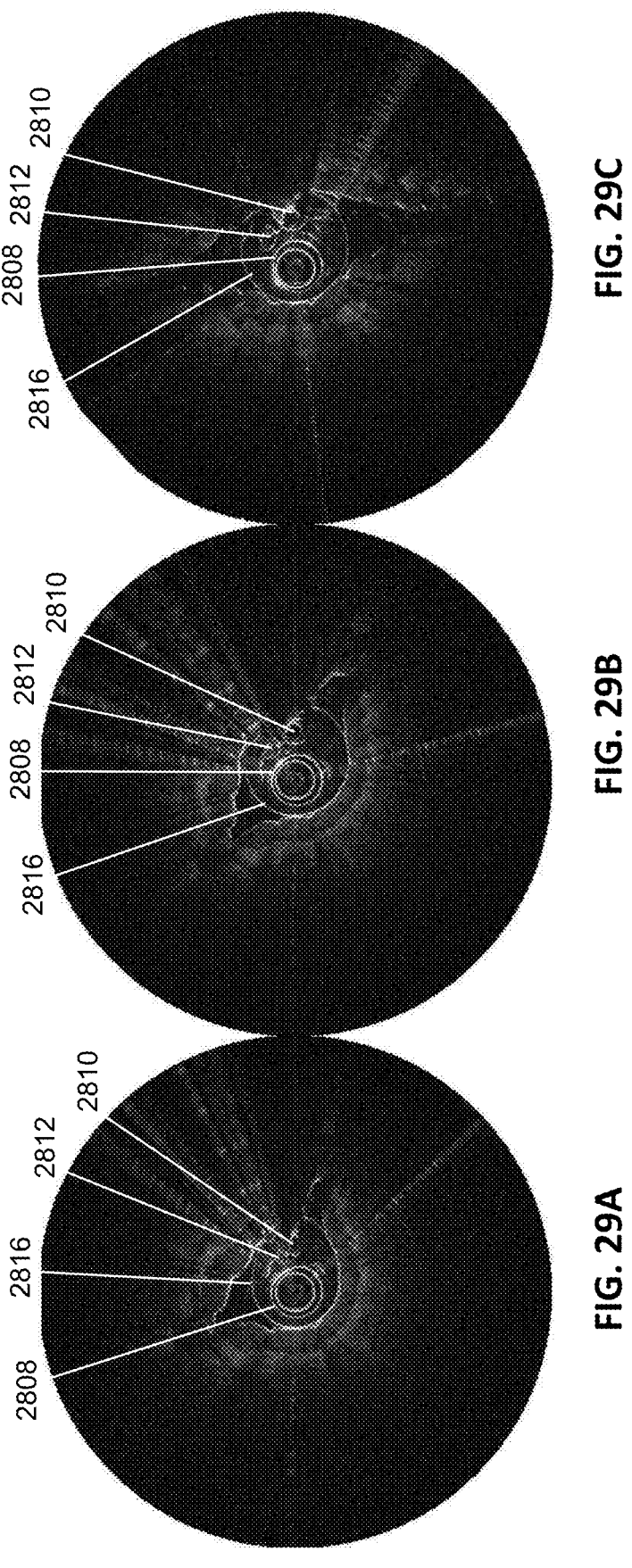
FIGS. 29A and 29B are exemplary pre- and post-correction OCT images, respectively, captured from the exemplary catheter in FIG. 28A.
FIG. 29C is a reference OCT image from the same imaging location as FIGS. 29A and 29B with limited or no significant rotational distortion.
Figures 30A, 30B, 30C:
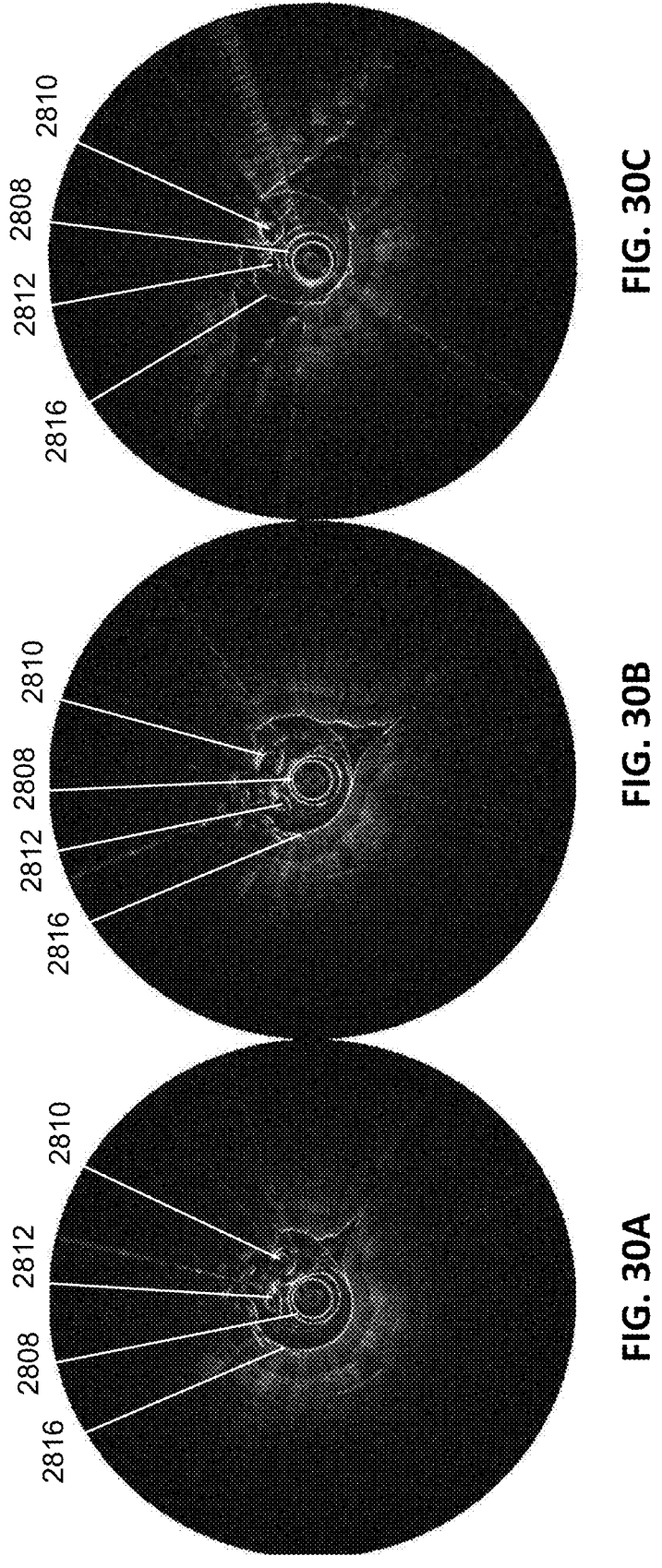
FIGS. 30A to 30C are exemplary pre-correction, post-correction and references OCT images captured from the exemplary catheter in FIG. 28A.
Figures 31A, 31B, 31C:
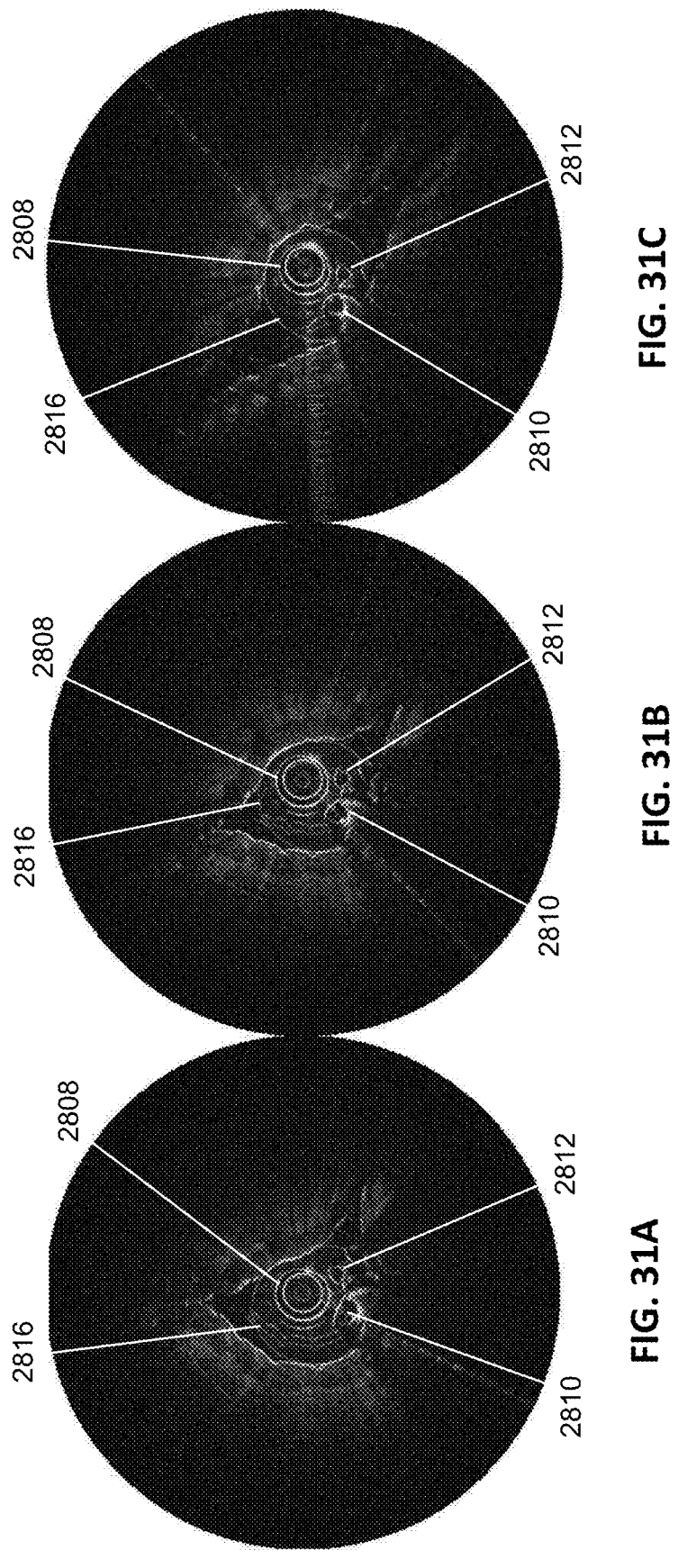
FIGS. 31A to 31C are exemplary pre-correction, post-correction and references OCT images captured from the exemplary catheter in FIG. 28A.
Figures 32A, 32B, 32C:
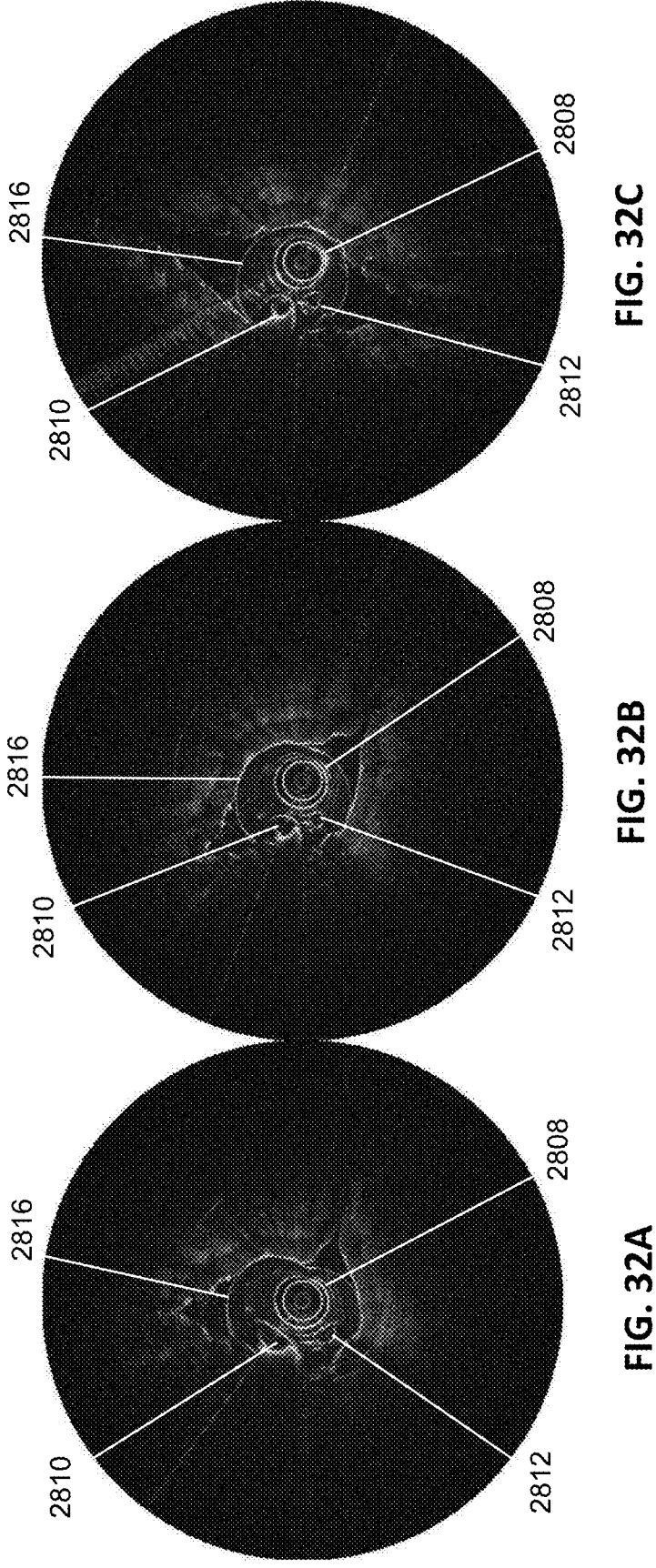
FIGS. 32A to 32C are exemplary pre-correction, post-correction and references OCT images captured from the exemplary catheter in FIG. 28A.

FIGS. 28A to 28C are various schematic views of the multi-lumen catheter 2800 used to capture the OCT images in FIG. 27 and FIGS. 29A to 32C. The catheter 2800 includes a housing 2802. For illustrative purposes, the housing 2802 includes an imaging section 2804 which facilitates imaging of structures and/or tissues surrounding the catheter 2800, located at the distal end of a catheter body 2806. The imaging section 2804 may comprise a material that is optically transparent, to reduce imaging opacity with respect to the selected imaging modality, e.g. OCT or ultrasound. However, it is noted that the imaging section 2804 may be opaque, transparent or partially transparent. For example, for an optical imaging modality such as OCT, the imaging section 2804 may be optically transparent or partially transparent; for an ultrasound imaging modality the imaging section may be transparent, partially transparent or opaque, as along as the material provides for acoustic coupling of ultrasound. The change in optical index between the outer wall 2816 of the imaging section 2804 and the surrounding biological liquid and tissue will highlight the visibility of the outer wall 2816 on images, as depicted in FIGS. 29A to 32C.

The imaging body 2804 may be integrally formed with or distinct from the catheter body 2806. The catheter 2800 includes an imaging lumen 2808 and a guidewire lumen 2810. The imaging lumen 2808 and the guidewire lumen 2810 may extend generally parallel to a longitudinal axis of the catheter 2800. The imaging lumen 608 may be configured to receive an optical coherence tomography ("OCT") imaging device. The guidewire lumen 2810 may be configured to receive a guidewire (not shown). The guidewire lumen 2810 may extend to a distal end 2814 of the catheter 2800 thereby allowing the guidewire to extend out of the catheter 2800. The catheter 2800 may also include an indicator lumen 2812 (partly obscured by the guidewire lumen 2810). The indicator lumen 2812 may be configured to receive a material that may be detectable by the OCT imaging device. In a particular example, the material received by the indicator lumen 2812 may be more easily or reliably detectable by the OCT imaging device and may be used as a fiducial to perform further image processing or distortion correction. The indicator lumen 2812 may also be used for other functions, including but not limited to the flushing blood to improve imaging clarity, or injecting diagnostic or therapeutic agents into the surrounding tissue.

The structures of the multi-lumen catheter 2800, such as the guidewire lumen 2810 and indicator lumen 2812, are visible on the image of FIG. 27, along with the outer wall 2702. FIGS. 29A, 30A, 31A, and 32A depict other exemplary unprocessed OCT images capture via an OCT imaging catheter located in catheter 2800. FIGS. 29B, 30B, 31B and 32B depicted corresponding processed images with the distortion correction described above. FIGS. 29C, 30C, 31C and 32C are reference images that are generally representative of ideal images with minimum inherent distortion taken with the catheter 600 at locations corresponding to the distorted and processed images.

If a uniform rotation rate can be maintained, the size and shape of the sinusoidal pattern can be predicted or derived from the model geometry of the imaging lumen of the larger catheter. This reference sinusoidal pattern, however, may be subject to additional variations other than the variability in rotation rate. For example, if the imaging catheter is smaller than internal diameter of the imaging lumen of the larger catheter, there may be additional variance in the imager origin location, which may also change during an imaging procedure as the imaging catheter and/or larger catheter are bent or torqued. Alternatively, the reference sinusoidal pattern may be obtained by obtaining reference calibration images from the catheter assembly, under ideal conditions that may minimize rotation rate variations, e.g. the catheter is in a straight configuration, without any bending, and/or in a reduced friction liquid.

The image correction described herein may be used with OCT catheter and endoscopic systems, ultrasound catheter systems, and may be used for imaging of a variety of anatomical structures, lumens or ducts, including but not limited to vascular lumens such as arteries and veins, lymphatic ducts, nasal cavity, external ear, internal ear, esophagus, stomach, duodenum, small intestine, large intestine, rectum, bronchi, urethras, ureters, and the like, of humans, mammals and non-mammals. Applications are not limited to biological imaging, and may be used for industrial and other applications.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean ±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

What is claimed is:

1. A system for imaging a lumen, comprising:
   an imaging catheter comprising:
   a tubular body comprising:
      a proximal end region;
      a distal end region; and
      a middle region;
      an imaging lumen located along the proximal, middle and distal regions;
      a common guidewire lumen located along the proximal, middle and distal regions;
      a side ramp lumen located in the distal end region and connected to the common guidewire lumen, and comprising a distal opening in a sidewall of the tubular body;
      a distal guidewire lumen, located in the distal end region and connected to the common guidewire lumen, and comprising a distal opening at an endwall of the tubular body;
      at least one guidewire bias structure, the at least one guidewire bias structure selected from a group consisting of:
         a reduced diameter region at a junction of the distal guidewire lumen and the common guidewire lumen;
         an offset distance between a longitudinal axis of the common guidewire lumen and a longitudinal axis of the distal guidewire lumen;
         an angled flap at or proximal to a junction of the distal guidewire lumen and the common guidewire lumen; and
         a guidewire lumen bump at or proximal to the junction of the distal guidewire lumen and the common guidewire lumen;
   a proximal catheter assembly, comprising a catheter housing coupled to the proximal end region of the tubular body and a proximal optical connection interface;
   a first guidewire port in fluid communication with the common guidewire lumen;
   an imager port in fluid communication with the imaging lumen; and
   an imaging optical fiber connected to the proximal optical connection interface and extending along the imaging lumen.

2. The system of claim 1, further comprising a second guidewire port in fluid communication with the common guidewire lumen, wherein the second guidewire port has a different interface than an interface of the first guidewire port.

3. The system of claim 2, wherein the first and second guidewire ports are located in a hub distal to the catheter assembly.

4. The system of claim 1, wherein the catheter housing further comprises an imager actuator engaged to the imaging optical fiber and configured to longitudinally translate the imaging optical fiber relative to the imaging lumen.

5. The system of claim 1, further comprising a catheter rotation actuator, coupled to the tubular body and configured to rotate the tubular body relative to the proximal catheter housing assembly.

6. The system of claim 5, wherein the catheter rotation actuator is rotatably coupled to a distal end of the catheter housing.

7. The system of claim 2, wherein the proximal catheter assembly further comprises an optical cable between the catheter housing and the proximal optical connection interface.

8. The system of claim 2, wherein the proximal optical connection interface is direct coupled to the catheter housing.

9. The system of claim 1, further comprising an imaging console, the console comprising:

a console housing;

a power supply;

a laser source comprising an output port;

a sled interconnection interface;

a touchscreen interconnection interface; and a large display interconnection interface.

10. The system of claim 9, where in the laser source output port comprises an imaging port and an aiming beam port.

11. The system of claim 9, further comprising a sled assembly, the sled assembly comprising:

a sled housing;

a catheter interconnect;

a sled power actuator; and a catheter detachment actuator.

12. The system of claim 1, wherein the side ramp lumen and the distal guidewire lumen are oriented at an angle in the range of 10 degrees to 45 degrees.

13. The system of claim 1, wherein the tubular body further comprises an indicator lumen.

14. The system of claim 13, wherein the average diameter of the indicator lumen is smaller than the average diameter of the distal guidewire lumen, which is smaller than the average diameter of the common lumen, which is smaller than the average diameter of the imaging lumen.

15. The system of claim 11, wherein the sled housing comprises a distal cavity configured to receive the catheter housing.

16. A re-entry catheter system, comprising:

an elongate catheter body, the catheter body comprising:

a proximal end;

a distal end;

a common lumen extending from the proximal location at the proximal end to a distal location proximal to the distal end, comprising a first longitudinal central axis;

a distal lumen extending from the distal location of the common lumen to the distal end of the catheter body, wherein the distal lumen has comprise a second longitudinal central axis that is parallel and offset from the first longitudinal central axis; and a side lumen extending distally from the distal location of the common lumen to a side wall location of the catheter body wherein the side wall location is proximal to the distal end of the catheter body;

an imaging lumen extending from the proximal end of the catheter body;

a proximal catheter handle coupled to the proximal end of the catheter body, the handle comprising:

a catheter body rotator knob configured to rotate the catheter body relative to the proximal catheter handle; and an imaging catheter displacement knob configured to longitudinally displace an imaging catheter inserted into the catheter body relative to the catheter body.

17. The catheter system of claim 16, wherein the side wall location of the side lumen is located proximal to a closed distal end of the imaging lumen.

18. The catheter system of claim 16, wherein the distal end of the catheter body is an asymmetrically tapered cone shape.

19. The catheter system of claim 16, wherein the catheter body further comprises an indicator lumen.

20. The catheter system of claim 19, wherein the average diameter of the indicator lumen is smaller than the average diameter of the distal lumen, which is smaller than the average diameter of the common lumen, which is smaller than the average diameter of the imaging lumen.

\* \* \* \* \*